US012799176B2

(12) United States Patent
Karrer et al.

(10) Patent No.: US 12,799,176 B2
(45) Date of Patent: *Nov. 17, 2026

(54) COMPOSITIONS COMPRISING FACTOR H-LIKE PROTEIN VARIANTS FOR USE IN TREATING OCULAR DISEASES

(71) Applicant: Character Biosciences, Inc., Jersey City, NJ (US)

(72) Inventors: Erik Karrer, Los Altos, CA (US); Maria Avrutsky, Jersey City, NJ (US); Jonathan Gumucio, San Francisco, CA (US); Marcel Van Der Brug, Daly City, CA (US)

(73) Assignee: CHARACTER BIOSCIENCES, INC., Jersey City, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 19/437,284

(22) Filed: Dec. 30, 2025

(65) Prior Publication Data

US 2026/0116937 A1 Apr. 30, 2026

Related U.S. Application Data

(63) Continuation of application No. 18/994,598, filed as application No. PCT/US2023/070241 on Jul. 14, 2023.

(60) Provisional application No. 63/389,355, filed on Jul. 14, 2022.

(51) Int. Cl.

| | |
|---|---|
| ***C07K 14/47*** | (2006.01) |
| ***A61K 9/00*** | (2006.01) |
| ***A61K 38/00*** | (2006.01) |
| ***A61P 27/02*** | (2006.01) |

(52) U.S. Cl.

CPC .......... *C07K 14/472* (2013.01); *A61K 9/0048* (2013.01); *A61P 27/02* (2018.01); *A61K 38/00* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 10,426,817 | B2 | 10/2019 | Rudolf et al. | |
| 2011/0130345 | A1 | 6/2011 | Rohrer et al. | |
| 2013/0296254 | A1 | 11/2013 | Deschatelets et al. | |
| 2025/0015396 | A1 | 1/2025 | Han et al. | |
| 2025/0302911 | A1 | 10/2025 | Gumucio et al. | |
| 2026/0015396 | A1 * | 1/2026 | Karrer | C07K 14/472 |

FOREIGN PATENT DOCUMENTS

| | | | | |
|---|---|---|---|---|
| WO | WO2007/098122 | A2 | 8/2007 | |
| WO | WO2018/139991 | A1 | 8/2018 | |
| WO | WO2018/197873 | A1 | 11/2018 | |
| WO | 2021081203 | A1 | 4/2021 | |
| WO | WO2021/081401 | A1 | 4/2021 | |
| WO | 2022094340 | A1 | 5/2022 | |
| WO | WO-2023023278 | A2 * | 2/2023 | C12N 15/86 |

OTHER PUBLICATIONS

Gumucio et al.; U.S. Appl. No. 19/433,697 entitled "Methods of treating age-related macular degeneration," filed Dec. 26, 2025.

Kerrer et al.; U.S. Appl. No. 19/438,393 entitled "Methods of treating ocular diseases using engineered polypeptides comprising complement Factor H and Factor H-like protein domains," filed Dec. 31, 2025.

Gumucio et al.; U.S. Appl. No. 19/417,321 entitled "Compositions for treatment of lipid transport dysfunction," filed Dec. 11, 2025.

Landowski et al.; Targeting lipid metabolism for the treatment of age-related macular degeneration: insights from preclinical mouse models; Journal of Ocular Pharmacology and Therapeutics; 38(1); pp. 3-32; Jan. 1, 2022.

Rudolf et al.; Apolipoprotein AI mimetic peptide L-4F removes Bruch's membrane lipids in aged nonhuman primates; Investigative ophthalmology & visual science; 60(2); pp. 461-472; Feb. 1, 2019.

Rudolf et al.; ApoA-I mimetic peptide 4F reduces age-related lipid deposition in murine bruchs membrane and causes its structural remodeling; Current eye research; 43(1); pp. 135-146; Jan. 2, 2018.

UniProt Accession No. A0A114ZAP8_9ACTV; Regulatory protein, tetR family from Actinomadura madure; UniProtKB; 4 pages; Apr. 12, 2017; retrieved from the internet (https:www.uniprot.org/uniprotkb/A0A1I4ZAP8/entry) on Sep. 2, 2023.

Skerka et al., Defective complement control of Factor H (Y402H) and FHL-1 in age-related macular degeneration, Molecular Immunology, 44, pp. 3398-3406, 2007.

Avrutsky et al., CTX114, a novel complement inhibitor for the treatment of AMD, has enhanced SCR7-mediated ligand binding and complement regulatory activity, ARVO Annual Meeting Abstract, 2 pages, Jun. 2024.

European Application No. 23840573 Supplementary European Search Report dated May 13, 2026.

* cited by examiner

*Primary Examiner* — Sudhakar Katakam

*Assistant Examiner* — Zachary J Miknis

(74) *Attorney, Agent, or Firm* — Goodwin Procter LLP

(57) ABSTRACT

Engineered polypeptides for use in treating ocular diseases may include peptides having short consensus repeat (SCR) regions of complement factor H and Factor H-like proteins. Exemplary peptides may include a first region consisting essentially of complement factor H domains SCR1-SCR7 and a second region that comprises at least complement factor H domain SCR7.

20 Claims, 25 Drawing Sheets

Specification includes a Sequence Listing.

| Attribute | Source data | Optimal FHL-1 SCR7 junction | Optimal CFH SCR6 junction |
|---|---|---|---|
| Protein integrity | FIG. 8 | IR, IRV, IRVS (SEQ ID NO: 7), IRVSF (SEQ ID NO: 6) | --, P, KP, LKP, TLKP (SEQ ID NO: 13) |
| Protein integrity | FIG. 10A, FIG. 11A | IR, IRV, IRVS (SEQ ID NO: 7) | P, KP, LKP, TLKP (SEQ ID NO: 13) |
| Expression level | FIG. 10B, FIG. 11B | IRVS (SEQ ID NO: 7) | LKP, TLKP (SEQ ID NO: 13) |
| **Consensus** | | IRVS (SEQ ID NO: 7) | LKP, TLKP (SEQ ID NO: 13) |

FIG. 12

| Compound | $EC_{50}$ nM ± SD |
|---|---|
| CFH | 595.6 ± 737.4 |
| FHL-1 | 414.6 ± 271.5 |
| FHL-1 culture sup | 703.0 ± 399.6 |
| Var004 culture sup | 2.2 ± 0.8 |
| Var020 culture sup | 4.3 ± 1.6 |

| Protein | $EC_{50}$ nM ± SD |
|---|---|
| CFH | 1.2 ± 0.2 |
| FHL-1 | 7.1 ± 3.7 |
| FHL-1 culture sup | 6.9 ± 1.9 |
| Var004 culture sup | 2.5 ± 0.2 |

| Variant ID | AA Substitution | % Glycosylation | SD |
|---|---|---|---|
| **FHL-1** | **none** | **14%** | **2%** |
| Var090 | L6S | 16% | 3% |
| Var091 | L6T | 13% | 3% |
| Var092 | A289S | 59% | 6% |
| Var093* | A289T | 96% | 0% |
| Var094 | Y380S | 14% | 0% |
| Var095 | Y380T | 37% | 7% |
| Var096 | T16N | 55% | 1% |
| Var097 | D258N | 15% | 3% |
| Var098 | Y334N | 89% | 1% |
| Var099* | D21N | 94% | 1% |
| Var100* | G286N | 91% | 2% |
| Var101 | H355N | 86% | 6% |
| Var102* | A407N | 94% | 0% |
| Var103 | R426N | 56% | 5% |
| Var104 | S428N | 29% | 2% |
| **Var004** | **None** | **11%** | **2%** |
| Var105 | G431N | 33% | 2% |
| Var106 | G436N | 39% | 3% |
| Var107 | G441N | 36% | 3% |
| Var108* | G442N | 95% | 2% |

FIG. 20

| | Variant | AA Substitutions |
|---|---|---|
| FHL-1 framework | FHL-1 | None |
| | Var093 | A289T |
| | Var099 | D21N |
| | Var100 | G286N |
| | Var109 | D21N, G286N |
| | Var110 | D21N, A289T |
| Var004 framework | Var004 | None |
| | Var108 | G442N |
| | Var111 | G442N, D21N |
| | Var112 | G442N, G286N |
| | Var113 | G442N, A289T |
| | Var114 | G442N, D21N, G286N |
| | Var115 | G442N, D21N, A289T |

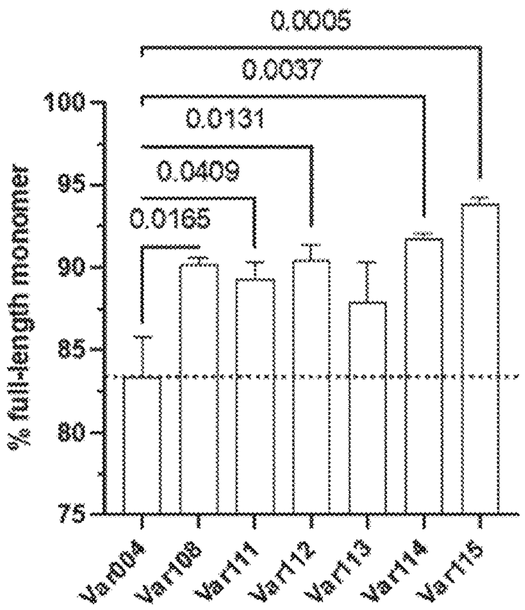
FIG. 22A
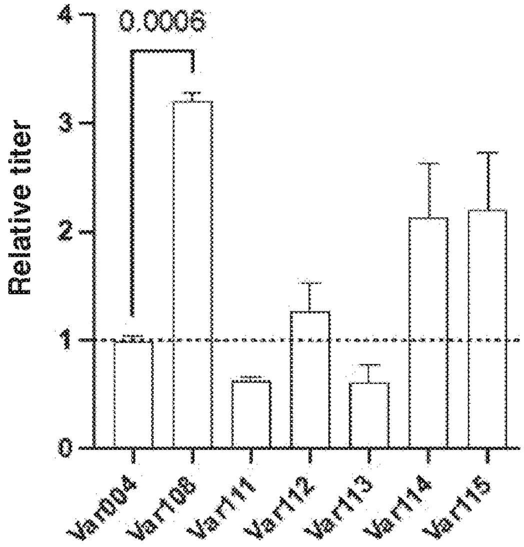
FIG. 22B
| VarID | AA Substitutions | Titer (Relative vs Var004) | % FL monomer |
|---|---|---|---|
| Var004 | Reference | | 83.4 |
| Var108 | G442N | 3.21 | 90.2 |
| Var111 | G442N; D21N | 0.64 | 89.3 |
| Var112 | G442N; G286N | 1.27 | 90.5 |
| Var113 | G442N; A289T | 0.62 | 87.9 |
| Var114 | G442N; D21N; G286N | 2.14 | 91.8 |
| Var115 | G442N; D21N; A289T | 2.20 | 93.9 |
FIG. 23

| Protein | $EC_{50}$ nM (+/- SD) | Relative fold CFH | Relative fold FHL-1 |
|---|---|---|---|
| CFH | 442.7 (558.3) | | |
| FHL-1 | 394.6 (270.5) | | |
| Var108 | 0.4 (0.1) | 1128 | 986 |
| Var114 | 0.6 (0.3) | 739 | 658 |
| Var115 | 0.8 (0.4) | 546 | 493 |

| Protein | $EC_{50}$ nM (+/- SD) |
|---|---|
| CFH | 4.5 (2.8) |
| FHL-1 | 7.4 (0.8) |
| Var108 | 0.4 (0.1) |
| Var114 | 1.1 (1.0) |

| Condition | Binding $EC_{50}$ (nM ± SD) | Binding at 4000nM (signal ± SD) |
|---|---|---|
| CFH | 2681.2 ± 2002.5 | 15.2 ± 12.4 |
| FHL-1 | 1983.0 ± 648.7 | 172.7 ± 94.3 |
| Var108 | 790.5 ± 681.1 | 326.6 ± 104.0 |
| Var114 | 701.2 ± 525.6 | 143.4 ± 62.2 |
| Var115 | 4153.5 ± 2899.8 | 76.8 ± 76.0 |

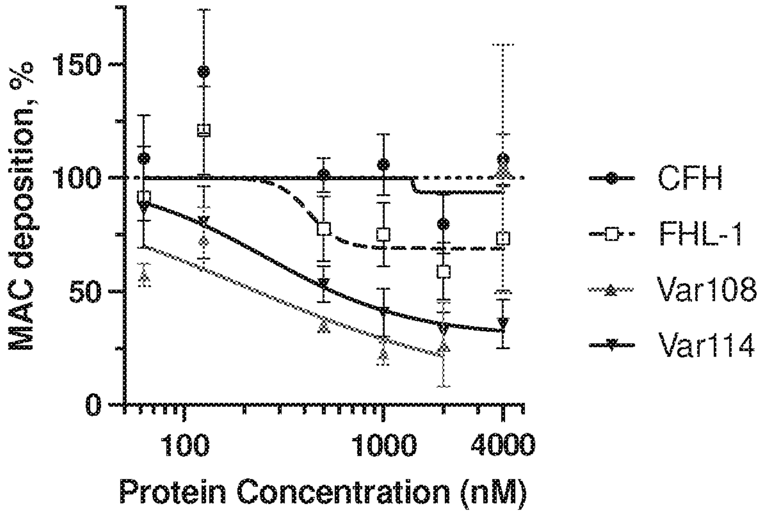
FIG. 27A
| Condition | MAC $IC_{50}$ (nM ± SD) | Max MAC inhibition (100%-$I_{max}$± SD |
|---|---|---|
| CFH | 729.4 ± 416.7 | 8.4 ± 9.1 |
| FHL-1 | 609.1 ± 275.6 | 39.5 ± 52.4 |
| Var108 ** | 249.1 ± 150.7 | -- |
| Var114 | 260.3 ± 139.1 | 71.4 ± 24.5 |
FIG. 27B
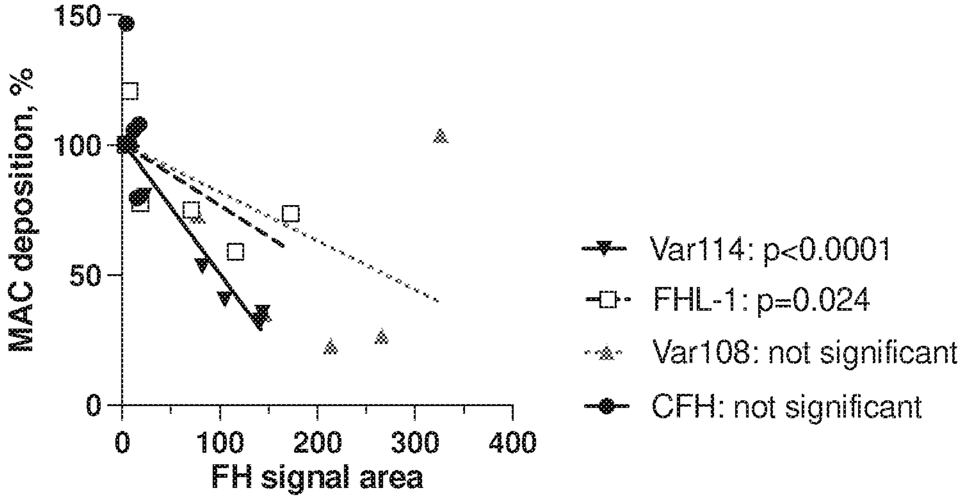
FIG. 28

| Compound | $IC_{50}$ (nM) ± SD |
|---|---|
| CFH | 115.7±44.8 |
| FHL-1 | 116.5±51.1 |
| Var114 | 32.0±25.7 |

| Compound | $IC_{50}$ (nM) ± SD |
|---|---|
| Var114 | 4.3±1.5 |
| CFH | 34.2±14.5 |

| Condition | Binding $EC_{50}$ (nM ± SD) |
|---|---|
| CFH | -- |
| FHL-1 | 1591.8 ± 589.3 |
| Var114 | 537.8 ± 80.4 |

COMPOSITIONS COMPRISING FACTOR H-LIKE PROTEIN VARIANTS FOR USE IN TREATING OCULAR DISEASES

CLAIM OF PRIORITY

This patent application is a continuation of U.S. patent application Ser. No. 18/994,598, titled "THERAPEUTIC COMPOSITIONS AND METHODS FOR AGE-RELATED MACULAR DEGENERATION," filed on Jan. 14, 2025, which is a national phase application under 35 USC 371 of International Patent No. PCT/US2023/070241, titled "THERAPEUTIC COMPOSITIONS AND METHODS FOR AGE-RELATED MACULAR DEGENERATION" filed on Jul. 14, 2023, now International Publication No. WO 2024/015981, which claims priority to U.S. provisional patent application No. 63/389,355, titled "THERAPEUTIC COMPOSITIONS AND METHODS FOR AGE-RELATED MACULAR DEGENERATION," and filed on Jul. 14, 2022, each of which are herein incorporated by reference in its entirety.

SEQUENCE LISTING

The instant application contains a Sequence Listing which has been filed electronically in XML format and is hereby incorporated by reference in its entirety. Said XML copy, created on Jun. 2, 2026, is named 14814-706-2.US0.xml and is 194,410 bytes in size.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Age-related macular degeneration (AMD) is a chronic metabolic inflammatory disease of the eye. AMD is the leading cause of blindness in people over 55 years old and has a relatively high prevalence in the US (e.g., 8.7%) and worldwide. Further, this problem is expected to increase as global populations age. Although AMD is categorized into a variety of types (e.g., early, intermediate, wet and dry), the majority of AMD cases are considered "Dry" AMD, for which there is only one approved therapy.

There are believed to be many associated factors that may contribute to AMD. For example, extracellular deposits of lipids (drusen) are the first pathological signs of AMD. Drusen disrupt and stress retinal pigment epithelium (RPE) cells, the loss of which leads to photoreceptor degeneration and the severe later stages of the disease, including geographic atrophy (GA) and neovascular AMD (nvAMD). There is a need for therapies that may treat both dry and wet AMD.

SUMMARY OF THE DISCLOSURE

Described herein are engineered polypeptides. In particular, engineered therapeutic peptides including short consensus repeat (SCR) regions of complement factor H (or CFH) and SCR regions of Factor H-like protein 1 (or FHL) peptides (e.g., "CFH-FHL" peptides) that may provide one or more therapeutic benefits, as described herein.

In general, an engineered polypeptide may be used to treat age-related macular degeneration (AMD). The engineered polypeptide may have a first peptide sequence of 80% or more homology to SEQ ID NO: 3 (the CFH SCR1-7 N-Terminal Domain), a second peptide sequence of 80% or more homology to SEQ ID NO: 17 (FHL-1 SCR6-7 C-Terminal Domain), and a linker domain separating the first peptide sequence from the second peptide sequence.

In some examples, the linker domain may comprise an FHL-1 SCR7 Junction coupled to the first peptide sequence, in which the FHL-1 SCR7 Junction may have a peptide sequence of SEQ ID NO: 4 to SEQ ID NO: 7, IRV, IR, or I. The linker domain may comprise a CFH SCR6 Junction coupled to the second peptide sequence, the CFH SCR6 Junction may have a peptide sequence of SEQ ID NO: 13 to LKP, KP, or P. The linker domain may comprise a peptide sequence of SEQ ID NO: 11 or SEQ ID NO: 12. The engineered polypeptide may have an amino acid sequence of 90% or more homology to SEQ ID NO: 18 to SEQ ID NO: 132. The first peptide sequence may be 95% or more homologous to the CFH SCR1-7 peptide sequence of SEQ ID NO: 3, and wherein the second peptide sequence may have 95% or more homology to the FHL-1 SCR6-7 peptide sequence of SEQ ID NO: 17. The first peptide sequence may be the CFH SCR1-7 peptide sequence of SEQ ID NO: 3, and the second peptide sequence may be the FHL-1 SCR6-7 peptide sequence of SEQ ID NO: 17. The linker domain may comprise a Gly/Ser linker, a poly-Gly linker or a poly-Ala linker. The linker domain may comprise GGGS (SEQ ID NO: 141), GGGSGGGS (SEQ ID NO: 142), GGGGSGGGS (SEQ ID NO: 143), GGGGSGGGSGGGS (SEQ ID NO: 144), or GGGGSGGGGSGGGGS (SEQ ID NO: 11). The linker domain may comprise EAAAK (SEQ ID NO: 145), EAAAKEAAAK (SEQ ID NO: 146), or EAAAKEAAAKEAAAK (SEQ ID NO: 12).

In some examples, the engineered polypeptide may comprise a linker domain having a peptide sequence 90% or more homology to SEQ ID NO: 11 or SEQ ID NO: 12. The linker domain may be a Gly/Ser linker, a poly-Gly linker or a poly-Ala linker. The linker domain may contain a first peptide sequence comprised of SEQ ID NO: 4 to SEQ ID NO: 7, IRV, IR, or I. The linker domain may also contain a second peptide sequence comprised of SEQ ID NO: 13 to LKP, KP, or P.

In general, an engineered polypeptide for use in treating AMD may have a first peptide sequence of SEQ ID NO: 3, linked to a second peptide sequence of 80% or more homology to an FHL-1 SCR6-7 peptide sequence of SEQ ID NO: 17, wherein the second peptide sequence can be separated from the second peptide sequence by a peptide linker comprising a peptide sequence of SEQ ID NO: 11 or SEQ ID NO: 12.

In general, an engineered polypeptide for use in treating AMD may have a first region of peptide sequence of at least 90% homology to SEQ ID NO: 3, linked to a second peptide sequence having at least 90% homology to either SEQ ID NO: 17 by a peptide linker region.

For example, the engineered polypeptides described herein (which may be for use in treating age-related macular degeneration) may generally have the sequence of any of SEQ ID NO: 125, SEQ ID NO: 131, or SEQ ID NO: 132.

In some examples the engineered polypeptide comprises: a first peptide sequence of one of: SEQ ID NO: 3, SEQ ID NO: 139 or SEQ ID NO: 140; a second peptide sequence of SEQ ID NO: 17, and a linker domain between the first peptide sequence and the second peptide sequence of one of: SEQ ID NO: 138. Any of these polypeptides may include a first junction region between the first peptide sequence and the linker domain, wherein the first junction region has a sequence of one of: SEQ ID NO: 4-7, IRV, IR, or I, and a second junction region between the linker domain and the second peptide sequence, wherein the second junction region has a sequence of one of: SEQ ID NO: 13, LKP, KP, or P. For example, the first junction region may have the sequence of SEQ ID NO: 7 and the second junction region has the sequence of SEQ ID NO: 13.

An engineered polypeptide for use in treating age-related macular degeneration (AMD) may have a first peptide sequence of SEQ ID NO: 3, a second peptide sequence of SEQ ID NO: 17, and a linker domain separating the first peptide sequence from the second peptide sequence. As mentioned, the engineered polypeptide may include a first peptide sequence of 80% or more homology to SEQ ID NO: 3, a second peptide sequence of 80% or more homology to SEQ ID NO: 17, a linker domain separating the first peptide sequence from the second peptide sequence. The linker domain may comprise an FHL-1 SCR7 Junction coupled to the first peptide sequence, the FHL-1 SCR7 Junction having a peptide sequence of SEQ ID NO: 4 to SEQ ID NO: 7, IRV, IR, or I. In some examples the linker domain comprises a CFH SCR6 Junction coupled to the second peptide sequence, the CFH SCR6 Junction having a peptide sequence of SEQ ID NO: 13 to LKP, KP, or P. The linker domain may generally comprise a peptide sequence of SEQ ID NO: 11 or SEQ ID NO: 12.

For example, described herein are the engineered polypeptides having an amino acid sequence of any of SEQ ID NO: 18-97, SEQ ID NO: 99-106, SEQ ID NO: 122-125, or SEQ ID NO: 128-132. The first peptide sequence may be homologous (e.g., 80% homologous or more, 85% homologous or more, 90% homologous or more, 95% homologous or more, 99% homologous or more) to the CFH SCR1-7 peptide sequence of SEQ ID NO: 3, and the second peptide sequence may be homologous (e.g., 80% homologous or more, 85% homologous or more, 90% homologous or more, 95% homologous or more, 99% homologous or more) to the FHL-1 SCR6-7 peptide sequence of SEQ ID NO: 17. The linker domain may comprise a Gly/Ser linker, a poly-Gly linker or a poly-Ala linker; in some examples the linker domain comprises one of: GGGS (SEQ ID NO: 141), GGGSGGGS (SEQ ID NO: 142), GGGGSGGGS (SEQ ID NO: 143), GGGGSGGGSGGGS (SEQ ID NO: 144), or GGGGSGGGGSGGGGS (SEQ ID NO: 11), EAAAK (SEQ ID NO: 145), EAAAKEAAAK (SEQ ID NO: 146), or EAAAKEAAAKEAAAK (SEQ ID NO: 12).

For example, described herein are engineered polypeptides for use in treating age-related macular degeneration (AMD) comprising a first peptide sequence of 80% or more homology to SEQ ID NO: 3, a second peptide sequence of 80% or more homology to SEQ ID NO: 17, a linker domain separating the first peptide sequence from the second peptide sequence, a first junction region between the first peptide sequence and the linker domain and a second junction region between the second peptide sequence and the linker domain. The first junction region may have the sequence of SEQ ID NO: 7 and the second junction region has the sequence of SEQ ID NO: 13 or LKP. The linker domain may comprise a peptide sequence of SEQ ID NO: 11.

For example, an engineered polypeptide for use in treating age-related macular degeneration (AMD) may have a sequence of 80% or more homology to SEQ ID NO: 131. For example, an engineered polypeptide for use in treating age-related macular degeneration (AMD) may have a sequence of 90% or more homology to SEQ ID NO: 131. In some examples the engineered polypeptide for use in treating age-related macular degeneration (AMD) has the sequence of SEQ ID NO: 131.

For example, an engineered polypeptide for use in treating age-related macular degeneration (AMD) may comprise the sequence of SEQ ID NO: 125. An engineered polypeptide for use in treating age-related macular degeneration (AMD) may comprise the sequence of SEQ ID NO: 131. An engineered polypeptide for use in treating age-related macular degeneration (AMD) may comprise the sequence of SEQ ID NO: 132.

In some examples, an engineered polypeptide for use in treating age-related macular degeneration (AMD) may have a first peptide sequence of SEQ ID NO: 3, linked to a second peptide sequence of 80% or more homology to an FHL-1 SCR6-7 peptide sequence of SEQ ID NO: 17, wherein the second peptide sequence is separated from the second peptide sequence by a peptide linker comprising a peptide sequence of SEQ ID NO: 11 or SEQ ID NO: 12. An engineered polypeptide for use in treating age-related macular degeneration (AMD) may have a first region of peptide sequence of at least 90% homology to SEQ ID NO: 3, linked to a second peptide sequence having at least 90% homology to either SEQ ID NO: 17 by a peptide linker region.

An engineered polypeptide for use in treating age-related macular degeneration (AMD) may have a peptide sequence of at least 80% homology to any one of SEQ ID NO: 18-137. For example, an engineered polypeptide for use in treating age-related macular degeneration (AMD) may have a peptide sequence of at least 90% homology to any one of SEQ ID NO: 18-137. An engineered polypeptide for use in treating age-related macular degeneration (AMD) may have a sequence of any one of SEQ ID NO: 18-137.

Also described herein are pharmaceutical compositions using any of these engineered polypeptides. For example a pharmaceutical composition for use in prevention or treatment of age-related macular degeneration (AMD) in a patient may include any of the polypeptides described above and a pharmaceutically acceptable excipient. In some examples the composition may be configured, adapted and/or compounded for administration by intraocular injection. In some examples multiple different engineered polypeptides as described herein may be used. For example, the pharmaceutical composition may include two or more of the engineered polypeptides described herein.

Any of these engineered polypeptides may be glycosylated at one or more sites. For example, polypeptides of SEQ ID NO: 125, 131 or 132 all include engineered glycosylation sites. Any of the compositions described herein may be fully glycosylated or partially glycosylated (e.g., some or all of the engineered polypeptide may be glycosylated). For example, 40% or more of the engineered polypeptide in the composition may be glycosylated (45% or more, 50% or more, 55% or more, 60% or more, 65% or more, 70% or more, 75% or more, 80% or more, 85% or more, 90% or more, 95% or more, or substantially all of the engineered polypeptide in the composition may be glycosylated).

Also described herein are methods of treating a patient using any of these engineered polypeptides. For example described herein is a method of treating or preventing age-related macular degeneration (AMD) in a patient using the engineered polypeptide or pharmaceutical composition including any of these engineered polypeptides.

For example, a method of treating or preventing age-related macular degeneration (AMD) in a patient using the engineered polypeptide or pharmaceutical composition of any of these engineered polypeptides (e.g., wherein the prevention or treatment is prevention of said AMD) may include administering the composition in a patient diagnosed as having a propensity to develop AMD. The engineered polypeptide (or a composition including the engineered polypeptide) may be delivered in any appropriate manner, including orally, systemically, by injection, etc. For example, a method of treating or preventing age-related macular degeneration (AMD) in a patient using an engineered polypeptide or pharmaceutical composition including any of the engineered polypeptides described herein may include administering to the patient one or more doses of the engineered polypeptide or a composition including the engineered polypeptide. The patient may be showing signs or symptoms of AMD. These methods may include prevention or treatment of early-stage AMD. Any of these methods may include delivering the engineered polypeptide or composition of any of these engineered polypeptides into the patient's eye. For example, any of these methods may include delivering the engineered polypeptide or a composition of an engineered polypeptide by intraocular injection. In some examples, delivering comprises delivering more than one of the engineered polypeptides or compositions of any of these engineered polypeptides.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 8A compares sets of variants containing the same FHL-1 SCR7 junction. FIG. 8B compares sets of variants containing the same CFH SCR6 junction.

FIG. 12 is a table illustrating an example of a summary of results from measuring the protein expression of engineered variants of FHL-1 that contain $[GGGGS]_3$ (SEQ ID NO: 11) linkers. Optimal junction sequences are those that conferred significantly improved properties relative to nonoptimal junction sequences, as shown in the source data.

FIG. 20 illustrates a table and examples of amino acid substitutions in FHL-1 variants and their extent of glycosylation as described herein. Asterisks indicate variants with >90% glycosylation.

FIG. 22A is a bar graph showing the amount of full length protein measured from western blot analysis using anti-CFH antibody for multiple glycosylated variants, as described herein. Percent full-length monomer was quantified by measuring densitometry of full-length monomer divided by densitometry of total lane from monomer through 25 kDa.

FIG. 22B is a bar graph showing the relative protein expression level of multiple glycosylated variants relative to FHL-1 variants, as described herein. Relative protein expression levels were determined by dividing the band intensity of each variant by the band intensity of Var004.

FIG. 23 shows an example of data in a table summary of quantification of protein integrity and relative protein expression levels measured from western blot analysis using anti-CFH antibody.

FIGS. 27A and 27B illustrate examples of surface-dependent complement inhibitory activity of an engineered variant of FHL-1 (e.g., Var108, Var114) and control proteins (e.g. FHL-1, CFH) on cultured human RPE cells (ARPE-19 cell line), as measured by anti-C5b9 (MAC) antibody immunostaining. The table of FIG. 27B summarizes the IC50 values and maximal complement inhibition across multiple experiments.

FIG. 28 is a graph illustrating binding-function relationships for engineered variants of FHL-1 (e.g. Var108, Var114) and control proteins (FHL-1, CFH) in the surface-dependent complement inhibitory assay from FIGS. 27A-27B, and the binding assay from FIG. 26. Correlation between cell surface binding and complement inhibition was tested by linear regression.

FIG. 30B is a table summarizing the IC50 values from multiple experiments.

DETAILED DESCRIPTION

Figure 1A:
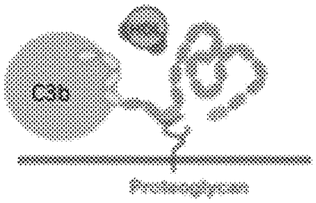
FIG. 1A schematically illustrates proteoglycan binding activity of a CFH protein in a complement pathway in the normal case.

The compositions and methods described herein may be used to treat AMD, and in particular, AMD patients whose disease is primarily driven by dysfunction of complement.

In some examples, including (but not limited to) disease in which the primary contributing factor is due to a complement pathway, the patient may be treated with one or more FHL-1 engineered variants. In particular, these one or more FHL-1 engineered variants (also referred to herein as CFH-FHL peptides or CFH-FHL peptide variants) are those that improve complement inhibition and decrease lipid accumulation in Bruch's membrane, to prevent or reduce AMD-related effects. For example, the methods described herein may replace deficient complement and lipid regulation in Bruch's membrane by intravitreal injection of recombinant FHL-1 variants having improved proteoglycan binding activity, such as those having the protein sequence shown in SEQ ID Nos. 18-137.

CFH is a negative regulator of complement activation and acts upstream of neovascularization and retinal cell death. The compositions and methods described herein may provide a therapeutic for AMD that regulates and/or restores complement and lipid homeostasis. These compositions are engineered for improved proteoglycan binding activity and may improve complement inhibition and reduce apolipoprotein binding.

These compositions, such as the FHL-1 engineered variants described herein, may include multiple repeats of one or more of the SCR6, SCR7, SCR8 modules from human CFH or FHL-1, separated by one or more linker regions.

The disclosure herein provides compositions and methods for treating, preventing, or inhibiting diseases of the eye. For example, the disclosure herein provides recombinant factor-H-like protein 1 (FHL-1) protein and FHL-1 engineered variant proteins. The disclosure provides methods of treating, preventing, or inhibiting diseases of the eye by intraocularly (e.g., intravitreally) administering an effective amount of these compositions of the disclosure to treat or prevent diseases of the eye using the methods provided herein. Diseases of the eye that may be treated or prevented using these methods include but are not limited to glaucoma, macular degeneration (e.g., age-related macular degeneration, AMD), diabetic retinopathies, inherited retinal degeneration such as retinitis pigmentosa, retinal detachment or injury and retinopathies (such as retinopathies that are inherited, induced by surgery, trauma, an underlying etiology such as severe anemia, SLE, hypertension, blood dyscrasias, systemic infections, or underlying carotid disease, a toxic compound or agent, or photically).

Unless otherwise defined herein, scientific and technical terms used in this application shall have the meanings that are commonly understood by those of ordinary skill in the art.

Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well-known and commonly used in the art. In case of conflict, the present specification, including definitions, will control.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, and chemical analyses.

Where aspects or examples of the disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the example disclosed. Exemplary methods and materials are described herein, although methods and materials similar or equivalent to those described herein can also be used in the practice or testing of the present disclosure. The materials, methods, and examples are illustrative only and not intended to be limiting.

Definitions

The following terms, unless otherwise indicated, shall be understood to have the following meanings:

As used herein, "residue" refers to a position in a protein and its associated amino acid identity. As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5 'and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-0-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, examples wherein phosphate is replaced by P(0)S("thioate"), P(S)S ("dithioate"), (O)NRi ("amidate"), P(0)R, P(0) OR', CO or CH2 ("formacetal"), in which each R or R' is independently H or substituted or unsubstituted alkyl (1-20 C) optionally containing an ether (-0-) linkage, aryl, alkenyl, cycloalkyl, cycloalkenyl or araldyl. Not all linkages in a polynucleotide need be identical. The preceding description applies to all polynucleotides referred to herein, including RNA and DNA.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

"Homologous," in all its grammatical forms and spelling variations, refers to the relationship between two proteins that possess a common sequence, including protein sequence from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," particularly (but not exclusively) when modified with a percentage may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin. "Percent (%) sequence identity" or "percent (%) identical to" with respect to a reference polypeptide (or nucleotide) sequence is defined as the percentage of amino acid residues (or nucleic acids) in a candidate sequence that are identical with the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, "isolated molecule" (where the molecule is, for example, a polypeptide, a polynucleotide, or fragment thereof) is a molecule that by virtue of its origin or source of derivation (1) is not associated with one or more naturally associated components that accompany it in its native state, (2) is substantially free of one or more other molecules from the same species (3) is expressed by a cell from a different species, or (4) does not occur in nature.

As used herein, "purify," and grammatical variations thereof, refers to the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition).

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

The terms "patient", "subject", or "individual" are used interchangeably herein and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In some examples, the subject is a human that is at least 40, 45, 50, 55, 60, 65, 70, 75, 80, 85, 90 or 95 years of age.

In one example, the subject has, or is at risk of developing a disease of the eye. A disease of the eye, includes, without limitation, retinitis pigmentosa, rod-cone dystrophy, Leber's congenital amaurosis, Usher's syndrome, Bardet-Biedl Syndrome, Best disease, retinoschisis, Stargardt disease (autosomal dominant or autosomal recessive), untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, glaucoma, or retinal vein occlusion. In another example, the subject has, or is at risk of developing glaucoma, Leber's hereditary optic neuropathy, lysosomal storage disorder, or peroxisomal disorder. In some examples, the subject has shown clinical signs of a disease of the eye.

In some examples, the subject has, or is at risk of developing a renal disease or complication. In some examples, the renal disease or complication is associated with AMD or aHUS. In some examples, the subject has, or is at risk of developing AMD or aHUS.

Clinical signs of a disease of the eye include, but are not limited to, decreased peripheral vision, decreased central (reading) vision, decreased night vision, loss of color perception, reduction in visual acuity, decreased photoreceptor function, and pigmentary changes. In one example, the subject shows degeneration of the outer nuclear layer (ONL). In another example, the subject has been diagnosed with a disease of the eye. In yet another example, the subject has not yet shown clinical signs of a disease of the eye.

As used herein, the terms "prevent", "preventing" and "prevention" refer to the prevention of the recurrence or onset of, or a reduction in one or more symptoms of a disease or condition (e.g., a disease of the eye) in a subject as result of the administration of a therapy (e.g., a prophylactic or therapeutic agent). For example, in the context of the administration of a therapy to a subject for an infection, "prevent", "preventing" and "prevention" refer to the inhibition or a reduction in the development or onset of a disease or condition (e.g., a disease of the eye), or the prevention of the recurrence, onset, or development of one or more symptoms of a disease or condition (e.g., a disease of the eye), in a subject resulting from the administration of a therapy (e.g., a prophylactic or therapeutic agent), or the administration of a combination of therapies (e.g., a combination of prophylactic or therapeutic agents). In some examples, prevention may refer to a result of administration of a polypeptide, as described herein, to a patient not having a disease or condition or not presenting with a sign or symptom of a disease or condition.

"Treating" a condition or patient refers to taking steps to obtain beneficial or desired results, including clinical results. With respect to a disease or condition (e.g., a disease of the eye), treatment refers to the reduction or amelioration of the progression, severity, and/or duration of an infection (e.g., a disease of the eye or symptoms associated therewith), or the amelioration of one or more symptoms resulting from the administration of one or more therapies (including, but not limited to, the administration of one or more prophylactic or therapeutic agents).

"Administering" or "administration of a substance, a compound or an agent to a subject can be carried out using one of a variety of methods known to those skilled in the art. For example, a compound or an agent can be administered intravitreally or subretinally. In particular examples, the compound or agent is administered intravitreally. In some examples, administration may be local. In other examples, administration may be systemic. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Each example described herein may be used individually or in combination with any other examples described herein.

The therapeutic compositions described herein may include one or more therapeutic peptides having proteoglycan binding activity that is equivalent or greater than the proteoglycan binding activity of CFH or FHL-1 and that confer improved complement inhibition and reduced apolipoprotein binding in the eye. For example, the therapeutic compositions described herein may include one or more therapeutic peptides that include human FHL-1 protein (e.g., SEQ ID NO: 2), and/or one or more engineered variants of FHL-1, such as any of those described in SEQ ID NO: 3-7, 11, 13, 17-137, IRV, IR, I, LKP, KP, or P (e.g., SEQ ID NO: 3, SEQ ID NO: 4, SEQ ID NO: 5, SEQ ID NO: 6, SEQ ID NO: 7, SEQ ID NO: 11, SEQ ID NO: 12, SEQ ID NO: 13, SEQ ID NO: 17 . . . . SEQ ID NO: 137). Thus, in some examples, described herein are therapeutic compositions of recombinant FHL-1, which may have an amino acid sequence similar or identical to native FHL-1 (e.g., SEQ ID NO: 2), and methods of using recombinant FHL-1 to treat a patient as described herein.

Figure 1B:
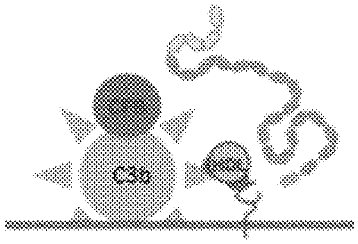
FIG. 1B schematically illustrates disruption of the proteoglycan binding activity when the CFH protein does not bind appropriately.
Figure 1C:
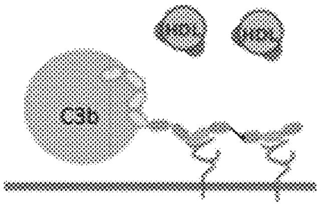
FIG. 1C schematically illustrates an example of an engineered variant of FHL-1 as described herein.

FIGS. 1A-1C schematically illustrate the therapeutic activity of the engineered variants described herein, and suggest a mechanism of how CFH or an engineered variant of CFH may regulate complement activation and lipid deposition in disease. In FIG. 1A ("normal" case) the proteoglycan binding activity of a CFH protein acts to localize CFH-mediated complement inhibition (CFH SCR 7 domain binding to proteoglycan) to ocular surfaces and blocks apolipoprotein binding (HDL). In some cases, e.g., during some forms of AMD, functional problems with a patient's CFH protein and/or in CFH expression or other functional defects may impair binding of the CFH protein to the proteoglycan, reducing complement inhibition at ocular surfaces and allowing apolipoproteins to accumulate, as shown in FIG. 1B. Without being bound to a particular theory, the methods and apparatuses described herein may include therapeutic proteins in which an engineered FHL-1 variant activity (which has been engineered for improved proteoglycan binding) confers improved complement inhibition at ocular surfaces and reduced apolipoprotein binding, as shown. This may result in a decrease of AMD symptoms and/or a reversal of the ill effect of AMD.

The engineered variants of FHL-1 described herein may be configured to have enhanced proteoglycan binding affinity/avidity, without significantly decreasing the permeability of the engineered variant of FHL-1 to Bruch's membrane in the eye, e.g., by limiting the molecular weight. The engineered variants of FHL-1 described herein may also be configured to reduce the risk of immunogenicity of the engineered variant of FHL-1.

Figure 2:
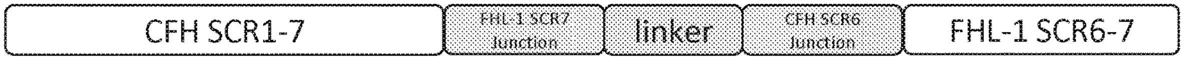
FIG. 2 schematically illustrates examples of arrangements of the therapeutic polypeptides as described herein (the therapeutic polypeptides shown in FIG. 2 may be referred to herein as engineered variants of FHL-1).

The engineered variants of FHL-1 may include one or more duplications of the $1^{st}$, $2^{nd}$, $3^{rd}$, $4^{th}$, $5^{th}$, $6^{th}$, $7^{th}$ short consensus repeats (SCRs) of CFH (referred to as SCR1, SCR2, SCR3, SCR4, SCR5, SCR6, and SCR7) or of FHL-1 (referred to as SCR6 and SCR7). Collectively, these regions may be referred to as CFH SCR1-7 (alternatively SCR1-7) or FHL-1 SCR6-7 (alternatively SCR6-7). These regions may all contribute to GAG binding activity and may be used in their entirety as a SCR1-7 unit. For example, in some variations the therapeutic polypeptides described herein may include, as shown in FIG. 2, a protein sequence that corresponds substantially to native FHL-1 (e.g., having 85% or greater identity, 90% or greater identity, 95% or greater identity, etc.) linked via a linker region (such as a Gly-Ser linker region or a poly-Ala linker region) to SCR1-7 or SCR6-7 units. Alternatively, the engineered FHL-1 variants, as shown in FIG. 2 could comprise a protein sequence that corresponds substantially to CFH (e.g., having 85% or greater identity, 90% or greater identity, 95% or greater identity, etc.) linked via a linker region (such as a Gly-Ser linker region) to SCR1-7 units. Although FIG. 2 shows an engineered variant of FHL-1 with FHL-1 (e.g., native FLH- 1), other engineered variants of FHL-1 may include other CFH or other splice variants of CFH. The therapeutic polypeptides shown in FIG. 2 may be referred to herein as engineered variants of FHL-1.

The linker region of FHL-1 variants described herein may include a linker with one or more junctions coupled thereto. A junction of the linker region may be coupled to the linker (e.g., the Gly-Ser or poly-Ala linker) between the linker and the CFH SCR1-7 unit. A junction of the linker region may be coupled to the linker (e.g., the Gly-Ser or poly-Ala linker) between the linker and the FHL-1 SCR6-7 unit. As shown in FIG. 2, the FHL-1 engineered variant may include a linker region having a linker between two junctions. In some examples, the junction may include an FHL-1 SCR7 junction coupled to the linker and the CFH SCR1-7 unit. Alternatively, the junction may include a CFH SCR6 junction coupled to the linker and the FHL-1 SCR6-7 unit. The linker region may include a peptide such as those described in SEQ ID NO: 4 to SEQ ID NO: 7, or SEQ ID NO: 11 to SEQ ID NO: 13, IRV, IR, I, LKP, KP, or P. In some examples, the linker region includes a combination of one or more peptides as described in SEQ ID NO: 4 to 7, or SEQ ID NO: 11 to SEQ ID NO: 13, IRV, IR, I, LKP, KP, or P. For example, the linker may include a junction peptide as described in SEQ ID NO: 4 to SEQ ID NO: 7, IRV, IR, or I coupled to the linker and the CFH SCR1-7 unit on the N-terminus. The linker may additionally or alternatively include a junction peptide as described in SEQ ID NO: 13 LKP, KP, or P coupled to the linker and the FHL-1 SCR6-7 unit on the C-terminus. The linker may also include a first junction peptide as described in SEQ ID NO: 4 to SEQ ID NO: 7, IRV, IR, or I coupled to the linker and the CFH SCR1-7 unit on the N-terminus and a junction peptide as described in SEQ ID NO: 13, LKP, KP, or P coupled to the linker and the FHL-1 SCR6-7 unit on the C-terminus.

Figure 3:
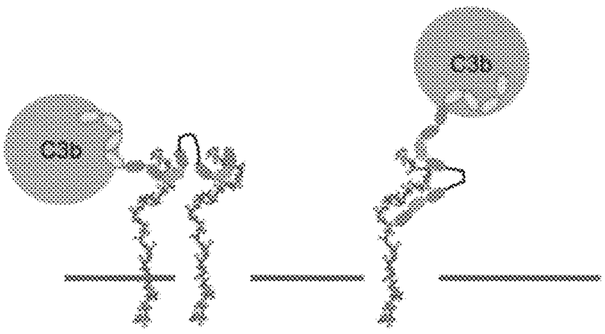
FIG. 3 schematically illustrates an example of an engineered variant of FHL-1 as described herein binding to surfaces via interaction with two adjacent proteoglycans or via interaction with a single proteoglycan.

Any appropriate linker region may be used as part of the engineered variants of FHL-1. For example, poly-Ala (e.g., AAA, $[EAAAK]_3$ (SEQ ID NO: 12)) or poly-GlySer linkers (e.g., $[GGGGS]_3$ (SEQ ID NO: 11), GGGGSGGGGSGGGGS (SEQ ID NO: 11), GGSGGSGGSGGS (SEQ ID NO: 148), GGGGSGGGGS (SEQ ID NO: 149), etc.) or poly-Gly linkers (e.g., GGG) may be used. The length of the linker may allow concurrent binding of multiple SCR domains, as described herein, to the cell surface glycosaminoglycans (GAGs). This is illustrated schematically in FIG. 3, showing how an engineered variant of FHL-1 may bind multiple GAGs simultaneously either by binding two different GAGs or by binding to the same GAG. As shown, the engineered variant of FHL-1 also includes a binding region to bind C3b. In some examples only a single binding region for C3b is included. In some examples, multiple C3b binding regions may be included (e.g., by including multiple repeats of SCRs). FIG. 3 illustrates two potential ways that a CFH variant with duplicated surface binding domains can function.

The engineered variants of FHL-1 described herein may generally have two or more tandem repeats of SCR6-7 units separated by a linker (e.g., GGGS (SEQ ID NO: 141), GGGGSGGGGS (SEQ ID NO: 149), GGGGSGGGGSGGGGS (SEQ ID NO: 11), etc.). The molecular weight of the engineered variants of FHL-1 may be between about 64 kDa and about 100.0 kDa.

Figure 4:
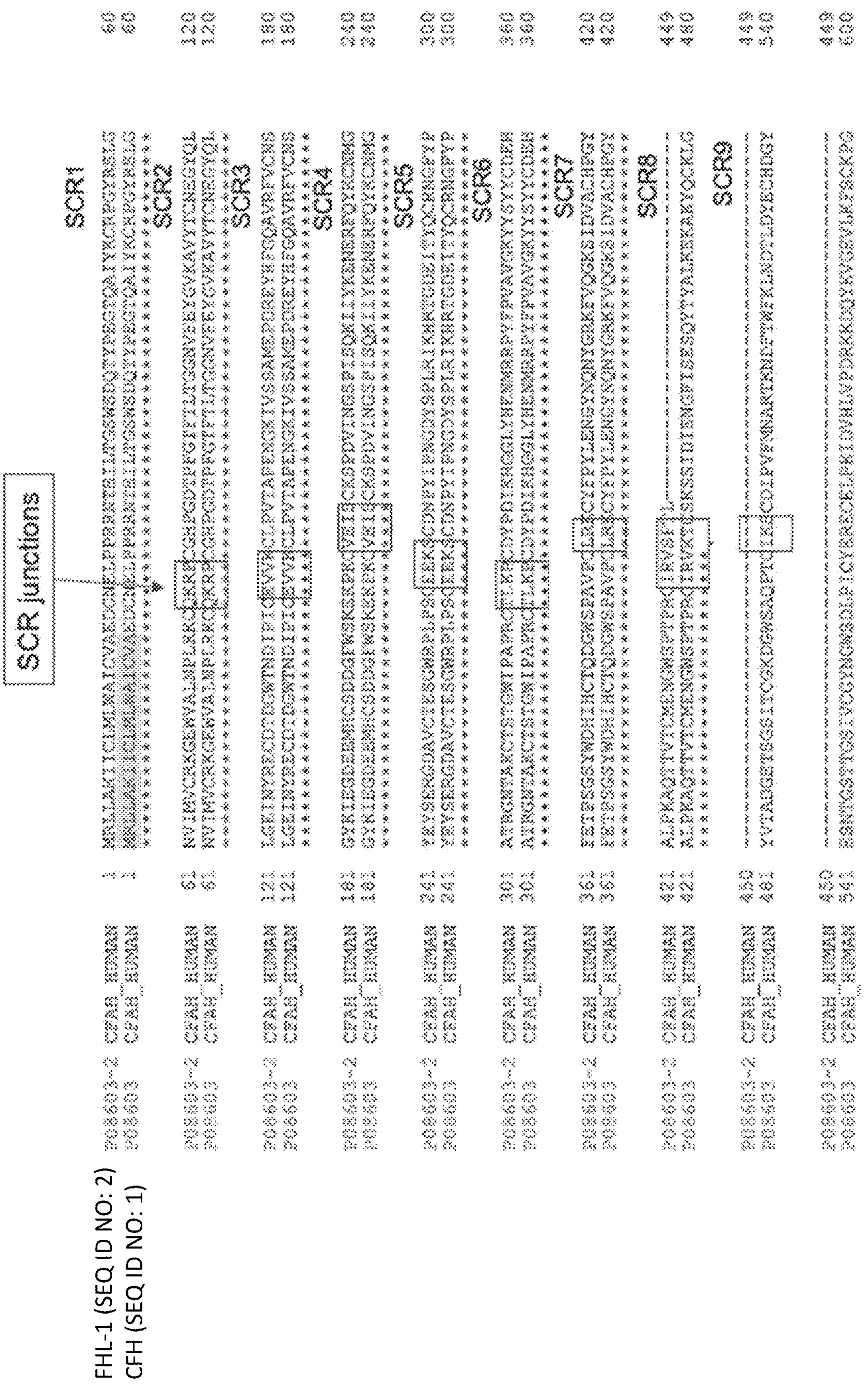
FIG. 4 shows an amino acid sequence alignment between human CFH and FHL-1.

FIG. 4 shows a sequence comparison of CFH (see SEQ ID NO: 1 and SEQ ID NO: 133) and FHL-1 (see SEQ ID NO: 2), illustrating the short consensus repeats (SCRs) as well as the SCR junction sequences between each of the short consensus repeats. The alignment of CFH and FHL-1 sequences in FIG. 4 includes examples of SCR1 to SCR9 domains (labeled as SCR1-SCR9). The sequences shown in FIG. 4 illustrate SCR junctions in the CFH and FHL-1 proteins (shown as boxed regions), and the unique C-terminal end of FHL-1 (SFTL), which were used in building the variant sequences described herein. The signal sequence (MRLLAKIICLMLWAICVA (SEQ ID NO: 150)) common to both CFH and FHL-1 is highlighted.

Figure 5:
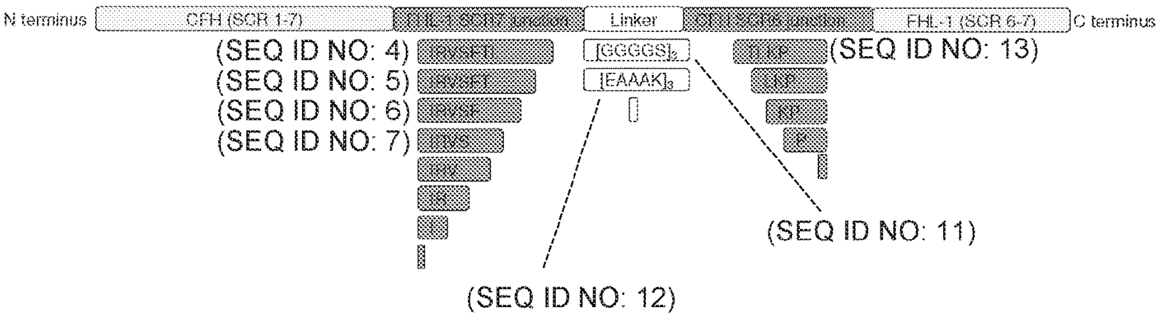
FIG. 5 schematically illustrates an example of a library of engineered variants of FHL-1 as described herein. Variants contain a constant region at the N-terminus comprised of the CFH SCR1-7 region, followed by 8 different variants of the FHL-1 SCR7 junction sequence, followed by 3 different variants of linker sequences, followed by 5 different variants of the CFH SCR6 junction sequence, followed by a constant region at the C terminus comprised of the FHL-1 SCR6-7 region.

FIG. 5 schematically illustrates other examples of engineered variants of FHL-1 as described herein. Variants may contain a constant region at the N-terminus comprised of the CFH SCR1-7 region, followed by variants of the FHL-1 SCR7 junction sequence, followed variants of linker sequences, followed by different variants of the CFH SCR6 junction sequence, followed by a constant region at the C terminus comprised of the FHL-1 SCR6-7 region. In some examples, as illustrated in FIG. 5, the therapeutic polypeptides described herein may include the linker. Alternatively, a subset of the peptide combinations described herein are void of a linker. The polypeptide may include the linker with a junction (e.g., FHL-1 SCR7 junction and CFH SCR6 junction). The schematic shown in FIG. 5 summarizes the matrix of variants tested to identify how to append additional surface-binding domain to FHL-1.

In some examples, the engineered variant of FHL-1 includes full length CFH SCR1-7 sequence (SCR1-7 or CFH), to which one additional FHL-1 SCR7 unit has been linked (e.g., SEQ ID. 98). For example, SEQ ID NO: 21 includes CFH SCR1-7 linked via a linker region including an FHL-1 SCR7 junction (e.g., SEQ ID NO: 7) and a GlySer linker (e.g., SEQ ID NO: 11) coupled to a CFH SCR6 junction (e.g., SEQ ID NO: 13) and then to an FHL-1 SCR 6-7 unit (e.g., SEQ ID NO: 17). SEQ ID NO: 37 includes CFH SCR1-7 linked via a linker region including an FHL-1 SCR7 junction (e.g., SEQ ID NO: 7) and a GlySer linker (e.g., SEQ ID NO: 11) coupled to a CFH SCR6 junction (e.g., LKP) and then to an FHL-1 SCR6-7 unit (e.g., SEQ ID NO: 17). The examples illustrated in FIG. 5. provide a library of combinations for peptides that may be included in the therapeutic polypeptide described herein. As described in the SEQ ID Nos. 1-7, 11-13, 17-137, IRV, IR, I, LKP, KP, or P, the polypeptide may include all of the peptide regions from the N-terminus to the C-terminus. Alternatively, therapeutic polypeptides described herein may include fewer than all of the peptide regions, as described herein from the N-terminus to the C-terminus.

All of these engineered variants may be expressed in a cell-based expression system (e.g., bacterial, insect, mammalian, etc.) in a soluble form, such as via transient CHO expression. The therapeutic peptides (e.g., FHL-1 engineered variants) described herein may be produced in any appropriate protein expression system, including cell-based or in vitro expression systems.

Figure 6:
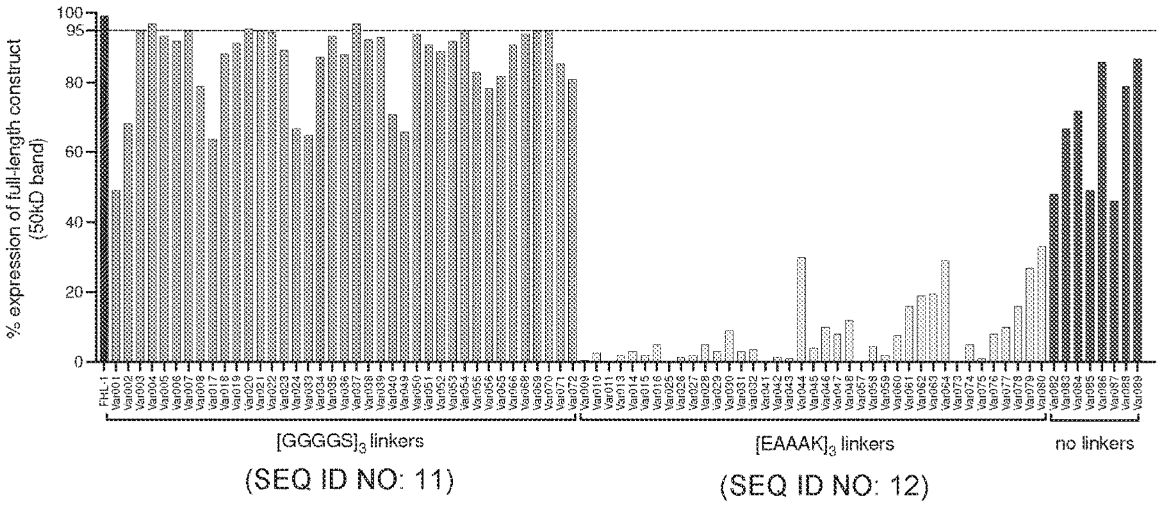
FIG. 6 is a bar graph showing the amount of full-length proteins expressed from a library of engineered variants of FHL-1, as measured by western blot analysis (anti-CFH antibody).

The FHL-1 engineered variants may be engineered to include a linker, as described herein, based on resulting protein integrity. Analysis of protein integrity was considered and is illustrated in FIG. 6 showing examples of the FHL-1 engineered variants and their relative expression of full-length versus truncated protein as measured by western blot analysis. Here, FHL-1 engineered variant sequences were cloned into pcDNA3.1 (+) vector and transiently expressed using expi-CHO Expression System at 0.8 mL scale in 96-well culture format. Culture supernatants were collected at day 7 post-transfection. Protein expression and integrity was analyzed by western blot with anti-CFH antibody. An amount of full-length protein was represented by the intensity of bands at 50 kDa, while truncated proteins were represented by the combined intensities of bands at 38 kDa and 35 kDa. Percent full-length protein is represented as: Intensity of 50 kDa band divided by the sum of the 50 kDa, 38 kDa and 35 kDa bands, multiplied by 100. In some examples, FHL-1 engineered variants may have different protein integrity. For example, variants containing a poly-Ala linkers (e.g., $[EAAAK]_3$ (SEQ ID NO: 12) linker) may have lower protein integrity relative to variants with GlySer linkers (e.g., $[GGGGS]_3$ (SEQ ID NO: 11) linker) or no linker. FIG. 6 illustrates one example of a functional screen that identifies variant sequences that result in high levels of intact protein expression. In this example, constructs with GlySer linkers produced higher levels of intact protein than constructs with EAAAK (SEQ ID NO: 145) linkers, or no linkers.

Figure 7A:
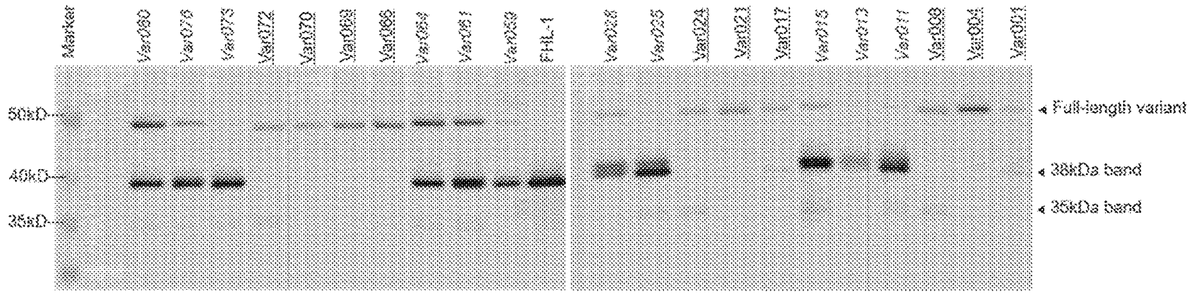
FIGS. 7A and 7B are examples of representative sets of western blots showing FHL-1 and engineered FHL-1 variants expressed using a CHO expression system.
Figure 7B:
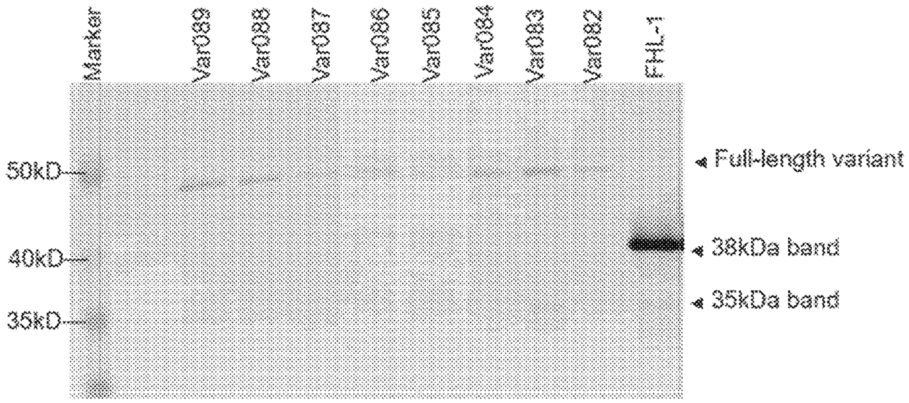

FIGS. 7A and 7B illustrate transient expression of representative FHL-1 engineered variants, as described herein. This data shows that GlySer linker constructs (underlined) result in expression of largely intact proteins. Here, FHL-1 variant sequences were cloned into pcDNA3.1 (+) vector and transiently expressed using expi-CHO Expression System standard protocols at 0.8 mL scale in 96-well culture format. Culture supernatants were collected at day 7 post-transfection. Culture supernatants were analyzed by non-reducing SDS-PAGE using 4-12% Bis-Tris gel. Protein expression and integrity was analyzed by western blot with anti-CFH antibody (e.g., clone OX-23). The amount of full-length protein was represented by the intensity of bands at 50 kDa, while truncated proteins were represented by the combined intensities of bands at 38 kDa and 35 kDa. FIG. 7A shows subset of variants with a GlySer linker and poly-Ala linker (e.g., SEQ ID NO: 97, SEQ ID NO: 93, SEQ ID NO: 90, SEQ ID NO: 89, SEQ ID NO: 87, SEQ ID NO: 86, SEQ ID NO: 83, SEQ ID NO: 81, SEQ ID NO: 78, SEQ ID NO: 76, SEQ ID NO: 45, SEQ ID NO: 42, SEQ ID NO: 41, SEQ ID NO: 38, SEQ ID NO: 34, SEQ ID NO: 32, SEQ ID NO: 30, SEQ ID NO: 28, SEQ ID NO: 25, SEQ ID NO: 21, and SEQ ID NO: 18). Variants with GlySer linker are underlined, and variants with poly-Ala linkers are italicized. FIG. 7B shows expression of representative engineered variants, as described herein, with no linker sequence (e.g., SEQ ID. No. 106 to SEQ ID NO: 99).

Figure 8A:
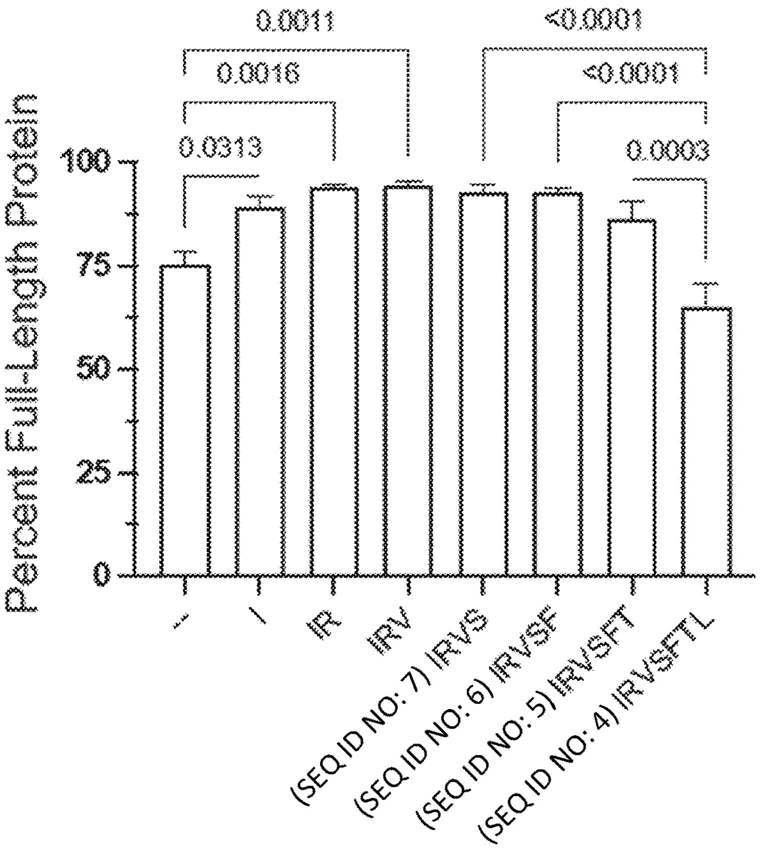
FIGS. 8A and 8B are bar graphs showing the amount of full-length protein expressed at day 7 post-transfection for a subset of engineered variants of FHL-1 that contain $[GGGGS]_3$ (SEQ ID NO: 11) linkers, as measured by western blot analysis (anti-CFH antibody).
Figure 8B:
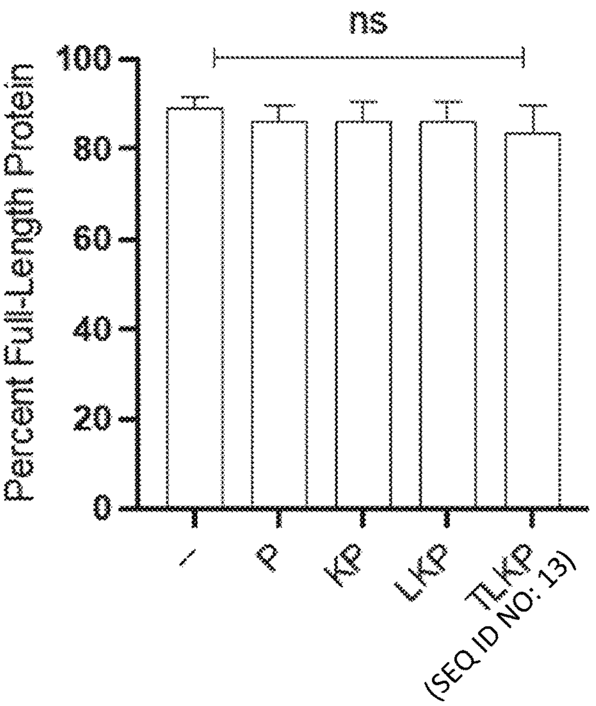

Junctions of the linker region (e.g., FHL-1 SCR7 and CFH SCR6) were considered for their impact on protein integrity. FIGS. 8A and 8B illustrate the results showing the amount of full-length protein expressed at day 7 post-transfection for a subset of engineered variants of FHL-1 that contain GlySer linkers, as measured by western blot analysis (anti-CFH antibody). In particular, representative FHL-1 constructs including the GlySer linker were transiently expressed using expi-CHO Expression System using standard protocols at 0.8 mL scale in 96-well culture format. Culture supernatants were collected at day 7 post-transfection. Protein integrity was analyzed by western blot with anti-CFH antibody (clone OX-23). The amount of full-length protein was represented by the intensity of bands at 50 kDa, while truncated proteins were represented by the combined intensities of bands at 38 kDa and 35 kDa. Percent full-length protein is represented as: Intensity of 50 kDa band divided by the sum of the 50 kDa, 38 kDa and 35 kDa bands, multiplied by 100. FIG. 8A illustrates a comparison of examples of FHL-1 engineered variants containing the same FHL-1 SCR7 junction sequence. FIG. 8B illustrates a comparison of examples of FHL-1 engineered variants containing the same CFH SCR6 junction sequence. The graphs for both FIGS. 8A and 8B show mean values+/−SEM for variant sets containing the same FHL-1 SCR7 or CFH SCR6 junction sequence (n=5 per group except for IRVSF (SEQ ID NO: 6)=4). As shown, sequence analysis identified which SCR7 junction sequences result in better protein integrity of expressed constructs; all tested SCR6 junction sequences had similar expression integrity. Differences between groups were analyzed with one-way ANOVA and Tukey's multiple comparisons test. Of note, the engineered FHL-1 variants with FHL-1 SCR7 junctions comprised of I, IR, IRV, IRVS (SEQ ID NO: 7), IRVSF (SEQ ID NO: 6) or IRVSFT (SEQ ID NO: 5) may have significantly higher protein integrity relative to variants with FHL-1 SCR7 junctions comprised of either IRVSFTL (SEQ ID NO: 4) or no SCR7 junction sequence. No significant differences in protein integrity were observed for any of the CFH SCR6 junction sequences tested.

Figure 9:
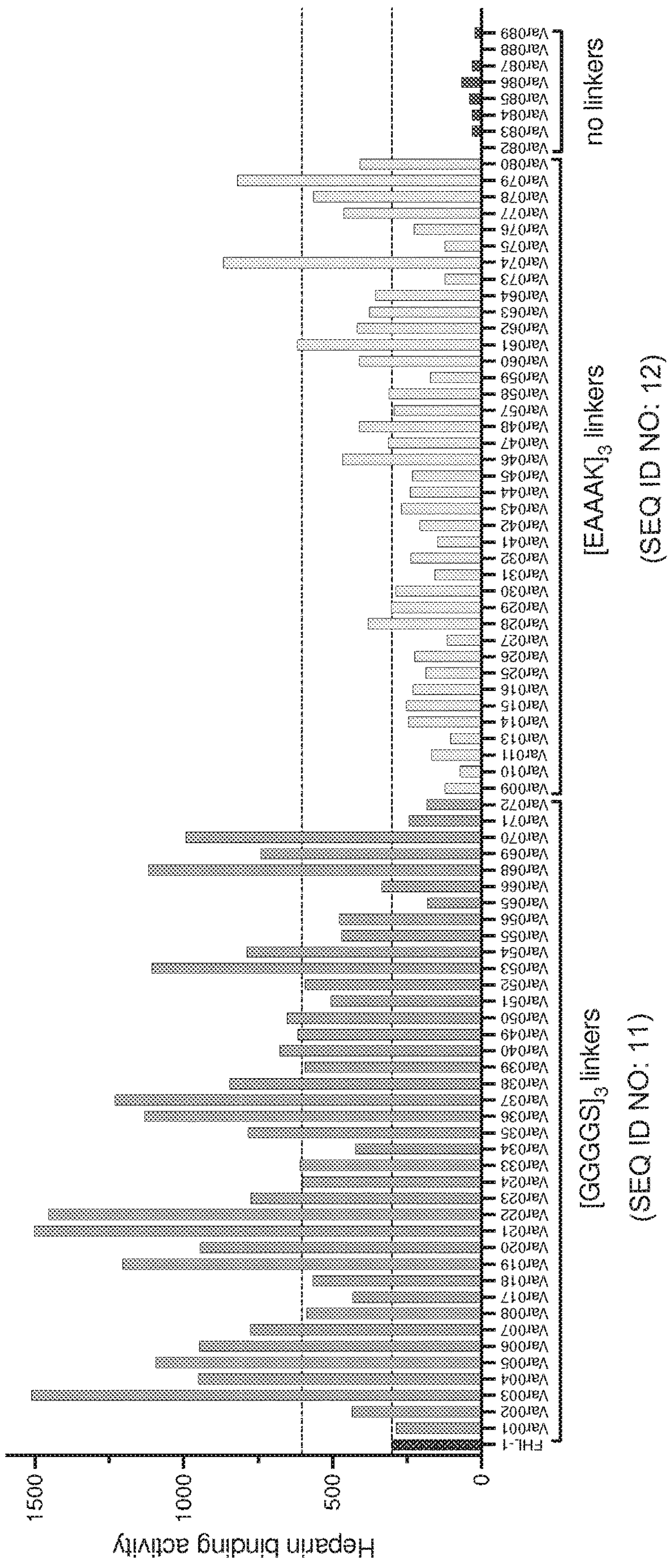
FIG. 9 is a bar graph showing the heparin binding activity of proteins expressed from a library of engineered variants of FHL-1, as measured by ELISA.

The linker of FHL-1 engineered variants described herein may impact heparin binding activity. FIG. 9 illustrates heparin binding activity of representative FHL-1 engineered variants. Many constructs with GlySer linkers show over 2× improved heparin binding activity compared to constructs with poly-Ala linkers or no linkers. Some EAAAK (SEQ ID NO: 145) linker constructs also show improved heparin binding activity, while none of the linker-less constructs performed well in this assay. For example, FHL-1 variant sequences were cloned into pcDNA3.1 (+) vector and transiently expressed using expi-CHO Expression System standard protocol at 0.8 mL scale in 96-well culture format. Culture supernatants were collected at day 7 post-transfection and tested in a heparin binding ELISA. For each construct, 50 μL of expression culture was incubated on a heparin-coated plate, along with a reference standard of 0-2000 nM purified FHL-1 protein. Heparin binding activity was measured by mouse anti-CFH antibody (e.g., OX23), followed by HRP-conjugated anti-mouse secondary, and readout via TMB substrate. The graph in FIG. 9 depicts mean FHL-1 molar equivalents of bound protein for each expression construct. The dashed lines indicate 100% and 200% values for FHL-1 native sequence construct. Of note, some examples of FHL-1 engineered variants containing GlySer linkers may have increased heparin binding activity relative to variants containing poly-Ala linkers or no linker.

Figure 10A:
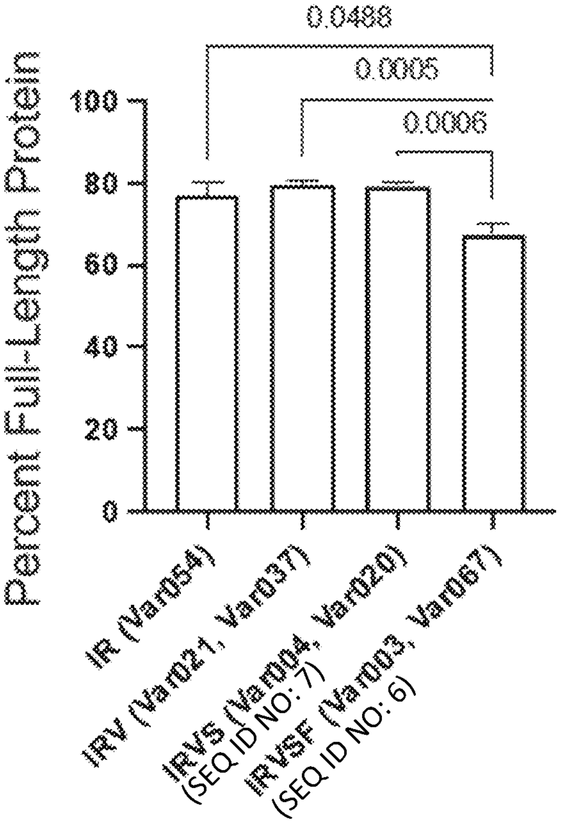
FIG. 10A is a bar graph showing the amount of full-length protein expressed at day 13 post-transfection for a subset of engineered variants of FHL-1 that contain $[GGGGS]_3$ (SEQ ID NO: 11) linkers, as measured by western blot analysis (anti-CFH antibody). Sets of variants containing the same FHL-1 SCR7 junction sequence are compared.
Figure 10B:
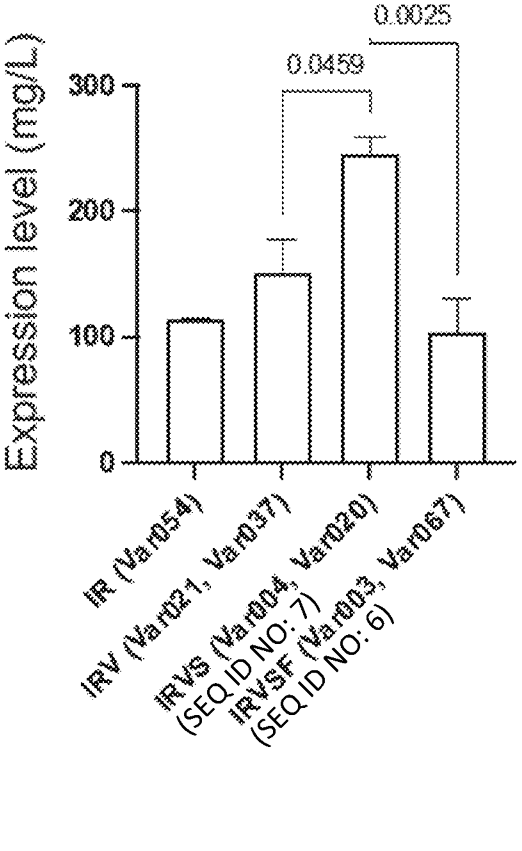
FIG. 10B is a bar graph showing the total amount of protein expressed at day 13 post-transfection for a subset of engineered variants of FHL-1 that contain $[GGGGS]_3$ (SEQ ID NO: 11) linkers, as measured by interpolation of western blot band intensity against a reference standard of purified FHL-1 protein. Sets of variants containing the same FHL-1 SCR7 junction sequence are compared.

The FHL-1 engineered variants described herein may exhibit differences in protein integrity and expression level. FIGS. 10A and 10B are graphs representing data showing full-length protein integrity and expression levels of representative examples of FHL-1 engineered variants containing GlySer linkers and different FHL-1 SCR7 junction sequences. The graphs of FIGS. 10A and 10B illustrate data from FHL-1 variant sequences for 7 constructs that were transiently expressed using expi-CHO Expression System high titer protocol at 0.8 mL scale in 96-well culture format. The culture supernatants were collected at day 13 post-transfection. This is a similar analysis as shown in FIG. 8, but using replicates of a selected number of top hits from the initial screen, and expressing them for a longer period of time. This test shows that IRVS (SEQ ID NO: 7) sequence of the SCR7 junction is preferable over other junctions in terms of optimizing expression levels and the integrity of the construct.

FIG. 10A is a bar graph showing the amount of full-length protein expressed at day 13 post-transfection for a subset of engineered variants of FHL-1 that contain GlySer linkers and different FHL-1 SCR7 junction sequences, as measured by western blot analysis. For example, variants represented by FIG. 10A include comparisons of sets of variants containing the same FHL-1 SCR7 junction sequence (e.g., SEQ ID No.71 vs SEQ ID NO: 28/SEQ ID NO: 54 vs SEQ ID NO: 21/SEQ ID NO: 37 vs SEQ ID NO: 20/SEQ ID NO: 84. Protein integrity was analyzed by western blot with anti-CFH antibody (e.g., clone OX-23). The amount of full-length protein was represented by the intensity of bands at 50 kDa, while truncated proteins were represented by the combined intensities of bands at 38 kDa and 35 kDa. Percent full-length protein is represented as: Intensity of 50 kDa band divided by the sum of the 50 kDa, 38 kDa and 35 kDa bands, multiplied by 100. The graph in FIG. 10A shows mean values+/−SEM of groups of constructs with common FHL-1 SCR7 junction sequences. Of note variants with FHL-1 SCR7 junctions comprised of IR, IRV or IRVS (SEQ ID NO: 7) may have significantly higher protein integrity relative to variants with FHL-1 SCR7 junction comprised of IRVSF (SEQ ID NO: 6) sequence.

FIG. 10B is a bar graph showing the amount of protein expressed at day 13 post-transfection for the subset of engineered variants of FHL-1 that contain GlySer linkers and different FHL-1 SCR7 junction sequences, as measured by interpolation of western blot band intensity against a reference standard of purified FHL-1 protein. FIG. 10B, expression level of different constructs was measured by western blot (e.g., OX-23 antibody). Intensity of monomer bands was interpolated against a reference standard of purified FHL-1 protein. Of note variants with FHL-1 SCR7 junctions comprised of IRVS (SEQ ID NO: 7) may have significantly higher protein expression levels relative to variants with FHL-1 SCR7 junction comprised of IR, IRV or IRVSF (SEQ ID NO: 6).

Figure 11A:
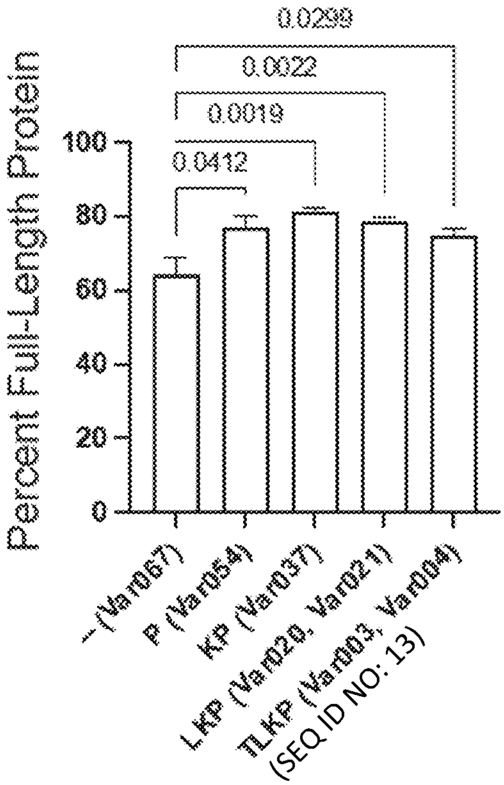
FIG. 11A is a bar graph showing the amount of full-length protein expressed at day 13 post-transfection for a subset of engineered variants of FHL-1 that contain $[GGGGS]_3$ (SEQ ID NO: 11) linkers, as measured by western blot analysis (anti-CFH antibody). Sets of variants containing the same CFH SCR6 junction sequence are compared.
Figure 11B:
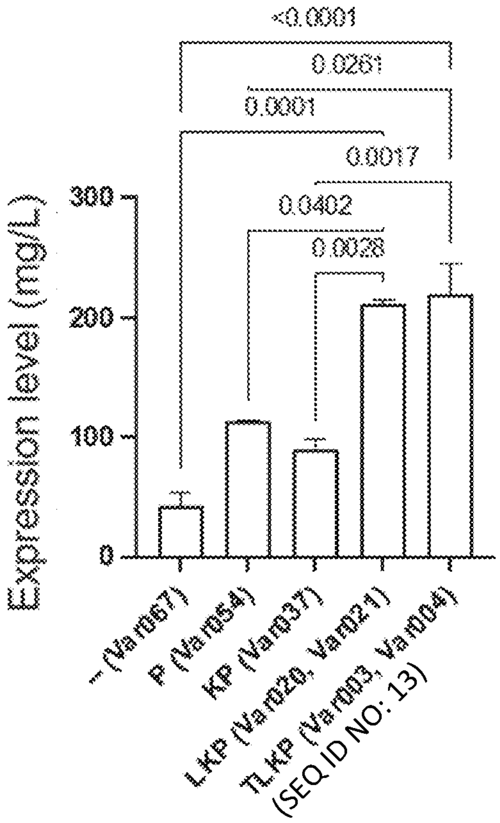
FIG. 11B is a bar graph showing the total amount of protein expressed at day 13 post-transfection for a subset of engineered variants of FHL-1 that contain $[GGGGS]_3$ (SEQ ID NO: 11) linkers, as measured by interpolation of western blot band intensity against a reference standard of purified FHL-1 protein. Sets of variants containing the same CFH SCR6 junction sequence are compared.

FIGS. 11A and 11B are graphs representing data showing full-length protein integrity and expression levels of representative examples of FHL-1 engineered variants containing GlySer linkers and different CFH SCR6 junction sequences. The FHL-1 variant sequences for 7 constructs containing GlySer linkers were transiently expressed (n=3 per construct) using expi-CHO Expression System high titer protocol at 0.8 mL scale in 96-well culture format. Culture supernatants were collected at day 13 post-transfection for the variants in both FIGS. 11A and 11B. This is a similar analysis as shown in FIG. 8, but using replicates of a selected number of top hits from the initial screen, and expressing them for a longer period of time. This test revealed that LKP and TLKP (SEQ ID NO: 13) sequences for the SCR6 junction confer more optimal levels of expression of full length construct.

FIG. 11A is a bar graph showing the amount of full-length protein expressed at day 13 post-transfection for a subset of engineered variants of FHL-1 that contain GlySer linkers and different CFH SCR6 junction sequences, as measured by western blot analysis. For example, variants represented by FIG. 11A include comparisons of sets of variants containing the same CFH SCR6 junction sequence (e.g., SEQ ID No. 84 vs SEQ ID NO: 71 vs SEQ ID NO: 54 vs SEQ ID NO: 37/SEQ ID NO: 38 vs SEQ ID NO: 20/SEQ ID NO: 21). The protein integrity was analyzed by western blot with anti-CFH antibody (e.g., clone OX-23). The amount of full-length protein was represented by the intensity of bands at 50 kDa, while truncated proteins were represented by the combined intensities of bands at 38 kDa and 35 kDa. Percent full-length protein is represented as: Intensity of 50 kDa band divided by the sum of the 50 kDa, 38 kDa and 35 kDa bands, multiplied by 100. The graph shows mean values+/−SEM of groups. Differences between groups were analyzed with one-way ANOVA and Tukey's multiple comparisons test. Of note, variants with CFH SCR6 junctions comprised of P, KP, LKP or TLKP (SEQ ID NO: 13) had significantly higher protein integrity relative to variants with CFH SCR6 junction comprised of no sequence.

FIG. 11B is a bar graph showing the amount of protein expressed at day 13 post-transfection for a subset of engineered variants of FHL-1 that contain GlySer linkers and different CFH SCR6 junction sequences, as measured by interpolation of WB band intensity against a reference standard of purified FHL-1 protein. Sets of variants containing the same CFH SCR6 junction sequence were compared. Of note, variants with CFH SCR6 junction sequences comprised of LKP or TLKP (SEQ ID NO: 13) have significantly higher levels of protein expression compared to variants with junction sequences P, KP, or no sequence.

The table in FIG. 12 summarizes results of examples of protein expression of representative FHL-1 engineered variants with GlySer linkers relating to the junctions of the linker region. For example, an optimal junction may confer significantly improved properties. Out of a matrix of 8 SCR7 junction sequences, and 5 SCR6 junction sequences tested (40 variants), two combinations were identified as more optimal sequences: IRVS (SEQ ID NO: 7)+LKP (Var020), and IRVS (SEQ ID NO: 7)+TLKP (SEQ ID NO: 13) (Var004). As presented in FIG. 12, the FHL-1 SCR7 junction may be optimal in FHL-1 engineered constructs with SEQ ID NO: 7 (e.g., IRVS (SEQ ID NO:7)). FHL-1 engineered constructs including CFH SCR6 junctions of SEQ ID NO: 13 and LKP may be optimal as a linker junction of the polypeptide, as discussed above in FIGS. 8, 10A, 10B, 11A and 11B, SEQ ID NO: 21 (e.g., Var004) and SEQ ID NO: 37 (e.g., Var020). In some examples, the linker junction may comprise a combination of a linker and one or more junctions based on the significantly improved properties. In some examples, an optimal linker junction may comprise a combination of a peptide of SEQ ID NO: 11 coupled to a peptide of SEQ ID NO: 7 and SEQ ID NO: 13. In some examples, an optimal linker junction may comprise a combination of a peptide of SEQ ID NO: 11 coupled to a peptide of SEQ ID NO: 7 and LKP. In some examples, the optimal linker junction may comprise a combination of any of the peptide sequences described herein.

Any of the therapeutic polypeptides described herein may be assayed and/or functionally characterized to show that they have either or both GAG and C3b binding properties sufficient to localize the complement inhibition to ocular surfaces and to block apolipoprotein binding (HDL). For example, the therapeutic polypeptide described herein may be shown via one or more assays to bind either or both C3b and GAG, including showing C3b and GAG binding kinetics, such as by ELISA. In general, such assays may be used to confirm that the binding kinetics to C3b and GAG of the therapeutic polypeptide (e.g., recombinant FHL-1 or an FHL-1 engineered variant) are similar or better than those of native CFH and/or FHL-1.

Figures 13A, 13B:
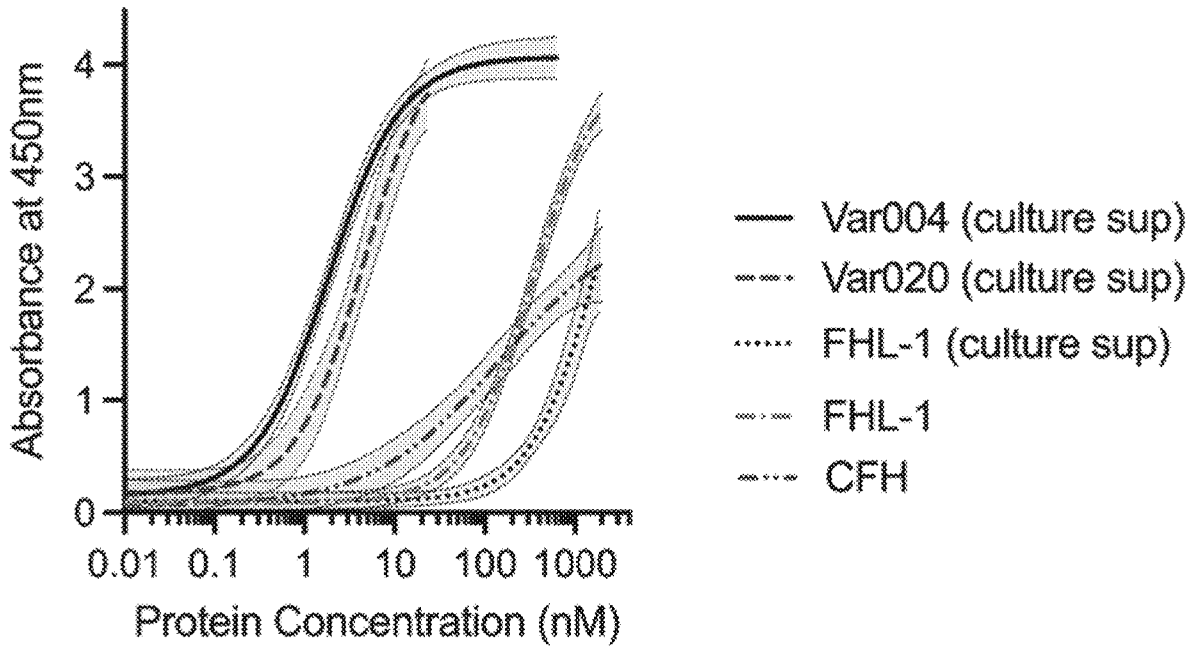
FIGS. 13A and 13B illustrate the binding activity of engineered variants of FHL-1 (e.g., Var004, Var020) and control proteins (e.g., FHL-1, CFH) to heparin, as measured by ELISA. The graph shows mean absorbance values from multiple independent heparin-binding assays. The table summarizes the EC50 values across multiple experiments.

In FIGS. 13A and 13B, heparin binding affinity was measured via ELISA for purified CFH, purified FHL-1 and culture supernatants (culture sup) from CHO cells transfected with FHL-1 or representative examples of FHL-1 engineered variant constructs harvested after 8 days of expression at 30 mL scale. Analytes were incubated on heparin-coated plates, and FH/variant binding measured via anti-CFH (clone OX-23) antibody, and HRP-conjugated anti-mouse secondary antibody. Signals were detected via incubation with TMB substrate. EC50 values were measured by 4PL nonlinear regression. FIG. 13A shows mean regression fit and 95% confidence intervals of assay absorbance values from 25 independent assays. The table in FIG. 13 B summarizes the EC50 values across multiple experiments.

Of note, FHL-1 engineered variants of SEQ ID NO: 21 and 37 have improved heparin binding activity relative to FHL-1 or CFH, and the polypeptide of SEQ ID NO: 21 was found to have increased heparin binding activity compared to the polypeptide of SEQ ID NO: 37. The results of the assay shown in FIGS. 13A-13B suggest that the Var004 sequence has superior heparin binding activity compared to Var020.

Figures 14A, 14B:
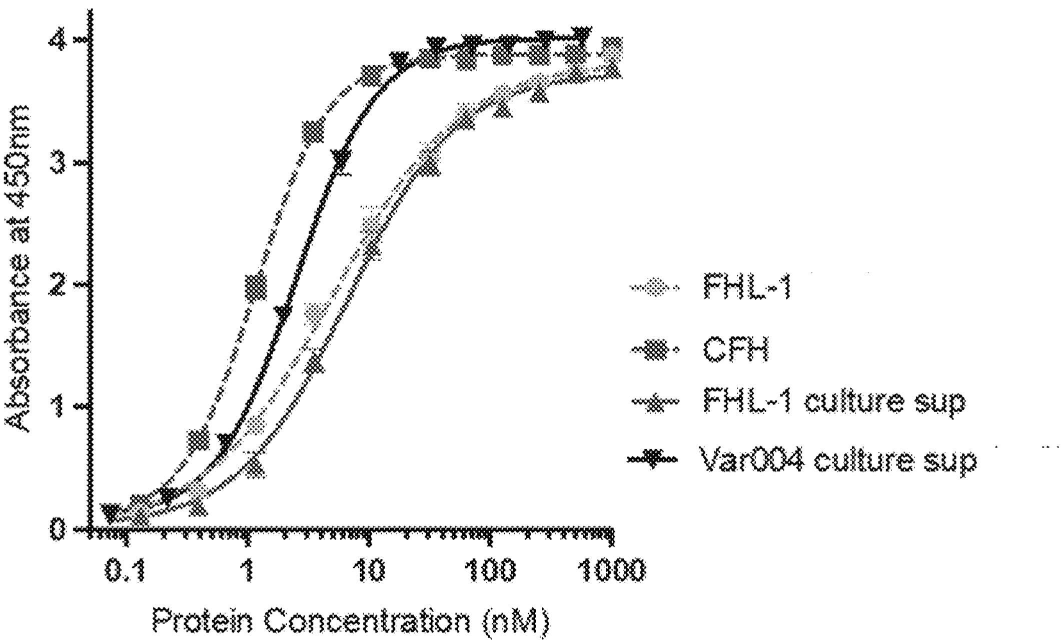
FIGS. 14A and 14B illustrate the binding activity of an engineered variant of FHL-1 (e.g., Var004) and control proteins (e.g., FHL-1, CFH) to C3b, as measured by ELISA. The graph shows mean absorbance values from multiple independent C3b-binding assays. The table summarizes the EC50 values across multiple experiments.

A representative example of an FHL-1 engineered variant (e.g., a polypeptide of SEQ ID NO: 21) was compared with CFH and FHL-1 for C3b binding activity as presented in FIGS. 14A and 14B. The graph in FIG. 14A shows mean absorbance values from multiple independent C3b-binding assays, and the table in FIG. 14B summarizes the EC50 values across multiple experiments. In general, the data was derived from measuring binding on C3b coated plates via ELISA for test proteins (either as purified proteins or as culture supernatants from CHO cells transfected with expression vectors encoding test proteins). C3b binding activity was measured via absorbance at 450 nM. Mean+/−SEM absorbance values are shown with nonlinear sigmoidal 4PL fit. Of note, the FHL-1 engineered variant (e.g., Var 004, SEQ ID NO: 21) has increased C3b binding activity over native FHL-1. FIGS. 14A-14B show that the Var004 construct did not compromise C3b binding activity compared to control proteins.

Figure 15:
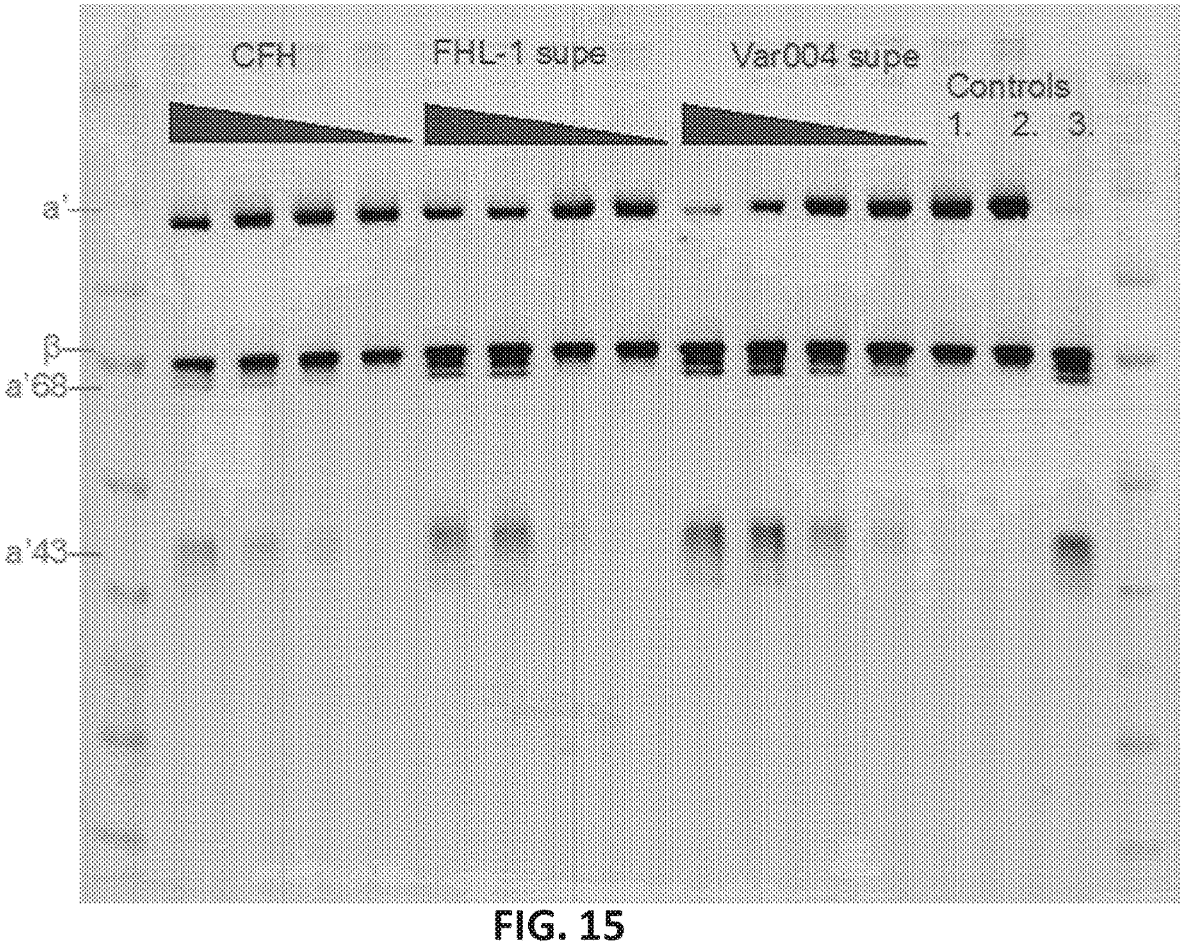
FIG. 15 is an example of a representative western blot (anti-C3b antibody) showing surface-dependent complement inhibitory activity of an engineered variant of FHL-1 (e.g., Var004) and control proteins (e.g., FHL-1, CFH). Bands labeled a' and β indicate intact C3b bands at 130 kDa and 70 kDa, respectively. Bands labeled a'68 and a'43 indicate cleaved forms of C3b (iC3b) at 68 kDa and 43 kDa, respectively. Lanes labeled CFH, FHL-1 supe and Var004 supe contain decreasing amounts of each protein in each set (333 nM, 111 nM, 37 nM, 12.3 nM). Control lane 1 contains cells, conditioned media, C3b and CFI. Control lane 2 contains C3b and CFI. Control lane 3 contains C3b, CFI and CFH.

Western blot analysis, as shown in FIG. 15 was performed using anti-C3b antibodies showing surface-dependent complement inhibitory activity of an engineered variant of FHL-1 (e.g., Var004, SEQ ID NO: 21) and control proteins FHL-1 and CFH). 2 million expi-CHO cells/test were resuspended in PBS with [12.3 nM, 37 nM, 111 nM, or 333 nM] purified CFH, FHL-1 culture sup, or FHL-1 engineered variant (e.g., Var004) culture sup. Control lane 1 contains cells, conditioned media, C3b and CFI. Control lane 2 contains C3b and CFI. Control lane 3 contains C3b, CFI and CFH. FH/variant binding was performed at 37 C for 30 minutes. Cells were then thoroughly washed and resuspended in PBS with 0.5 μg C3b and 1.5 μg CFI per test. Cell/C3b/CFI mixtures were incubated at 37 C for 15 minutes. Reaction supernatants were then analyzed by reducing SDS-PAGE, and C3b degradation monitored by anti-C3b Western. Four C3b bands were quantified: C3b a' (~130 kDa), C3b B (70 kDa), iC3b a' (68 kDa) and iC3b a' (43 kDa). The representative FHL-1 engineered variant has higher surface-dependent complement inhibitory activity relative to FHL-1 and CFH, as evidenced by the increased accumulation of C3b degradation products.

Figure 16:
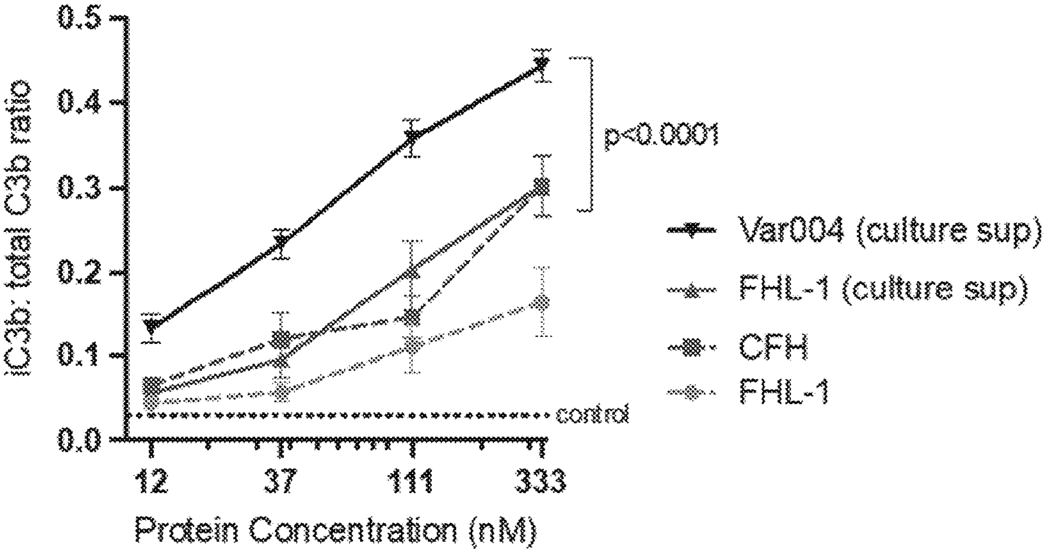
FIG. 16 illustrates examples of the surface-dependent complement inhibitory activity of an engineered variant of FHL-1 (e.g., Var004) and control proteins (FHL-1, CFH), as measured by western blot analysis (anti-C3b antibody). Activity is expressed as the ratio of iC3b to total C3b produced at each protein concentration tested, as measured by the intensity of bands representing intact and cleaved C3b: [a'68+a'43]/[a'68+a'43+a'+β].

FIG. 16 illustrates the surface-dependent complement inhibitory activity of a representative FHL-1 engineered variant (e.g., Var004/SEQ ID NO: 21) and control proteins FHL-1 and CFH, as measured by western blot analysis using anti-C3b antibody. Activity is expressed as the ratio of iC3b to total C3b produced at each protein concentration tested, as measured by the intensity of bands representing intact and cleaved C3b: [a'68+a'43]/[a'68+a'43+a'+β]. 2 million expi-CHO cells/test were resuspended in PBS with [0, 12.3 nM, 37 nM, 111 nM, or 333 nM] purified CFH, FHL-1 CHO culture sup, or FHL-1 engineered variant (e.g., Var004) CHO culture sup. Conditioned CHO media was used as a negative control for the FHL-1 engineered variant and FHL-1 culture sups. FH/variant binding was performed at 37 C for 30 minutes. Cells were then thoroughly washed and resuspended in PBS with 0.5 μg C3b and 1.5 μg CFI/test. Cell/C3b/CFI mixtures were incubated at 37 C for 15 minutes. Reaction supernatants were then analyzed by reducing SDS-PAGE, and C3b degradation monitored by anti-C3b Western. Four C3b bands were quantified: C3b a' (~130 kDa), C3b β (70 kDa), iC3b a' (68 kDa) and iC3b a' (43 kDa). Graphs indicate mean±/−SEM from 4 independent experiments. Differences between groups analyzed by two-way ANOVA with Tukey's multiple comparisons. Ratio of iC3b/total C3b was calculated by dividing sum intensity of a'68+a'43 bands against the sum intensity of a'68, a'43, a' (~130 kDa) and β (70 kDa) bands. The representative FHL-1 engineered variant has higher surface-dependent complement inhibitory activity relative to FHL-1 and CFH, as evidenced by the increased generation of C3b degradation products. FIGS. 15 and 16 demonstrate improved surface-dependent complement inhibitory activity by Var004; this was a key design feature intended by the screening campaign. Complement inhibition is measured by ability of the construct to act as a cofactor for CFI to promote cleavage of C3b into iC3b.

The therapeutic polypeptides examined in FIGS. 13A-16 were examples of FHL-1 engineered variant polypeptides for use as described herein may display similar or better characteristics according to these assays.

Figure 17A:
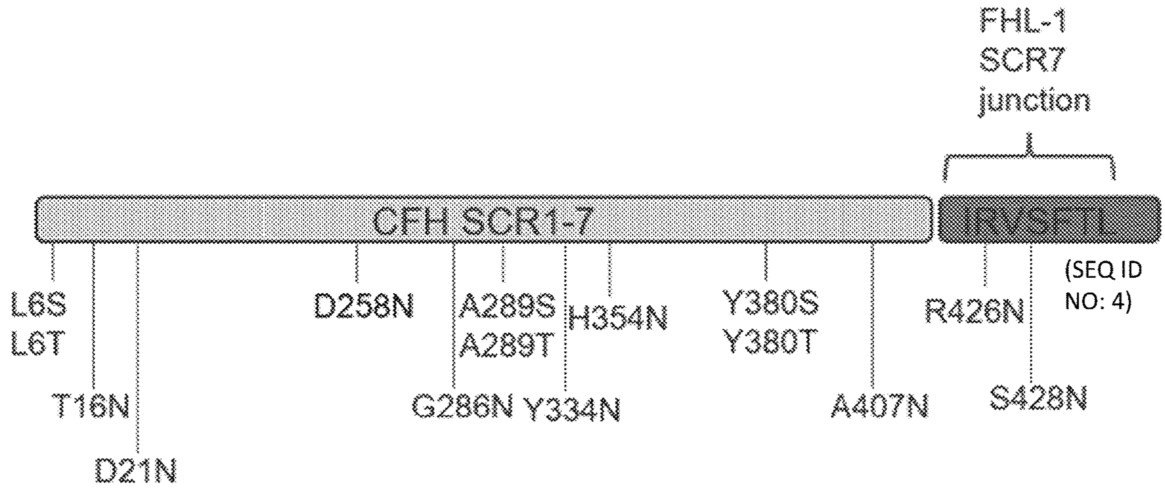
FIGS. 17A and 17B schematically illustrate examples of libraries of glycoengineered variants of FHL-1 as described herein. Each amino acid substitution introduces an N-linked glycosylation motif (NxS/T).
Figure 17B:
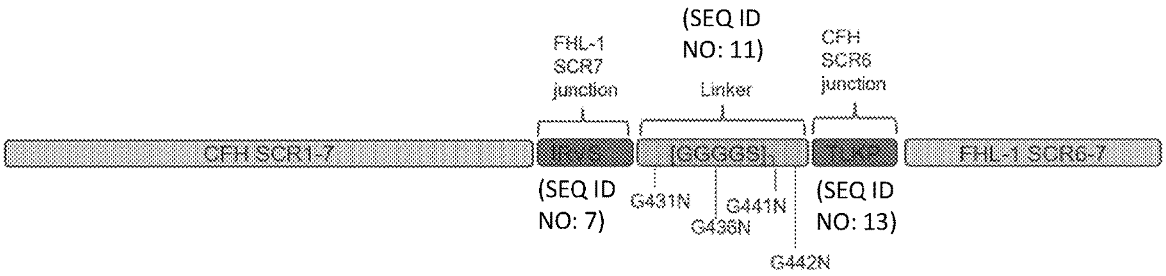

The therapeutic polypeptides (e.g., FHL-1 engineered variants), as described herein, may be glycoengineered variants of FHL-1 having one or more amino acid (AA) substitutions. Some examples of representative amino acid substitutions are presented in FIGS. 17A and 17B illustrating a library of AA substitutions within the CFH SCR1-7 region, the FHL-1 SCR7 junction region and the GlySer linker region. Thus, FIGS. 17A-17B illustrate a glycoengineering strategy to identify point mutations that produce effective glycosylation within either FHL-1 or within the GlySer linker sequence. For example, 15 variants of the FHL-1 SCR1-7 framework contain single amino acid substitutions at positions L6S, L6T, T16N, D21N, D258N, G286N, A289S, A289T, Y334N, H354N, Y380S, Y380T, A407N, R426N and S428N. As a representative example, four variants of the FHL-1 engineered variant of SEQ ID NO: 21 framework contain single amino acid substitutions at positions G431N, G436N, G441N and G442N. Each amino acid substitution introduces an N-linked glycosylation motif (NxS/T). The AA substitutions are numbered from the first amino acid in mature secreted protein (E), following cleavage of signaling sequence (e.g., MGWSCIILFL-VATATGVHS (SEQ ID NO: 147)).

Figure 18A:
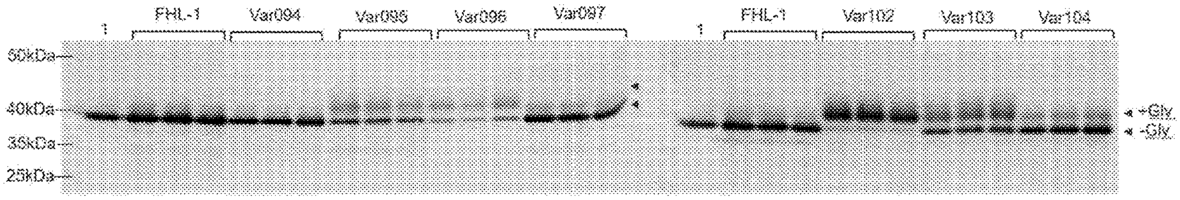
FIGS. 18A and 18B show examples of representative western blots (anti-CFH antibody) showing the extent of glycosylation for single amino acid substitutions in the FHL-1 framework (shown are three independent transfections per construct). Arrowheads indicate the mobility shift between glycosylated (+Gly) and non-glycosylated (−Gly) proteins. Control lane 1 contains purified FHL-1 protein.
Figure 18B:
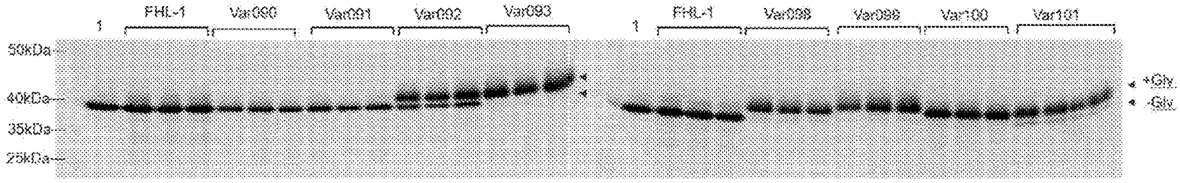

Western blot analysis illustrated in FIGS. 18A and 18B shows the extent of glycosylation for single amino acid substitutions in the FHL-1 framework after 3 independent transfections per construct. The data in FIGS. 18A-18B show which point mutations resulted in full glycosylation, partial glycosylation, or no glycosylation of the parent framework. Arrowheads indicate the mobility shift between glycosylated (+Gly) and non-glycosylated (−Gly) proteins. Control lane 1 contains purified FHL-1 protein. The examples of glycoengineered variants of FHL-1 were cloned into pcDNA3.1 (+) vector and expressed using expi-CHO Expression System (standard protocol) at 0.8 mL scale in 96-well culture format. Culture supernatants were collected at 6 days post-transfection. Protein expression and integrity was analyzed by nonreducing western blot with anti-CFH antibody (A237). Glycosylation was detected via shift of full-length expression band on gel. Arrows indicate shift for glycosylated and non-glycosylated bands.

Figure 19:
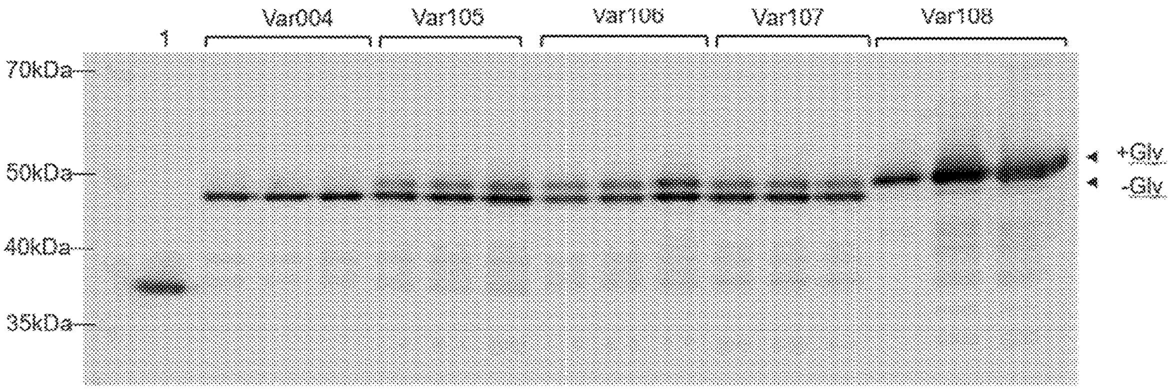
FIG. 19 shows an example of a representative western blots (anti-CFH antibody) showing the extent of glycosylation for single amino acid substitutions in the Var004 framework (shown are three independent transfections per construct). Arrows indicate the mobility shift between glycosylated (+Gly) and non-glycosylated (−Gly) proteins. Control lane 1 contains purified FHL-1.

Similar analysis is presented in FIG. 19 showing representative western blots (anti-CFH antibody A237) showing the extent of glycosylation for single amino acid substitutions in the FHL-1 engineered variant Var004 framework. In this example, the substitution at G442N (Var108) is a substitution effective at introducing strong glycosylation within the GlySer linker sequence of the construct. Arrows indicate the mobility shift between glycosylated (+Gly) and non-glycosylated (−Gly) proteins. Control lane 1 contains purified FHL-1. Again, glycoengineered variants of Var004 framework were cloned into pcDNA3.1 (+) vector and expressed using expi-CHO Expression System (standard protocol) at 0.8 mL scale in 96-well culture format. Culture supernatants were collected at 6 days post-transfection. Protein expression and integrity was analyzed by nonreducing western blot with anti-CFH antibody (A237). Glycosylation was detected via shift of full-length expression band on gel. Arrows indicate shift for glycosylated and nonglycosylated bands. The table of FIG. 20 represents the percent glycosylation for examples of representative FHL-1 engineered variants assayed as described above. Percent glycosylation was calculated as signal intensity of glycosylated monomer band divided by signal intensity of both glycosylated and nonglycosylated monomer bands. "*" indicates variant sequences with >90% glycosylated monomer. FIG. 20 shows mean % glycosylation and standard deviation (SD) for n=3 independent transfections per construct. Of note, representative FHL-1 engineered variants Var093, Var099, Var100, Var102, and Var108 result in over >90% glycosylation of monomer. The various tested substitutions to introduce NxS/T glycosylation motifs had different degrees of effectiveness at promoting construct glycosylation.

Figures 21A, 21B:
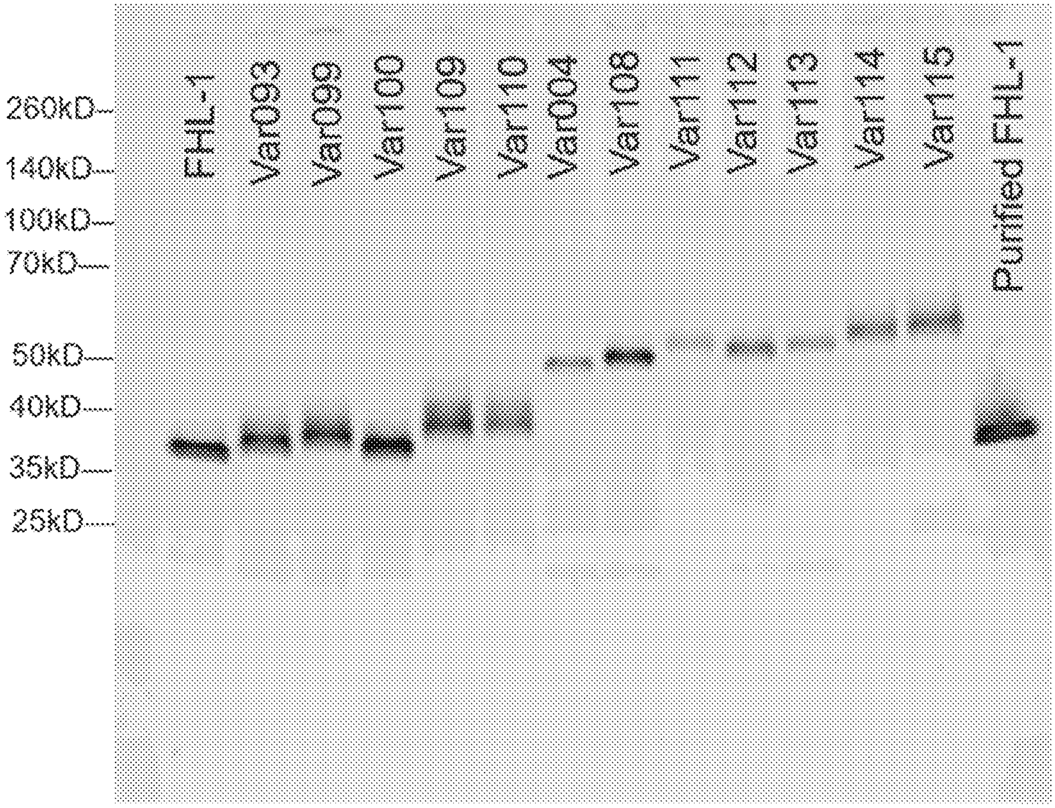
FIGS. 21A and 21B show examples of a representative western blot (anti-CFH antibody) showing the extent of glycosylation for combined amino acid substitutions in FHL-1 variants, as described herein. Mobility shifts are apparent between multiple glycosylated variants and their single glycosylated parental constructs. Lane labeled FHL-1 contains CHO expression supernatant from native FHL-1 sequence. Table summarizes the amino acid substitutions present in each variant.

Additional glycosylation analysis is presented in FIGS. 21A and 21B where representative western blot (anti-CFH antibody A237) reveals the extent of glycosylation for combined amino acid substitutions in the FHL-1 and Var004 frameworks. This data shows single, double, and triple glycosylated variants on the FHL-1 and Var004 frameworks. Each of the included sequences represent constructs where the introduced NxS/T motif is fully glycosylated when the construct is expressed in CHO culture. Mobility shifts are apparent between multiple glycosylated variants and their single glycosylated parental constructs. The table in FIG. 21B summarizes the amino acid substitutions present in each representative variant and the lane labeled "Purified FHL-1" contains expression supernatant from native FHL-1 sequence as a reference standard. The constructs were cloned into pcDNA3.1 (+) vector and expressed using expi-CHO Expression System (standard protocol) at 0.8 mL scale in 96-well culture format. Culture supernatants were collected at 7 days post-transfection. Protein expression and integrity was analyzed by nonreducing Tris-Glycine SDS-PAGE, followed by western blot with anti-CFH antibody (A237). Glycosylation was detected via shift of full-length expression band on gel.

FIGS. 22A and 22B are a bar graphs showing the quantification of protein integrity and expression level measured from Western blot analysis using anti-CFH antibody (A237) for multiple glycosylated FHL-1 engineered variants (e.g., FHL-1 engineered variants with one or more AA substitutions) as described herein. This data shows how glycosylation improves the stability and titer of expressed constructs. FIG. 22A illustrates the percent of full-length monomer quantified by measuring densitometry of full-length monomer divided by densitometry of total lane from monomer through 25 kDa. FIG. 22B is a bar graph showing the relative protein expression level of multiple glycosylated variants relative to FHL-1 engineered variant, Var004. Relative protein expression levels were determined by dividing the band intensity of each variant by the band intensity of Var004, from non-reducing western blot analysis using anti-CFH antibody A237. Graphs show mean±/−SEM for D7 supernatants from triplicate transfections at 0.8 mL scale.

A representative western blot from this experiment is shown in FIG. 21A. Differences between variants and Var004 were analyzed by one-way ANOVA with Dunnett's multiple comparisons. Of note, all of the glycovariants (e.g., FHL1 engineered variants with one or more AA substitutions, as described herein) have improved protein integrity over representative FHL-1 engineered variant Var004. Also of note, Var108 is shown to have significantly improved expression titer relative to Var004.

The table in FIG. 23 shows a summary of the quantification of protein integrity and expression level as measured from Western blot analysis using anti-CFH antibodies (A237), as detailed in FIG. 21A to 22B, and illustrates which glycosylation sites improve the titer and integrity of expressed constructs. Percent expression of full-length monomer was quantified by measuring densitometry of full-length monomer divided by densitometry of total lane from monomer through 25 kDa on A237 western blot. Relative protein expression levels were determined by dividing the band intensity of each variant by the band intensity of Var004. Of note, Var108, Var114 and Var115 have greater than 2-fold higher protein expression levels relative to Var004.

Figures 24A, 24B:
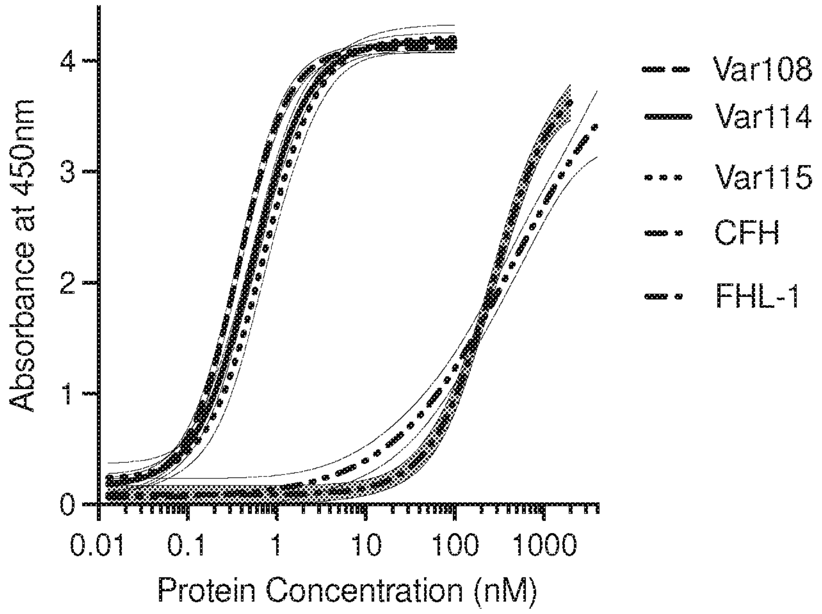
FIGS. 24A and 24B illustrate the binding activity of engineered variants of FHL-1 (e.g., Var108, Var114, Var115) and control proteins (e.g., FHL-1, CFH) to heparin, as measured by ELISA. The graph of FIG. 24A shows mean absorbance values from multiple independent heparin-binding assays. The table of FIG. 24B summarizes the EC50 values across multiple experiments.

As compared with CFH and FHL-1, the engineered variants, such as Var108, Var114, and Var115 may bind to heparin with significantly greater affinity. For example, FIGS. 24A and 24B show the results of experiments examining binding of these variants of FHL-1 (Var108, Var114, and Var115) compared with CFH and FHL-1. FIG. 24A is a graph showing the mean absorbance values for multiple heparin-binding assays comparing CFH and FHL-1 to each of Var108, Var114, and Var115. FIG. 24B is a table summarizing this data, showing significantly lower EC50 values for Var108, Var114, and Var 115 compared with CFH and FHL-1. As shown, Var108, Var114, and Var115 each have over 500-fold (500×) improved heparin binding activity relative to CFH and FHL-1. This data suggests that these variants may have a greatly improved ability to bind to surface ligands recognized by the CFH SCR7 domains.

Figures 25A, 25B:
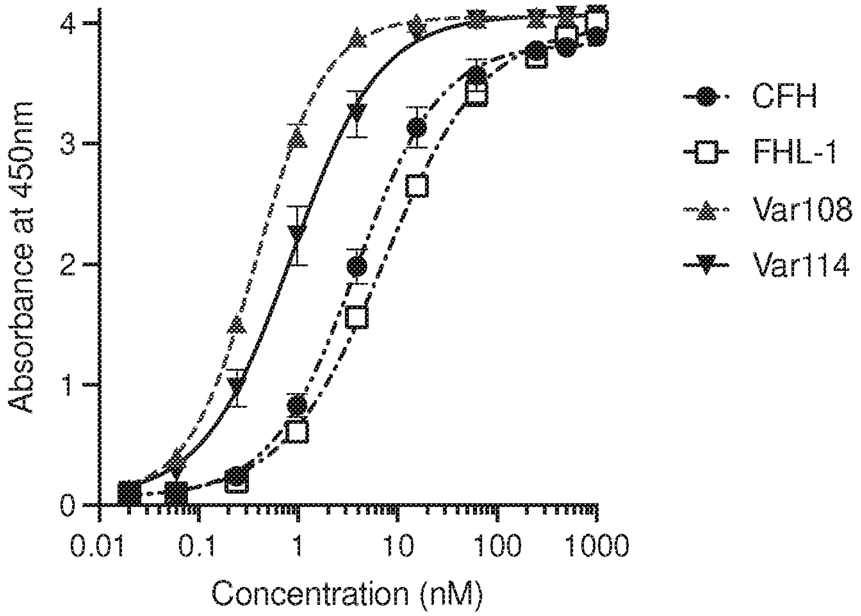
FIGS. 25A and 25B illustrate the binding activity of engineered variants of FHL-1 (e.g., Var108, Var114) and control proteins (e.g., FHL-1, CFH) to C3b, as measured by ELISA. The graph of FIG. 25A shows mean absorbance values from multiple independent C3b-binding assays. The table of FIG. 25B summarizes the EC50 values across multiple experiments

As shown in FIGS. 25A and 25B, the engineered glycovariant proteins as described herein may have an improved C3b binding activity compared to the control proteins, indicating that the C3b regulatory activities of CFH/FHL-1 are preserved (and may be slightly better in comparison with CFH and FHL-1). C3b binding activity is measured by incubating glycovariant proteins on an ELISA plate functionalized with human C3b, and detecting bound protein with an anti-CFH antibody.

Figures 26A, 26B:
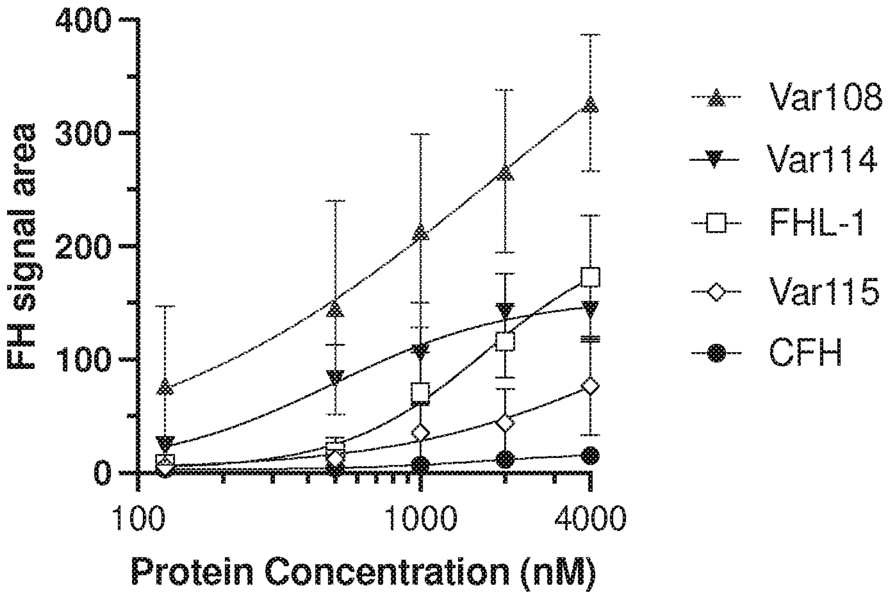
FIGS. 26A and 26B illustrate the binding activity of engineered variants of FHL-1 (e.g., Var108, Var114, Var115) and control proteins (e.g. FHL-1, CFH) to cultured human RPE cells (ARPE-19 cell line), as measured by anti-CFH antibody immunostaining. The table of FIG. 26B summarizes the EC50 values and maximal binding signal across multiple experiments.

The engineered FHL-1 variants may bind to human RPE cells at least as well as control (e.g., FHL-1 and CFH). For example, as shown in FIGS. 26A and 26B, variants Var108 and Var114 show improved binding to RPE cells relative to CFH and FHL-1, demonstrating improved ability of the constructs to bind to cells via the SCR7 domain. FIG. 26A is a graph showing the binding activity of the test proteins over a range of protein concentrations. FIG. 26B is a table summarizing the results of multiple assays measuring the EC50 and Emax. In this example, ARPE-19 cells were grown to confluency on 96-well tissue culture plates. Cells were serum-starved for 24 hr and incubated in serum-free media with 125-4000 nM CFH, FHL-1, Var108, Var114, or Var115 for 20 min at 37° C. After washing off unbound protein, cells were fixed in 2% PFA, blocked, and stained overnight with anti-FH antibody (OX23), followed by Texas Red secondary, and DAPI nuclear stain. Protein binding was measured by high content imager, and signal area was normalized against DAPI nuclear count. Graphs show mean±SEM from multiple experiments. EC50 and Emax values were calculated by 4PL sigmoidal nonlinear regression.

Of the variants described herein, in some cases (e.g., Var114) the engineered variants of FHL-1 described herein may be able to inhibit complement activation in a surface-dependent manner. Surprisingly, in some cases the variant may be a better surface-dependent regulator of complement than either control protein, as shown in FIGS. 27A-27B. In FIGS. 27A-27B, ARPE-19 cells were grown to confluence, serum-starved overnight then incubated in serum-free media with 62.5-4000 nM CFH, FHL-1, Var108, Var114, or media for 20 minutes at 37° C. Unbound protein was removed by washing cells with PBS, followed by challenging cells with FH-depleted human serum (5% serum volume) for 2 hours. After complement challenge, cells were washed, fixed in 2% PFA, and stained with anti-C5b9 antibody (clone AE11) to visualize MAC deposition and DAPI to visualize cell nuclei. MAC signal area was normalized against DAPI nuclear count. Graphs show mean±SEM from multiple experiments. IC50 and Imax values were calculated by 4PL sigmoidal nonlinear regression. Note (**) that the Var108 regression was performed for concentrations 0-2000 nM because of loss of activity at 4000 nM concentration.

In general, as shown in FIG. 28, there is a very strong linear correlation between the improved cell binding by Var114 and its ability to regulate complement activation. This confirms the design concept behind the FHL-1 variant campaign described above. As shown, the SCR7 domain duplication achieves improvements in complement regulation by virtue of conferring increased cellular surface binding activity. Note that Var108 demonstrated increased cellular binding that was not associated with increased complement regulatory activity at concentrations >2000 nM. FIG. 28 shows the binding and complement inhibition potency for the variants measured of FIGS. 26A-26B and FIG. 27A-27B, (0-4000 nM concentrations), e.g., for engineered variants of FHL-1 (e.g. Var108, Var114) and for control proteins (FHL-1, CFH). For each tested protein concentration, mean FH binding signal quantifications were plotted against mean MAC deposition. Correlation was measured by linear regression.

Figures 29A, 29B:
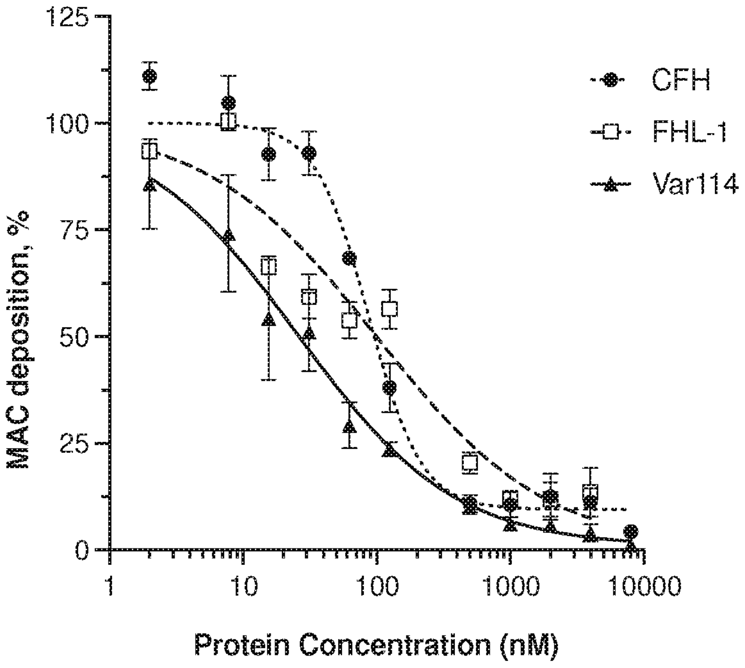
FIGS. 29A and 29B illustrate surface-independent complement inhibitory activity of an engineered variant of FHL-1 (e.g., Var114) as compared to control proteins (e.g. FHL-1, CFH) on cultured human RPE cells (ARPE-19 cell line), measured by anti-C5b9 (MAC) antibody immunostaining. The table of FIG. 29B summarizes the IC50 values for complement inhibition across multiple experiments (e.g., FIG. 29A).

Complement regulatory activity of Var114 and control proteins was examined in an experimental system that includes both fluid-phase and surface-dependent complement activation. The results are shown in FIGS. 29A-29B. The engineered variant Var114 has an improved ability to regulate complement activation on RPE cells in this system. ARPE-19 cells were grown to confluence, serum-starved overnight then incubated in serum-free media with FH-depleted serum (5% serum by volume) and 62.5-4000 nM CFH, FHL-1, or Var114 for 2 hours at 37° C. After complement challenge, cells were washed, fixed in 2% PFA, and stained with anti-C5b9 antibody (clone AE11) to visualize MAC deposition and DAPI to visualize cell nuclei. MAC signal area was normalized against DAPI nuclear count. Graphs show mean±SEM from multiple experiments. IC50 values were calculated by 4PL sigmoidal nonlinear regression.

Figures 30A, 30B:
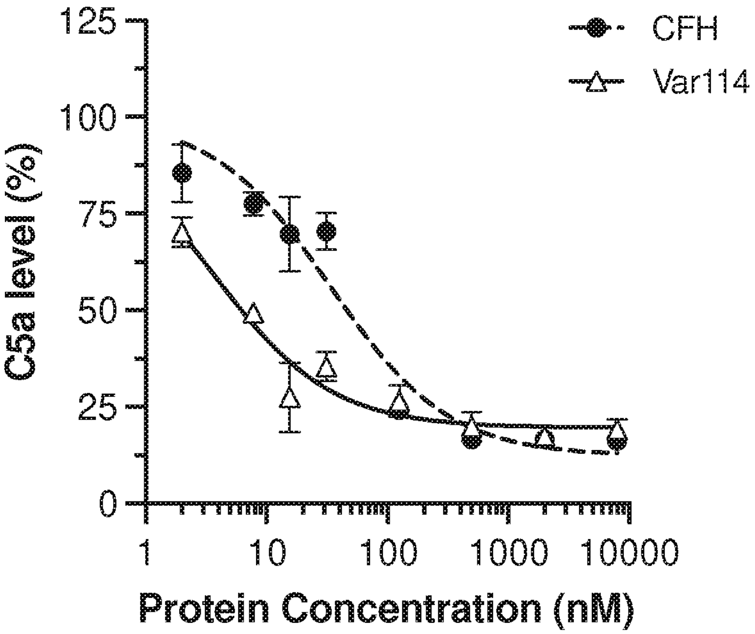
FIGS. 30A and 30B illustrate complement inhibitory activity of an engineered variant of FHL-1 (e.g., Var114) and a control protein (CFH) on cultured human RPE cells (ARPE-19 cell line), as measured by C5a ELISA.

In some examples Var114 (or related variants) showed a superior ability to inhibit C5a generation (compared to CFH control). This is illustrated in FIGS. 30A-30B. For example, in FIG. 30A ARPE-19 cells were grown to confluence, serum-starved overnight then incubated in serum-free media with FH-depleted serum (5% serum by volume) and 62.5-4000 nM CFH, FHL-1, or Var114 for 2 hours at 37 C. After complement challenge, assay supernatants were collected and C5a levels analyzed by ELISA. Graphs show mean±SEM from multiple experiments. IC50 values were calculated by 4PL sigmoidal nonlinear regression. FIG. 30B illustrates examples of data in a table summary showing IC50 values for inhibition of C5a generation by Var114 and CFH as measured by ELISA in ARPE-19 cell culture supernatants after complement challenge.

Figures 31A, 31B:
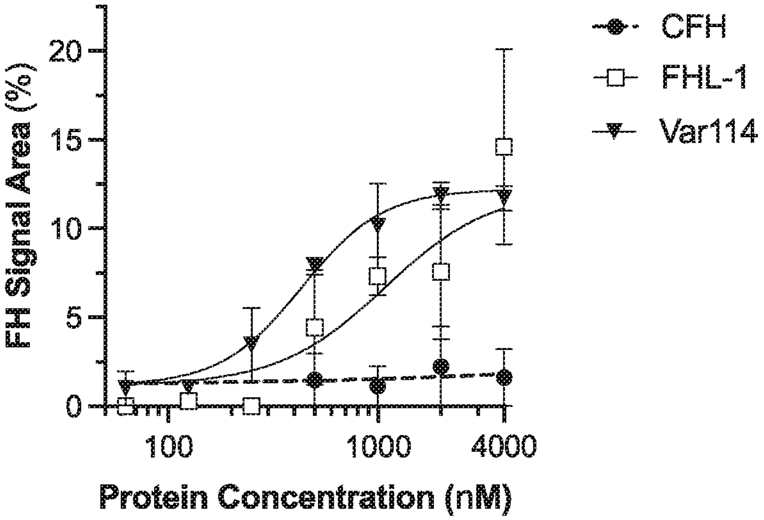
FIGS. 31A and 31B illustrate the binding activity of an engineered variant of FHL-1 (e.g., Var114) and control proteins (e.g. FHL-1, CFH) to cultured human iPS-RPE cells, as measured by anti-CFH antibody immunostaining. The table of FIG. 31B summarizes the EC50 values across multiple experiments.

FIGS. 31A-31B illustrate another example showing the enhanced cellular surface binding activity of Var114. In this example, iPS cell-derived RPE cultures were used to support the conclusions shown in FIG. 26. Specifically, Var114 has improved ability to bind iPS cell-derived human RPE cells, compared to control proteins. In this experiment, human iPS-RPE cells were matured in trans well plates for 4-6 weeks. Cells were serum-starved for 24 hours and incubated in serum-free media with 62.5-4000 nM CFH, FHL-1, or Var114 for 20 min at 37 C. After washing off unbound protein, cells were fixed in 2% PFA, blocked, and stained overnight with anti-FH antibody (OX23), and DAPI nuclear stain. Binding signal area was measured. Graphs show mean±SEM from multiple experiments. EC50 values were calculated by 4PL sigmoidal nonlinear regression.

Figure 32:
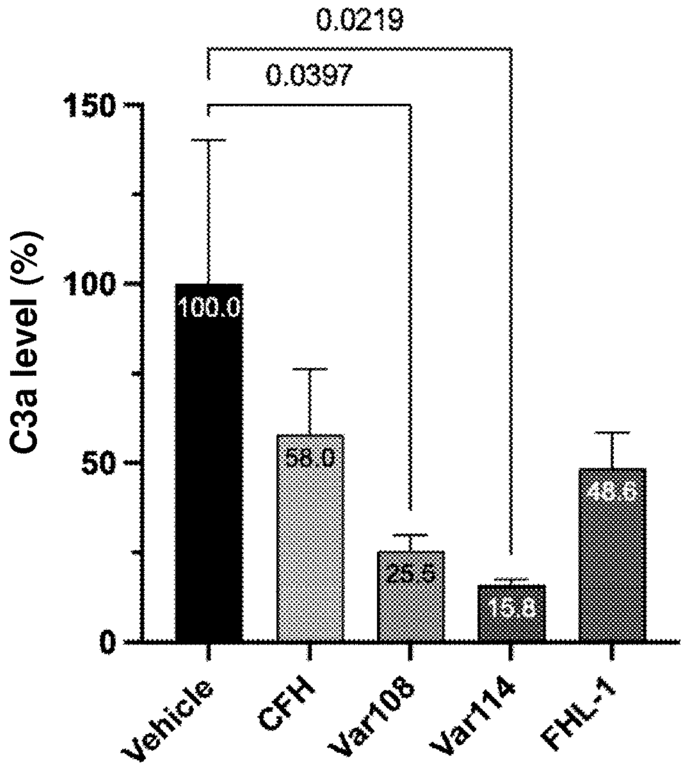
FIG. 32 is a graph illustrating inhibition of C3a in rat vitreous humor samples following IVT delivery of engineered variants of FHL-1 (e.g. Var108, Var114) and control proteins (e.g. FHL-1, CFH) in a laser-induced CNV model of complement activation.
Figure 33:
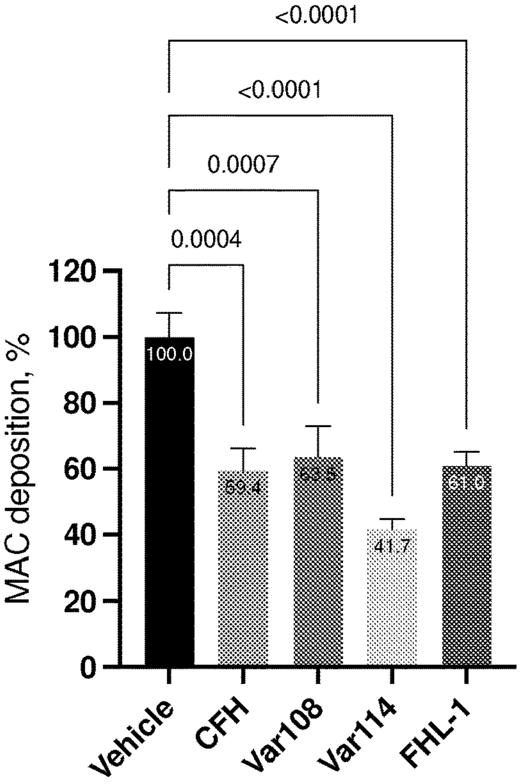
FIG. 33 is a graph illustrating inhibition of MAC deposition in rat RPE following IVT delivery of engineered variants of FHL-1 (e.g. Var108, Var114) and control proteins (E.g. FHL-1, CFH) in a laser-induced CNV model of complement activation.
Figure 34:
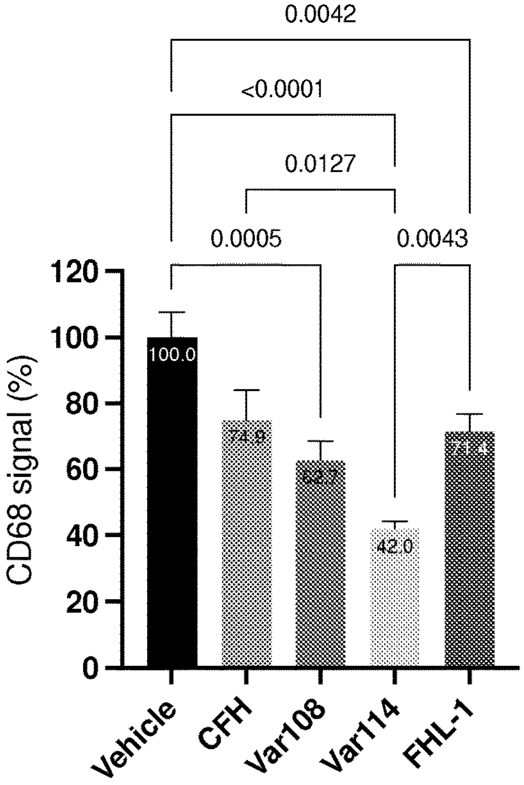
FIG. 34 is a graph illustrating inhibition of macrophage recruitment in rat RPE following IVT delivery of engineered variants of FHL-1 (e.g. Var108, Var114) and control proteins (E.g. FHL-1, CFH) in a laser-induced CNV model of complement activation.

FIGS. 32-34 show the in vivo efficacy of Var108 and Var114, using a rat laser-induced model of retinal injury, which is known to induce activation of the complement pathway. For example, in the experiment summarized by FIG. 32, adult male brown Norway rats were subjected to laser-induced retinal injury (4 lesions/eye), immediately followed by intravitreal injection with 170 picomoles of engineered variants of FHL-1 (e.g. Var108, Var114) or control proteins (e.g. CFH, FHL-1) or vehicle. Vitreous humor samples were collected at 3 days after laser administration, and C3a levels were measured by ELISA. Graphs depict mean±/−SEM values of C3a, normalized to the vehicle control. Differences between groups measured by One-way ANOVA+Tukey's multiple comparisons test. This experiment system uses an established model of complement induced retinal injury to compare the efficacy of engineered variants of FHL-1 against control proteins. In this system, the engineered variants are effective at reducing ocular levels of C3a compared to vehicle treatment controls.

FIG. 33 illustrates the inhibition of MAC deposition by some of the engineered variants of FHL-1 (e.g. Var108, Var114) in a laser-induced model of retinal injury, which is known to induce activation of the complement pathway. In this example, adult male brown Norway rats were subjected to laser-induced retinal injury (4 lesions/eye), immediately followed by intravitreal injection with 170 picomoles of engineered variants of FHL-1 (e.g. Var108, Var114) or control proteins (e.g. CFH, FHL-1) or vehicle. Rat eyes were dissected at 3 days following laser, and RPE flat-mounts were immunostained for MAC deposition with anti-C5b9 antibody (clone AE11), and lesions were visualized by phalloidin staining. Graphs depict mean+/−SEM MAC signal area within phalloidin lesion area. Differences between groups measured by One-way ANOVA+Tukey's multiple comparisons test. An established model of laser induced retinal injury may be used to compare the efficacy of engineered variants of FHL-1 against control proteins. In this system, the engineered variants (e.g., Var108 and Var114) are effective at reducing MAC deposition on the RPE (readout of terminal complement activation).

FIG. 34 shows inhibition of macrophage recruitment by engineered variants of FHL-1 (e.g., Var108 and Var114) and control proteins (e.g., FHL-1 and CFH) in rat RPE in a laser-induced model of retinal injury, which is known to induce activation of the complement pathway. Adult male brown Norway rats were subjected to laser-induced retinal injury (4 lesions/eye), immediately followed by intravitreal injection with 170 picomoles of engineered variants of FHL-1 (e.g. Var108, Var114) or control proteins (e.g. CFH, FHL-1) or vehicle. Rat eyes were dissected at 3 days following laser, and RPE flat-mounts were immunostained for macrophage infiltration with anti-CD68 antibody, and lesions were visualized by phalloidin staining. Graphs depict mean±/−SEM macrophage signal area within phalloidin lesion area. Differences between groups measured by One-way ANOVA+Tukey's multiple comparisons test. Thus, the efficacy of engineered variants of FHL-1 was compared against control proteins using an established model of laser induced retinal injury. The engineered variants were more effective at suppressing macrophage recruitment (as measured by CD68), compared to control proteins. This demonstrates immunomodulatory activities of the variants in a context of ocular complement activation.

Compositions

Any of the engineered variants of FHL-1 described herein may be used as part of a pharmaceutical composition. The pharmaceutical compositions comprising engineered variants of FHL-1 described herein may include one or more pharmaceutically acceptable carriers. The pharmaceutical compositions may be suitable for any mode of administration, for example, by intravitreal administration.

In some examples, the composition comprises a polypeptide of SEQ ID NO: 18-137. For example, in some examples the pharmaceutical composition includes a peptide having the sequence of SEQ ID NO: 3. In some examples the pharmaceutical composition includes a peptide having the sequence of SEQ ID NO: 4. In some examples the pharmaceutical composition includes a peptide having the sequence of SEQ ID NO: 5. In some examples the pharmaceutical composition includes a peptide having the sequence of SEQ ID NO: 6. In some examples the pharmaceutical composition includes a peptide having the sequence of SEQ ID NO: 7. In some examples the pharmaceutical composition includes a peptide having the sequence of IRV. In some examples the pharmaceutical composition includes a peptide having the sequence IR. In some examples the pharmaceutical composition includes a peptide having the sequence of SEQ ID NO: 11. In some examples the pharmaceutical composition includes a peptide having the sequence of SEQ ID NO: 12. In some examples the pharmaceutical composition includes a peptide having the sequence of SEQ ID NO: 13. In some examples the pharmaceutical composition includes a peptide having the sequence of LKP. In some examples the pharmaceutical composition includes a peptide having the sequence of KP. In some examples the pharmaceutical composition includes a peptide having the sequence of SEQ ID NO: 17. In some examples the pharmaceutical composition includes combinations of any of two peptides having the sequence of any two or more of SEQ ID NO: 3-7, 11, 13, 17-137, IRV, IR, I, LKP, KP, or P. In some examples the pharmaceutical composition includes three or more peptides having the sequence of any three or more of SEQ ID NO: 3-7, 11, 13, 17-137, IRV, IR, I, LKP, KP, or P.

In some examples, the pharmaceutical compositions comprising a peptide of any one or more of SEQ ID NO: 3-7, 11, 13, 17-137, IRV, IR, I, LKP, KP, or P, described herein and a pharmaceutically acceptable carrier is suitable for administration to a human subject. Such carriers are well known in the art (see, e.g., Remington's Pharmaceutical Sciences, 15th Edition, pp. 1035-1038 and 1570-1580). In some examples, the pharmaceutical compositions comprising a peptide of any one or more of SEQ ID NO: 3-7, 11, 13, 17-137, IRV, IR, I, LKP, KP, or P, described herein and a pharmaceutically acceptable carrier is suitable for ocular injection. In some examples, the pharmaceutical composition is suitable for intravitreal injection. In some examples, the pharmaceutical composition is suitable for subretinal delivery. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidose forms. The compositions are generally formulated as sterile and substantially isotonic solution.

In one example, the peptide having the sequence of any one or more of SEQ ID NO: 11-13, or 17-137, IRV, IR, I, LKP, KP, or P, as detailed above is formulated into a pharmaceutical composition intended for subretinal or intravitreal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. In one example, the carrier is an isotonic sodium chloride solution. In another example, the carrier is a balanced salt solution. In one example, the carrier includes tween. If the product is to be stored long-term, it may be frozen in the presence of glycerol or Tween20. In another example, the pharmaceutically acceptable carrier comprises a surfactant, such as perfluorooctane (Perfluoron liquid).

In certain examples of the methods described herein, the pharmaceutical composition described above is administered to the subject by subretinal injection. In other examples, the pharmaceutical composition is administered by intravitreal injection. Other forms of administration that may be useful in the methods described herein include, but are not limited to, direct delivery to a desired organ (e.g., the eye), oral, inhalation, intranasal, intratracheal, intravenous, intramuscular, subcutaneous, intradermal, and other parental routes of administration. Routes of administration may be combined, if desired. In certain examples, the pharmaceutical compositions of the disclosure are administered after administration of an initial loading dose of the complement system protein.

In some examples, the route of administration is chosen such that it reduces the risk of retinal detachment in the patient (e.g., intravitreal or suprachoroidal rather than subretinal administration). In some examples, intravitreal administration is chosen if the composition is to be administered to an elderly adult (e.g., at least 60 years of age). In particular examples, any of the pharmaceutical compositions disclosed herein are administered to a subject intravitreally. Procedures for intravitreal injection are known in the art (see, e.g., Peyman, G. A., et al. (2009) Retina 29(7): 875-912 and Fagan, X. J. and Al-Qureshi, S. (2013) Clin. Experiment. Ophthalmol. 41(5): 500-7). Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE®). A similar solution may also be used to clean the eyelid, eyelashes, and any other nearby tissues {e.g., skin). Any suitable anesthetic may be used, such as lidocaine or proparacaine, at any suitable concentration. Anesthetic may be administered by any method known in the art, including without limitation topical drops, gels or jellies, and subconjunctival application of anesthetic. Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site. During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

The composition may be delivered in a volume of from about 0.1 µL to about 1 mL, including all numbers within the range, depending on the size of the area to be treated, the route of administration, and the desired effect of the method. In one example, the volume is about 50 µL. In another example, the volume is about 70 µL. In one example, the volume is about 100 µL. In another example, the volume is about 125 µL. In another example, the volume is about 150 µL. In another example, the volume is about 175 µL. In yet another example, the volume is about 200 µL. In another example, the volume is about 250 µL. In another example, the volume is about 300 µL. In another example, the volume is about 450 µL. In another example, the volume is about 500 µL. In another example, the volume is about 600 µL. In another example, the volume is about 750 µL. In another example, the volume is about 850 µL. In another example, the volume is about 1000 µL.

For example, the dose may be between about 100 ng/eye to about 10 mg/eye (e.g., about 100 ng/eye, about 150 ng/eye, about 200 ng/eye, about 250 ng/eye, about 300 ng/eye, about 400 ng/eye, about 500 ng/eye, about 600 ng/eye, about 700 ng/eye, about 800 ng/eye, about 900 ng/eye, about 1 µg/eye, about 2 µg/eye, about 3 µg/eye, about 5 µg/eye, about 10 µg/eye, about 15 µg/eye, about 20 µg/eye, about 25 µg/eye, about 30 µg/eye, about 35 µg/eye, about 40 µg/eye, about 50 µg/eye, about 60 µg/eye, about 70 µg/eye, about 80 µg/eye, about 90 µg/eye, about 100 µg/eye, about 120 µg/eye, about 150 µg/eye, about 175 µg/eye, about 200 µg/eye, about 250 µg/eye, about 300 µg/eye, about 350 µg/eye, about 400 µg/eye, about 500 µg/eye, about 750 µg/eye, about 1 mg/eye, about 1.5 mg/eye, about 2 mg/eye, about 2.5 mg/eye, about 3 mg/eye, about 3.5 mg/eye, about 4 mg/eye, about 4.5 mg/eye, about 5 mg/eye, about 5.5 mg/eye, about 6.0 mg/eye, about 6.5 mg/eye, about 7.0 mg/eye, about 7.5 mg/eye, about 8.0 mg/eye, about 8.5 mg/eye, about 9.0 mg/eye, about 9.5 mg/eye, about 10 mg/eye or any ranges within these).

Still other dosages and administration volumes in these ranges may be selected by the attending physician, taking into account the physical state of the subject, preferably human, being treated, the age of the subject, the particular ocular disorder and the degree to which the disorder, if progressive, has developed. For extra-ocular delivery, the dosage may be increased according to the scale-up from the retina.

Methods of Treatment/Prophylaxis

Described herein are various methods of preventing, treating, arresting progression of or ameliorating the ocular disorders and retinal changes associated therewith. Any of these methods may include identifying the patient that may benefit from one or more of these therapies and/or identifying which one or more of the therapies described herein may be most beneficial to a particular patient. Any of these methods may include determining the dose to be delivered, the delivery route and/or the schedule for delivering one or more doses.

Generally, the methods include administering to a mammalian subject in need thereof, an effective amount of any of the compositions described herein. For example, treatment of age-related macular degeneration may include the localized delivery of a therapeutic composition as described herein to the patient's retina. The cells that will be the treatment target in these diseases may include photoreceptor cells in the retina or the cells of the RPE underlying the neurosensory retina. In a certain aspect, the disclosure provides a method of treating a subject having age-related macular degeneration (AMD), comprising the step of administering to the subject any of the compositions described herein.

In a particular example, methods of preventing, arresting progression of or ameliorating vision loss associated with an ocular disorder in the subject are provided. Vision loss associated with an ocular disorder refers to any decrease in peripheral vision, central (reading) vision, night vision, day vision, loss of color perception, loss of contrast sensitivity, or reduction in visual acuity. The methods and compositions described herein may be directed to increasing photoreceptor function. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient. Photoreceptor function may be assessed using a functional study, e.g., ERG or perimetry, which are conventional in the art.

For each of the described methods, the treatment may be used to prevent the occurrence of retinal damage or to rescue eyes having mild or advanced disease. As used herein, the term "rescue" means to prevent progression of the disease to total blindness, prevent spread of damage to uninjured ocular cells, improve damage in injured ocular cells, or to provide enhanced vision. In one example, the composition is administered before the disease becomes symptomatic or prior to photoreceptor loss. By symptomatic is meant onset of any of the various retinal changes described above or vision loss. In another example, the composition is administered after disease becomes symptomatic. In yet another example, the composition is administered after initiation of photoreceptor loss. In another example, the composition is administered after outer nuclear layer (ONL) degeneration begins. In some examples, it is desirable that the composition is administered while bipolar cell circuitry to ganglion cells and optic nerve remains intact. In another example, the composition is administered after initiation of photoreceptor loss. In yet another example, the composition is administered when less than 90% of the photoreceptors are functioning or remaining, as compared to a non-diseased eye. In another example, the composition is administered when less than 80% of the photoreceptors are functioning or remaining. In another example, the composition is administered when less than 70% of the photoreceptors are functioning or remaining. In another example, the composition is administered when less than 60% of the photoreceptors are functioning or remaining. In another example, the composition is administered when less than 50% of the photoreceptors are functioning or remaining. In another example, the composition is administered when less than 40% of the photoreceptors are functioning or remaining. In another example, the composition is administered when less than 30% of the photoreceptors are functioning or remaining. In another example, the composition is administered when less than 20% of the photoreceptors are functioning or remaining. In another example, the composition is administered when less than 10% of the photoreceptors are functioning or remaining. In one example, the composition is administered only to one or more regions of the eye. In another example, the composition is administered to the entire eye. In another example, the method includes performing functional and imaging studies to determine the efficacy of the treatment. These studies include ERG and in vivo retinal imaging, as described in the examples below. In addition, visual field studies, perimetry and microperimetry, pupillometry, mobility testing, visual acuity, contrast sensitivity, color vision testing may be performed.

In yet another example, any of the methods described herein may be performed in combination with another, or secondary, therapy. The therapy may be any now known, or as yet unknown, therapy which helps prevent, arrest or ameliorate any of the described retinal changes and/or vision loss.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. A polypeptide comprising:

a first region comprising the amino acid sequence of complement factor H domains SCR1-SCR7 having at least 80% identity to SEQ ID NO: 3;

a second region comprising the amino acid sequence of Factor H-like protein 1 domains SCR6-SCR7 having at least 80% identity to SEQ ID NO: 17; and a linker domain separating the first region from the second region.

2. The polypeptide of claim 1, wherein the polypeptide comprises a first junction region between the first region and the linker domain and a second junction region between the second region and the linker domain.

3. The polypeptide of claim 2, wherein the first junction region has the amino acid sequence of SEQ ID NO: 7 and the second junction region has the amino acid sequence of SEQ ID NO: 13 or LKP.

4. The polypeptide of claim 1, wherein the linker domain comprises the amino acid sequence of SEQ ID NO: 11.

5. The polypeptide of claim 1, wherein the polypeptide comprises the amino acid sequence-having at least 90% identity to SEQ ID NO: 131.

6. The polypeptide of claim 1, wherein the polypeptide comprises the amino acid sequence of SEQ ID NO: 21 having one or more amino acid substitutions selected from the group consisting of: L6S, L6T, A289S, A289T, Y380S, Y380T, T16N, D258N, Y334N, D21N, G286N, H355N, A407N, R426N, S428N, G431N, G436N, G441N and G442N.

7. The polypeptide of claim 1, wherein the polypeptide comprises the amino acid sequence of SEQ ID NO: 21 having one or more amino acid substitutions selected from the group consisting of: L6S, L6T, A289S, A289T, Y380S, Y380T, T16N, D258N, Y334N, D21N, G286N, H355N, A407N, R426N and S428N.

8. The polypeptide of claim 1, wherein the polypeptide comprises the amino acid sequence of SEQ ID NO: 125, SEQ ID NO: 131, or SEQ ID NO: 132.

9. The polypeptide of claim 1, wherein the first region has the amino acid sequence of any one of SEQ ID NO: 3, SEQ ID NO: 139 or SEQ ID NO: 140; the second region has the amino acid sequence of SEQ ID NO: 17, and the linker domain has the amino acid sequence of SEQ ID NO: 138.

10. The polypeptide of claim 2, wherein the first junction region has the amino acid sequence of any one of SEQ ID NO: 4, SEQ ID NO: 5, SEQ ID NO: 6, SEQ ID NO: 7, IRV, IR, or I, and wherein the second junction region has the amino acid sequence of any one of SEQ ID NO: 13, LKP, KP, or P.

11. The polypeptide of claim 1, wherein the first region has the amino acid sequence having at least 95% identity to SEQ ID NO: 3, and wherein the second region has the amino acid sequence having at least 95% identity to SEQ ID NO: 17.

12. The polypeptide of claim 1, wherein the linker domain comprises a Gly/Ser linker, a poly-Gly linker, or a poly-Ala linker.

13. The polypeptide of claim 1, wherein the linker domain comprises the amino acid sequence of any one of GGGS (SEQ ID NO: 141), GGGSGGGS (SEQ ID NO: 142), GGGGSGGGS (SEQ ID NO: 143), GGGGSGGGSGGGS (SEQ ID NO: 144), or GGGGSGGGGSGGGGS (SEQ ID NO: 11).

14. A pharmaceutical composition comprising the polypeptide of claim 1.

15. A pharmaceutical composition comprising the polypeptide of claim 5.

16. A pharmaceutical composition comprising the polypeptide of claim 6.

17. A pharmaceutical composition comprising the polypeptide of claim 7.

18. A pharmaceutical composition comprising the polypeptide of claim 8.

19. A pharmaceutical composition comprising the polypeptide of claim 11.

20. A pharmaceutical composition comprising the polypeptide of claim 13.

* * * * *

SEQUENCE LISTING

```
Sequence total quantity: 150
SEQ ID NO: 1            moltype = AA  length = 1231
FEATURE                 Location/Qualifiers
source                  1..1231
                        mol_type = protein
                        organism = synthetic construct
SEQUENCE: 1
MRLLAKIICL MLWAICVAED CNELPPRRNT EILTGSWSDQ TYPEGTQAIY KCRPGYRSLG  60
NVIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSCDNP YIPNGDYSPL RIKHRTGDEI TYQCRNGFYP  300
ATRGNTAKCT STGWIPAPRC TLKPCDYPDI KHGGLYHENM RRPYFPVAVG KYYSYYCDEH  360
FETPSGSYWD HIHCTQDGWS PAVPCLRKCY FPYLENGYNQ NYGRKFVQGK SIDVACHPGY  420
ALPKAQTTVT CMENGWSPTP RCIRVKTCSK SSIDIENGFI SESQYTYALK EKAKYQCKLG  480
YVTADGETSG SITCGKDGWS AQPTCIKSCD IPVFMNARTK NDFTWFKLND TLDYECHDGY  540
ESNTGSTTGS IVCGYNGWSD LPICYERECE LPKIDVHLVP DRKKDQYKVG EVLKFSCKPG  600
FTIVGPNSVQ CYHFGLSPDL PICKEQVQSC GPPPELLNGN VKEKTKEEYG HSEVVEYYCN  660
PRFLMKGPNK IQCVDGEWTT LPVCIVEEST CGDIPELEHG WAQLSSPPYY YGDSVEFNCS  720
ESFTMIGHRS ITCIHGVWTQ LPQCVAIDKL KKCKSSNLII LEEHLKNKKE FDHNSNIRYR  780
CRGKEGWIHT VCINGRWDPE VNCSMAQIQL CPPPPQIPNS HNMTTTLNYR DGEKVSVLCQ  840
ENYLIQEGEE ITCKDGRWQS IPLCVEKIPC SQPPQIEHGT INSSRSSQES YAHGTKLSYT  900
CEGGFRISEE NETTCYMGKW SSPPQCEGLP CKSPPEISHG VVAHMSDSYQ YGEEVTYKCF  960
EGFGIDGPAI AKCLGEKWSH PPSCIKTDCL SLPSFENAIP MGEKKDVYKA GEQVTYTCAT  1020
YYKMDGASNV TCINSRWTGR PTCRDTSCVN PPTVQNAYIV SRQMSKYPSG ERVRYQCRSP  1080
YEMFGDEEVM CLNGNWTEPP QCKDSTGKCG PPPPIDNGDI TSFPLSVYAP ASSVEYQCQN  1140
LYQLEGNKRI TCRNGQWSEP PKCLHPCVIS REIMENYNIA LRWTAKQKLY SRTGESVEFV  1200
CKRGYRLSSR SHTLRTTCWD GKLEYPTCAK R                                 1231

SEQ ID NO: 2            moltype = AA  length = 431
FEATURE                 Location/Qualifiers
source                  1..431
                        mol_type = protein
                        organism = synthetic construct
SEQUENCE: 2
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
```

-continued

```
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                      431

SEQ ID NO: 3            moltype = AA  length = 424
FEATURE                 Location/Qualifiers
source                  1..424
                        mol_type = protein
                        organism = synthetic construct
SEQUENCE: 3
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRC                                                              424

SEQ ID NO: 4            moltype = AA  length = 7
FEATURE                 Location/Qualifiers
source                  1..7
                        mol_type = protein
                        organism = synthetic construct
SEQUENCE: 4
IRVSFTL                                                           7

SEQ ID NO: 5            moltype = AA  length = 6
FEATURE                 Location/Qualifiers
source                  1..6
                        mol_type = protein
                        organism = synthetic construct
SEQUENCE: 5
IRVSFT                                                            6

SEQ ID NO: 6            moltype = AA  length = 5
FEATURE                 Location/Qualifiers
source                  1..5
                        mol_type = protein
                        organism = synthetic construct
SEQUENCE: 6
IRVSF                                                             5

SEQ ID NO: 7            moltype = AA  length = 4
FEATURE                 Location/Qualifiers
source                  1..4
                        mol_type = protein
                        organism = synthetic construct
SEQUENCE: 7
IRVS                                                              4

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000

SEQ ID NO: 11           moltype = AA  length = 15
FEATURE                 Location/Qualifiers
source                  1..15
                        mol_type = protein
                        organism = synthetic construct
SEQUENCE: 11
GGGGSGGGGS GGGGS                                                  15

SEQ ID NO: 12           moltype = AA  length = 15
FEATURE                 Location/Qualifiers
source                  1..15
                        mol_type = protein
                        organism = synthetic construct
```

-continued

```
SEQUENCE: 12
EAAAKEAAAK EAAAK                                              15

SEQ ID NO: 13          moltype = AA  length = 4
FEATURE                Location/Qualifiers
source                 1..4
                       mol_type = protein
                       organism = synthetic construct
SEQUENCE: 13
TLKP                                                          4

SEQ ID NO: 14          moltype =   length =
SEQUENCE: 14
000

SEQ ID NO: 15          moltype =   length =
SEQUENCE: 15
000

SEQ ID NO: 16          moltype =   length =
SEQUENCE: 16
000

SEQ ID NO: 17          moltype = AA  length = 125
FEATURE                Location/Qualifiers
source                 1..125
                       mol_type = protein
                       organism = synthetic construct
SEQUENCE: 17
CDYPDIKHGG LYHENMRRPY FPVAVGKYYS YYCDEHFETP SGSYWDHIHC TQDGWSPAVP  60
CLRKCYFPYL ENGYNQNYGR KFVQGKSIDV ACHPGYALPK AQTTVTCMEN GWSPTPRCIR  120
VSFTL                                                         125

SEQ ID NO: 18          moltype = AA  length = 575
FEATURE                Location/Qualifiers
source                 1..575
                       mol_type = protein
                       organism = synthetic construct
SEQUENCE: 18
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LGGGGSGGGG SGGGGSTLKP CDYPDIKHGG LYHENMRRPY FPVAVGKYYS  480
YYCDEHFETP SGSYWDHIHC TQDGWSPAVP CLRKCYFPYL ENGYNQNYGR KFVQGKSIDV  540
ACHPGYALPK AQTTVTCMEN GWSPTPRCIR VSFTL                        575

SEQ ID NO: 19          moltype = AA  length = 574
FEATURE                Location/Qualifiers
source                 1..574
                       mol_type = protein
                       organism = synthetic construct
SEQUENCE: 19
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT GGGGSGGGGS GGGGSTLKPC DYPDIKHGGL YHENMRRPYF PVAVGKYYSY  480
YCDEHFETPS GSYWDHIHCT QDGWSPAVPC LRKCYFPYLE NGYNQNYGRK FVQGKSIDVA  540
CHPGYALPKA QTTVTCMENG WSPTPRCIRV SFTL                         574

SEQ ID NO: 20          moltype = AA  length = 573
FEATURE                Location/Qualifiers
source                 1..573
                       mol_type = protein
                       organism = synthetic construct
SEQUENCE: 20
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
```

```
WSPAVPCLRK CYFPYLENGY NQNYGRKFVQ GKSIDVACHP GYALPKAQTT VTCMENGWSP  420
TPRCIRVSFG GGGSGGGGSG GGGSTLKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                               573

SEQ ID NO: 21          moltype = AA  length = 572
FEATURE                Location/Qualifiers
source                 1..572
                       mol_type = protein
                       organism = synthetic construct
SEQUENCE: 21
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GGSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 22          moltype = AA  length = 571
FEATURE                Location/Qualifiers
source                 1..571
                       mol_type = protein
                       organism = synthetic construct
SEQUENCE: 22
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVGGG GSGGGGSGGG GSTLKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 23          moltype = AA  length = 570
FEATURE                Location/Qualifiers
source                 1..570
                       mol_type = protein
                       organism = synthetic construct
SEQUENCE: 23
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRGGGG SGGGGSGGGG STLKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                   570

SEQ ID NO: 24          moltype = AA  length = 569
FEATURE                Location/Qualifiers
source                 1..569
                       mol_type = protein
                       organism = synthetic construct
SEQUENCE: 24
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIGGGGS GGGGSGGGGS TLKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                    569

SEQ ID NO: 25          moltype = AA  length = 568
FEATURE                Location/Qualifiers
source                 1..568
                       mol_type = protein
                       organism = synthetic construct
SEQUENCE: 25
```

-continued

```
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCGGGGSG GGGSGGGGST LKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                     568

SEQ ID NO: 26           moltype = AA  length = 575
FEATURE                 Location/Qualifiers
source                  1..575
                        mol_type = protein
                        organism = synthetic construct
SEQUENCE: 26
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LEAAAKEAAA KEAAAKTLKP CDYPDIKHGG LYHENMRRPY FPVAVGKYYS  480
YYCDEHFETP SGSYWDHIHC TQDGWSPAVP CLRKCYFPYL ENGYNQNYGR KFVQGKSIDV  540
ACHPGYALPK AQTTVTCMEN GWSPTPRCIR VSFTL                              575

SEQ ID NO: 27           moltype = AA  length = 574
FEATURE                 Location/Qualifiers
source                  1..574
                        mol_type = protein
                        organism = synthetic construct
SEQUENCE: 27
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT EAAAKEAAAK EAAAKTLKPC DYPDIKHGGL YHENMRRPYF PVAVGKYYSY  480
YCDEHFETPS GSYWDHIHCT QDGWSPAVPC LRKCYFPYLE NGYNQNYGRK FVQGKSIDVA  540
CHPGYALPKA QTTVTCMENG WSPTPRCIRV SFTL                               574

SEQ ID NO: 28           moltype = AA  length = 573
FEATURE                 Location/Qualifiers
source                  1..573
                        mol_type = protein
                        organism = synthetic construct
SEQUENCE: 28
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFE AAAKEAAAKE AAAKTLKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                                573

SEQ ID NO: 29           moltype = AA  length = 572
FEATURE                 Location/Qualifiers
source                  1..572
                        mol_type = protein
                        organism = synthetic construct
SEQUENCE: 29
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSEA AAKEAAAKEA AAKTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                 572
```

```
SEQ ID NO: 30          moltype = AA  length = 571
FEATURE                Location/Qualifiers
source                 1..571
                       mol_type = protein
                       organism = synthetic construct
SEQUENCE: 30
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVEAA AKEAAAKEAA AKTLKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                571

SEQ ID NO: 31          moltype = AA  length = 570
FEATURE                Location/Qualifiers
source                 1..570
                       mol_type = protein
                       organism = synthetic construct
SEQUENCE: 31
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIREAAA KEAAAKEAAA KTLKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                  570

SEQ ID NO: 32          moltype = AA  length = 569
FEATURE                Location/Qualifiers
source                 1..569
                       mol_type = protein
                       organism = synthetic construct
SEQUENCE: 32
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIEAAAK EAAAKEAAAK TLKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                   569

SEQ ID NO: 33          moltype = AA  length = 568
FEATURE                Location/Qualifiers
source                 1..568
                       mol_type = protein
                       organism = synthetic construct
SEQUENCE: 33
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCEAAAKE AAAKEAAAKT LKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                    568

SEQ ID NO: 34          moltype = AA  length = 574
FEATURE                Location/Qualifiers
source                 1..574
                       mol_type = protein
                       organism = synthetic construct
SEQUENCE: 34
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
```

```
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LGGGGSGGGG SGGGGSLKPC DYPDIKHGGL YHENMRRPYF PVAVGKYYSY  480
YCDEHFETPS GSYWDHIHCT QDGWSPAVPC LRKCYFPYLE NGYNQNYGRK FVQGKSIDVA  540
CHPGYALPKA QTTVTCMENG WSPTPRCIRV SFTL                              574

SEQ ID NO: 35          moltype = AA  length = 573
FEATURE                Location/Qualifiers
source                 1..573
                       mol_type = protein
                       organism = synthetic construct
SEQUENCE: 35
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT GGGGSGGGGS GGGGSLKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                               573

SEQ ID NO: 36          moltype = AA  length = 572
FEATURE                Location/Qualifiers
source                 1..572
                       mol_type = protein
                       organism = synthetic construct
SEQUENCE: 36
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFG GGGSGGGGSG GGGSLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 37          moltype = AA  length = 571
FEATURE                Location/Qualifiers
source                 1..571
                       mol_type = protein
                       organism = synthetic construct
SEQUENCE: 37
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GGSLKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 38          moltype = AA  length = 570
FEATURE                Location/Qualifiers
source                 1..570
                       mol_type = protein
                       organism = synthetic construct
SEQUENCE: 38
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVGGG GSGGGGSGGG GSLKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                   570

SEQ ID NO: 39          moltype = AA  length = 569
FEATURE                Location/Qualifiers
source                 1..569
                       mol_type = protein
                       organism = synthetic construct
```

```
SEQUENCE: 39
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRGGGG SGGGGSGGGG SLKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                   569

SEQ ID NO: 40          moltype = AA  length = 568
FEATURE                Location/Qualifiers
source                 1..568
                       mol_type = protein
                       organism = synthetic construct
SEQUENCE: 40
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIGGGGS GGGGSGGGGS LKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                    568

SEQ ID NO: 41          moltype = AA  length = 567
FEATURE                Location/Qualifiers
source                 1..567
                       mol_type = protein
                       organism = synthetic construct
SEQUENCE: 41
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCGGGGSG GGGSGGGGSL KPCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                     567

SEQ ID NO: 42          moltype = AA  length = 574
FEATURE                Location/Qualifiers
source                 1..574
                       mol_type = protein
                       organism = synthetic construct
SEQUENCE: 42
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LEAAAKEAAA KEAAAKLKPC DYPDIKHGGL YHENMRRPYF PVAVGKYYSY  480
YCDEHFETPS GSYWDHIHCT QDGWSPAVPC LRKCYFPYLE NGYNQNYGRK FVQGKSIDVA  540
CHPGYALPKA QTTVTCMENG WSPTPRCIRV SFTL                              574

SEQ ID NO: 43          moltype = AA  length = 573
FEATURE                Location/Qualifiers
source                 1..573
                       mol_type = protein
                       organism = synthetic construct
SEQUENCE: 43
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT EAAAKEAAAK EAAAKLKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                               573
```

```
SEQ ID NO: 44          moltype = AA  length = 572
FEATURE                Location/Qualifiers
source                 1..572
                       mol_type = protein
                       organism = synthetic construct
SEQUENCE: 44
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFE AAAKEAAAKE AAAKLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 45          moltype = AA  length = 571
FEATURE                Location/Qualifiers
source                 1..571
                       mol_type = protein
                       organism = synthetic construct
SEQUENCE: 45
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSEA AAKEAAAKEA AAKLKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 46          moltype = AA  length = 570
FEATURE                Location/Qualifiers
source                 1..570
                       mol_type = protein
                       organism = synthetic construct
SEQUENCE: 46
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVEAA AKEAAAKEAA AKLKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                  570

SEQ ID NO: 47          moltype = AA  length = 569
FEATURE                Location/Qualifiers
source                 1..569
                       mol_type = protein
                       organism = synthetic construct
SEQUENCE: 47
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIREAAA KEAAAKEAAA KLKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                   569

SEQ ID NO: 48          moltype = AA  length = 568
FEATURE                Location/Qualifiers
source                 1..568
                       mol_type = protein
                       organism = synthetic construct
SEQUENCE: 48
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
```

```
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIEAAAK EAAAKEAAAK LKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                    568

SEQ ID NO: 49          moltype = AA  length = 567
FEATURE                Location/Qualifiers
source                 1..567
                       mol_type = protein
                       organism = synthetic construct
SEQUENCE: 49
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCEAAAKE AAAKEAAAKL KPCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                     567

SEQ ID NO: 50          moltype = AA  length = 573
FEATURE                Location/Qualifiers
source                 1..573
                       mol_type = protein
                       organism = synthetic construct
SEQUENCE: 50
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LGGGGSGGGG SGGGGSKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                              573

SEQ ID NO: 51          moltype = AA  length = 572
FEATURE                Location/Qualifiers
source                 1..572
                       mol_type = protein
                       organism = synthetic construct
SEQUENCE: 51
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT GGGGSGGGGS GGGGSKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                               572

SEQ ID NO: 52          moltype = AA  length = 571
FEATURE                Location/Qualifiers
source                 1..571
                       mol_type = protein
                       organism = synthetic construct
SEQUENCE: 52
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFG GGGSGGGGSG GGGSKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                571

SEQ ID NO: 53          moltype = AA  length = 570
FEATURE                Location/Qualifiers
source                 1..570
                       mol_type = protein
```

```
                       organism = synthetic construct
SEQUENCE: 53
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GGSKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                  570

SEQ ID NO: 54          moltype = AA  length = 569
FEATURE                Location/Qualifiers
source                 1..569
                       mol_type = protein
                       organism = synthetic construct
SEQUENCE: 54
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVGGG GSGGGGSGGG GSKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                   569

SEQ ID NO: 55          moltype = AA  length = 568
FEATURE                Location/Qualifiers
source                 1..568
                       mol_type = protein
                       organism = synthetic construct
SEQUENCE: 55
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRGGGG SGGGGSGGGG SKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                    568

SEQ ID NO: 56          moltype = AA  length = 567
FEATURE                Location/Qualifiers
source                 1..567
                       mol_type = protein
                       organism = synthetic construct
SEQUENCE: 56
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIGGGGS GGGGSGGGGS KPCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                     567

SEQ ID NO: 57          moltype = AA  length = 566
FEATURE                Location/Qualifiers
source                 1..566
                       mol_type = protein
                       organism = synthetic construct
SEQUENCE: 57
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCGGGGSG GGGSGGGGSK PCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
```

```
KAQTTVTCME NGWSPTPRCI RVSFTL                                 566

SEQ ID NO: 58          moltype = AA  length = 573
FEATURE                Location/Qualifiers
source                 1..573
                       mol_type = protein
                       organism = synthetic construct
SEQUENCE: 58
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LEAAAKEAAA KEAAAKKPCD YPDIKHGGLY HENMRRPYFP VAVGKYYSYY  480
CDEHFETPSG SYWDHIHCTQ DGWSPAVPCL RKCYFPYLEN GYNQNYGRKF VQGKSIDVAC  540
HPGYALPKAQ TTVTCMENGW SPTPRCIRVS FTL                         573

SEQ ID NO: 59          moltype = AA  length = 572
FEATURE                Location/Qualifiers
source                 1..572
                       mol_type = protein
                       organism = synthetic construct
SEQUENCE: 59
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT EAAAKEAAAK EAAAKKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                          572

SEQ ID NO: 60          moltype = AA  length = 571
FEATURE                Location/Qualifiers
source                 1..571
                       mol_type = protein
                       organism = synthetic construct
SEQUENCE: 60
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFE AAAKEAAAKE AAAKKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                           571

SEQ ID NO: 61          moltype = AA  length = 570
FEATURE                Location/Qualifiers
source                 1..570
                       mol_type = protein
                       organism = synthetic construct
SEQUENCE: 61
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSEA AAKEAAAKEA AAKKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                             570

SEQ ID NO: 62          moltype = AA  length = 569
FEATURE                Location/Qualifiers
source                 1..569
                       mol_type = protein
                       organism = synthetic construct
SEQUENCE: 62
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
```

```
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVEAA AKEAAAKEAA AKKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                    569

SEQ ID NO: 63           moltype = AA  length = 568
FEATURE                 Location/Qualifiers
source                  1..568
                        mol_type = protein
                        organism = synthetic construct
SEQUENCE: 63
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIREAAA KEAAAKEAAA KKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                     568

SEQ ID NO: 64           moltype = AA  length = 567
FEATURE                 Location/Qualifiers
source                  1..567
                        mol_type = protein
                        organism = synthetic construct
SEQUENCE: 64
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIEAAAK EAAAKEAAAK KPCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                      567

SEQ ID NO: 65           moltype = AA  length = 566
FEATURE                 Location/Qualifiers
source                  1..566
                        mol_type = protein
                        organism = synthetic construct
SEQUENCE: 65
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCEAAAKE AAAKEAAAKK PCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
KAQTTVTCME NGWSPTPRCI RVSFTL                                       566

SEQ ID NO: 66           moltype = AA  length = 572
FEATURE                 Location/Qualifiers
source                  1..572
                        mol_type = protein
                        organism = synthetic construct
SEQUENCE: 66
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LGGGGSGGGG SGGGGSPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 67           moltype = AA  length = 571
FEATURE                 Location/Qualifiers
source                  1..571
```

```
                        mol_type = protein
                        organism = synthetic construct
SEQUENCE: 67
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT GGGGSGGGGS GGGGSPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 68           moltype = AA  length = 570
FEATURE                 Location/Qualifiers
source                  1..570
                        mol_type = protein
                        organism = synthetic construct
SEQUENCE: 68
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFG GGGSGGGGSG GGGSPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                  570

SEQ ID NO: 69           moltype = AA  length = 569
FEATURE                 Location/Qualifiers
source                  1..569
                        mol_type = protein
                        organism = synthetic construct
SEQUENCE: 69
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GGSPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                   569

SEQ ID NO: 70           moltype = AA  length = 568
FEATURE                 Location/Qualifiers
source                  1..568
                        mol_type = protein
                        organism = synthetic construct
SEQUENCE: 70
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVGGG GSGGGGSGGG GSPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                    568

SEQ ID NO: 71           moltype = AA  length = 567
FEATURE                 Location/Qualifiers
source                  1..567
                        mol_type = protein
                        organism = synthetic construct
SEQUENCE: 71
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRGGGG SGGGGSGGGG SPCDYPDIKH GGLYHENMRR PYFPVAVGKY YSYYCDEHFE  480
```

```
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                      567

SEQ ID NO: 72          moltype = AA  length = 566
FEATURE                Location/Qualifiers
source                 1..566
                       mol_type = protein
                       organism = synthetic construct
SEQUENCE: 72
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIGGGGS GGGGSGGGGS PCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
KAQTTVTCME NGWSPTPRCI RVSFTL                                       566

SEQ ID NO: 73          moltype = AA  length = 565
FEATURE                Location/Qualifiers
source                 1..565
                       mol_type = protein
                       organism = synthetic construct
SEQUENCE: 73
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCGGGGSG GGGSGGGGSP CDYPDIKHGG LYHENMRRPY FPVAVGKYYS YYCDEHFETP  480
SGSYWDHIHC TQDGWSPAVP CLRKCYFPYL ENGYNQNYGR KFVQGKSIDV ACHPGYALPK  540
AQTTVTCMEN GWSPTPRCIR VSFTL                                        565

SEQ ID NO: 74          moltype = AA  length = 572
FEATURE                Location/Qualifiers
source                 1..572
                       mol_type = protein
                       organism = synthetic construct
SEQUENCE: 74
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LEAAAKEAAA KEAAAKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 75          moltype = AA  length = 571
FEATURE                Location/Qualifiers
source                 1..571
                       mol_type = protein
                       organism = synthetic construct
SEQUENCE: 75
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT EAAAKEAAAK EAAAKPCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 76          moltype = AA  length = 570
FEATURE                Location/Qualifiers
source                 1..570
                       mol_type = protein
                       organism = synthetic construct
SEQUENCE: 76
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
```

```
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFE AAAKEAAAKE AAAKPCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                   570

SEQ ID NO: 77          moltype = AA  length = 569
FEATURE                Location/Qualifiers
source                 1..569
                       mol_type = protein
                       organism = synthetic construct
SEQUENCE: 77
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSEA AAKEAAAKEA AAKPCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                    569

SEQ ID NO: 78          moltype = AA  length = 568
FEATURE                Location/Qualifiers
source                 1..568
                       mol_type = protein
                       organism = synthetic construct
SEQUENCE: 78
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVEAA AKEAAAKEAA AKPCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                     568

SEQ ID NO: 79          moltype = AA  length = 567
FEATURE                Location/Qualifiers
source                 1..567
                       mol_type = protein
                       organism = synthetic construct
SEQUENCE: 79
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIREAAA KEAAAKEAAA KPCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                      567

SEQ ID NO: 80          moltype = AA  length = 566
FEATURE                Location/Qualifiers
source                 1..566
                       mol_type = protein
                       organism = synthetic construct
SEQUENCE: 80
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIEAAAK EAAAKEAAAK PCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
KAQTTVTCME NGWSPTPRCI RVSFTL                                       566

SEQ ID NO: 81          moltype = AA  length = 565
FEATURE                Location/Qualifiers
```

```
source                  1..565
                        mol_type = protein
                        organism = synthetic construct
SEQUENCE: 81
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCEAAAKE AAAKEAAAKP CDYPDIKHGG LYHENMRRPY FPVAVGKYYS YYCDEHFETP  480
SGSYWDHIHC TQDGWSPAVP CLRKCYFPYL ENGYNQNYGR KFVQGKSIDV ACHPGYALPK  540
AQTTVTCMEN GWSPTPRCIR VSFTL                                        565

SEQ ID NO: 82           moltype = AA  length = 571
FEATURE                 Location/Qualifiers
source                  1..571
                        mol_type = protein
                        organism = synthetic construct
SEQUENCE: 82
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LGGGGSGGGG SGGGGSCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 83           moltype = AA  length = 570
FEATURE                 Location/Qualifiers
source                  1..570
                        mol_type = protein
                        organism = synthetic construct
SEQUENCE: 83
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT GGGGSGGGGS GGGGSCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                   570

SEQ ID NO: 84           moltype = AA  length = 569
FEATURE                 Location/Qualifiers
source                  1..569
                        mol_type = protein
                        organism = synthetic construct
SEQUENCE: 84
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFG GGGSGGGGSG GGGSCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                    569

SEQ ID NO: 85           moltype = AA  length = 568
FEATURE                 Location/Qualifiers
source                  1..568
                        mol_type = protein
                        organism = synthetic construct
SEQUENCE: 85
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
```

```
TPRCIRVSGG GGSGGGGSGG GGSCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                     568

SEQ ID NO: 86          moltype = AA  length = 567
FEATURE                Location/Qualifiers
source                 1..567
                       mol_type = protein
                       organism = synthetic construct
SEQUENCE: 86
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVGGG GSGGGGSGGG GSCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                      567

SEQ ID NO: 87          moltype = AA  length = 566
FEATURE                Location/Qualifiers
source                 1..566
                       mol_type = protein
                       organism = synthetic construct
SEQUENCE: 87
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRGGGG SGGGGSGGGG SCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
KAQTTVTCME NGWSPTPRCI RVSFTL                                       566

SEQ ID NO: 88          moltype = AA  length = 565
FEATURE                Location/Qualifiers
source                 1..565
                       mol_type = protein
                       organism = synthetic construct
SEQUENCE: 88
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIGGGGS GGGGSGGGGS CDYPDIKHGG LYHENMRRPY FPVAVGKYYS YYCDEHFETP  480
SGSYWDHIHC TQDGWSPAVP CLRKCYFPYL ENGYNQNYGR KFVQGKSIDV ACHPGYALPK  540
AQTTVTCMEN GWSPTPRCIR VSFTL                                        565

SEQ ID NO: 89          moltype = AA  length = 564
FEATURE                Location/Qualifiers
source                 1..564
                       mol_type = protein
                       organism = synthetic construct
SEQUENCE: 89
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCGGGGSG GGGSGGGGSC DYPDIKHGGL YHENMRRPYF PVAVGKYYSY YCDEHFETPS  480
GSYWDHIHCT QDGWSPAVPC LRKCYFPYLE NGYNQNYGRK FVQGKSIDVA CHPGYALPKA  540
QTTVTCMENG WSPTPRCIRV SFTL                                         564

SEQ ID NO: 90          moltype = AA  length = 571
FEATURE                Location/Qualifiers
source                 1..571
                       mol_type = protein
                       organism = synthetic construct
SEQUENCE: 90
EDCNELPPRR NTEILTGSWS DQTYPEGTQA IYKCRPGYRS LGNVIMVCRK GEWVALNPLR  60
```

```
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT LEAAAKEAAA KEAAAKCDYP DIKHGGLYHE NMRRPYFPVA VGKYYSYYCD  480
EHFETPSGSY WDHIHCTQDG WSPAVPCLRK CYFPYLENGY NQNYGRKFVQ GKSIDVACHP  540
GYALPKAQTT VTCMENGWSP TPRCIRVSFT L                                 571

SEQ ID NO: 91          moltype = AA  length = 570
FEATURE                Location/Qualifiers
source                 1..570
                       mol_type = protein
                       organism = synthetic construct
SEQUENCE: 91
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT EAAAKEAAAK EAAAKCDYPD IKHGGLYHEN MRRPYFPVAV GKYYSYYCDE  480
HFETPSGSYW DHIHCTQDGW SPAVPCLRKC YFPYLENGYN QNYGRKFVQG KSIDVACHPG  540
YALPKAQTTV TCMENGWSPT PRCIRVSFTL                                   570

SEQ ID NO: 92          moltype = AA  length = 569
FEATURE                Location/Qualifiers
source                 1..569
                       mol_type = protein
                       organism = synthetic construct
SEQUENCE: 92
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFE AAAKEAAAKE AAAKCDYPDI KHGGLYHENM RRPYFPVAVG KYYSYYCDEH  480
FETPSGSYWD HIHCTQDGWS PAVPCLRKCY FPYLENGYNQ NYGRKFVQGK SIDVACHPGY  540
ALPKAQTTVT CMENGWSPTP RCIRVSFTL                                    569

SEQ ID NO: 93          moltype = AA  length = 568
FEATURE                Location/Qualifiers
source                 1..568
                       mol_type = protein
                       organism = synthetic construct
SEQUENCE: 93
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSEA AAKEAAAKEA AAKCDYPDIK HGGLYHENMR RPYFPVAVGK YYSYYCDEHF  480
ETPSGSYWDH IHCTQDGWSP AVPCLRKCYF PYLENGYNQN YGRKFVQGKS IDVACHPGYA  540
LPKAQTTVTC MENGWSPTPR CIRVSFTL                                     568

SEQ ID NO: 94          moltype = AA  length = 567
FEATURE                Location/Qualifiers
source                 1..567
                       mol_type = protein
                       organism = synthetic construct
SEQUENCE: 94
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVEAA AKEAAAKEAA AKCDYPDIKH GGLYHENMRR PYFPVAVGKY YSYYCDEHFE  480
TPSGSYWDHI HCTQDGWSPA VPCLRKCYFP YLENGYNQNY GRKFVQGKSI DVACHPGYAL  540
PKAQTTVTCM ENGWSPTPRC IRVSFTL                                      567

SEQ ID NO: 95          moltype = AA  length = 566
```

```
FEATURE                Location/Qualifiers
source                 1..566
                       mol_type = protein
                       organism = synthetic construct
SEQUENCE: 95
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIREAAA KEAAAKEAAA KCDYPDIKHG GLYHENMRRP YFPVAVGKYY SYYCDEHFET  480
PSGSYWDHIH CTQDGWSPAV PCLRKCYFPY LENGYNQNYG RKFVQGKSID VACHPGYALP  540
KAQTTVTCME NGWSPTPRCI RVSFTL                                      566

SEQ ID NO: 96          moltype = AA  length = 565
FEATURE                Location/Qualifiers
source                 1..565
                       mol_type = protein
                       organism = synthetic construct
SEQUENCE: 96
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIEAAAK EAAAKEAAAK CDYPDIKHGG LYHENMRRPY FPVAVGKYYS YYCDEHFETP  480
SGSYWDHIHC TQDGWSPAVP CLRKCYFPYL ENGYNQNYGR KFVQGKSIDV ACHPGYALPK  540
AQTTVTCMEN GWSPTPRCIR VSFTL                                       565

SEQ ID NO: 97          moltype = AA  length = 564
FEATURE                Location/Qualifiers
source                 1..564
                       mol_type = protein
                       organism = synthetic construct
SEQUENCE: 97
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCEAAAKE AAAKEAAAKC DYPDIKHGGL YHENMRRPYF PVAVGKYYSY YCDEHFETPS  480
GSYWDHIHCT QDGWSPAVPC LRKCYFPYLE NGYNQNYGRK FVQGKSIDVA CHPGYALPKA  540
QTTVTCMENG WSPTPRCIRV SFTL                                        564

SEQ ID NO: 98          moltype = AA  length = 431
FEATURE                Location/Qualifiers
source                 1..431
                       mol_type = protein
                       organism = synthetic construct
SEQUENCE: 98
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                      431

SEQ ID NO: 99          moltype = AA  length = 553
FEATURE                Location/Qualifiers
source                 1..553
                       mol_type = protein
                       organism = synthetic construct
SEQUENCE: 99
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCTLKPCD YPDIKHGGLY HENMRRPYFP VAVGKYYSYY CDEHFETPSG SYWDHIHCTQ  480
```

```
DGWSPAVPCL RKCYFPYLEN GYNQNYGRKF VQGKSIDVAC HPGYALPKAQ TTVTCMENGW  540
SPTPRCIRVS FTL                                                     553

SEQ ID NO: 100          moltype = AA  length = 552
FEATURE                 Location/Qualifiers
source                  1..552
                        mol_type = protein
                        organism = synthetic construct
SEQUENCE: 100
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCLKPCDY PDIKHGGLYH ENMRRPYFPV AVGKYYSYYC DEHFETPSGS YWDHIHCTQD  480
GWSPAVPCLR KCYFPYLENG YNQNYGRKFV QGKSIDVACH PGYALPKAQT TVTCMENGWS  540
PTPRCIRVSF TL                                                      552

SEQ ID NO: 101          moltype = AA  length = 553
FEATURE                 Location/Qualifiers
source                  1..553
                        mol_type = protein
                        organism = synthetic construct
SEQUENCE: 101
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCILKPCD YPDIKHGGLY HENMRRPYFP VAVGKYYSYY CDEHFETPSG SYWDHIHCTQ  480
DGWSPAVPCL RKCYFPYLEN GYNQNYGRKF VQGKSIDVAC HPGYALPKAQ TTVTCMENGW  540
SPTPRCIRVS FTL                                                     553

SEQ ID NO: 102          moltype = AA  length = 552
FEATURE                 Location/Qualifiers
source                  1..552
                        mol_type = protein
                        organism = synthetic construct
SEQUENCE: 102
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIKPCDY PDIKHGGLYH ENMRRPYFPV AVGKYYSYYC DEHFETPSGS YWDHIHCTQD  480
GWSPAVPCLR KCYFPYLENG YNQNYGRKFV QGKSIDVACH PGYALPKAQT TVTCMENGWS  540
PTPRCIRVSF TL                                                      552

SEQ ID NO: 103          moltype = AA  length = 553
FEATURE                 Location/Qualifiers
source                  1..553
                        mol_type = protein
                        organism = synthetic construct
SEQUENCE: 103
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRKPCD YPDIKHGGLY HENMRRPYFP VAVGKYYSYY CDEHFETPSG SYWDHIHCTQ  480
DGWSPAVPCL RKCYFPYLEN GYNQNYGRKF VQGKSIDVAC HPGYALPKAQ TTVTCMENGW  540
SPTPRCIRVS FTL                                                     553

SEQ ID NO: 104          moltype = AA  length = 552
FEATURE                 Location/Qualifiers
source                  1..552
                        mol_type = protein
                        organism = synthetic construct
SEQUENCE: 104
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
```

-continued

```
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRPCDY PDIKHGGLYH ENMRRPYFPV AVGKYYSYYC DEHFETPSGS YWDHIHCTQD  480
GWSPAVPCLR KCYFPYLENG YNQNYGRKFV QGKSIDVACH PGYALPKAQT TVTCMENGWS  540
PTPRCIRVSF TL                                                      552

SEQ ID NO: 105          moltype = AA  length = 552
FEATURE                 Location/Qualifiers
source                  1..552
                        mol_type = protein
                        organism = synthetic construct
SEQUENCE: 105
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVCDY PDIKHGGLYH ENMRRPYFPV AVGKYYSYYC DEHFETPSGS YWDHIHCTQD  480
GWSPAVPCLR KCYFPYLENG YNQNYGRKFV QGKSIDVACH PGYALPKAQT TVTCMENGWS  540
PTPRCIRVSF TL                                                      552

SEQ ID NO: 106          moltype = AA  length = 553
FEATURE                 Location/Qualifiers
source                  1..553
                        mol_type = protein
                        organism = synthetic construct
SEQUENCE: 106
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSCD YPDIKHGGLY HENMRRPYFP VAVGKYYSYY CDEHFETPSG SYWDHIHCTQ  480
DGWSPAVPCL RKCYFPYLEN GYNQNYGRKF VQGKSIDVAC HPGYALPKAQ TTVTCMENGW  540
SPTPRCIRVS FTL                                                     553

SEQ ID NO: 107          moltype = AA  length = 431
FEATURE                 Location/Qualifiers
source                  1..431
                        mol_type = protein
                        organism = synthetic construct
SEQUENCE: 107
EDCNESPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 108          moltype = AA  length = 431
FEATURE                 Location/Qualifiers
source                  1..431
                        mol_type = protein
                        organism = synthetic construct
SEQUENCE: 108
EDCNETPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 109          moltype = AA  length = 431
FEATURE                 Location/Qualifiers
source                  1..431
                        mol_type = protein
                        organism = synthetic construct
SEQUENCE: 109
```

```
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTSK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                      431

SEQ ID NO: 110         moltype = AA  length = 431
FEATURE                Location/Qualifiers
source                 1..431
                       mol_type = protein
                       organism = synthetic construct
SEQUENCE: 110
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTTK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                      431

SEQ ID NO: 111         moltype = AA  length = 431
FEATURE                Location/Qualifiers
source                 1..431
                       mol_type = protein
                       organism = synthetic construct
SEQUENCE: 111
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGS NQNYGRKFVQ GKSIDVACHP GYALPKAQTT VTCMENGWSP  420
TPRCIRVSFT L                                                      431

SEQ ID NO: 112         moltype = AA  length = 431
FEATURE                Location/Qualifiers
source                 1..431
                       mol_type = protein
                       organism = synthetic construct
SEQUENCE: 112
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGT NQNYGRKFVQ GKSIDVACHP GYALPKAQTT VTCMENGWSP  420
TPRCIRVSFT L                                                      431

SEQ ID NO: 113         moltype = AA  length = 431
FEATURE                Location/Qualifiers
source                 1..431
                       mol_type = protein
                       organism = synthetic construct
SEQUENCE: 113
EDCNELPPRR NTEILNGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                      431

SEQ ID NO: 114         moltype = AA  length = 431
FEATURE                Location/Qualifiers
source                 1..431
                       mol_type = protein
                       organism = synthetic construct
SEQUENCE: 114
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
```

```
LPSCEEKSCD NPYIPNGNYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 115         moltype = AA  length = 431
FEATURE                Location/Qualifiers
source                 1..431
                       mol_type = protein
                       organism = synthetic construct
SEQUENCE: 115
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKNYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 116         moltype = AA  length = 431
FEATURE                Location/Qualifiers
source                 1..431
                       mol_type = protein
                       organism = synthetic construct
SEQUENCE: 116
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 117         moltype = AA  length = 431
FEATURE                Location/Qualifiers
source                 1..431
                       mol_type = protein
                       organism = synthetic construct
SEQUENCE: 117
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRNNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 118         moltype = AA  length = 431
FEATURE                Location/Qualifiers
source                 1..431
                       mol_type = protein
                       organism = synthetic construct
SEQUENCE: 118
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHINCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 119         moltype = AA  length = 431
FEATURE                Location/Qualifiers
source                 1..431
                       mol_type = protein
                       organism = synthetic construct
SEQUENCE: 119
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKNQTT VTCMENGWSP  420
TPRCIRVSFT L                                                       431
```

```
SEQ ID NO: 120         moltype = AA  length = 431
FEATURE                Location/Qualifiers
source                 1..431
                       mol_type = protein
                       organism = synthetic construct
SEQUENCE: 120
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCINVSFT L                                                       431

SEQ ID NO: 121         moltype = AA  length = 431
FEATURE                Location/Qualifiers
source                 1..431
                       mol_type = protein
                       organism = synthetic construct
SEQUENCE: 121
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVNFT L                                                       431

SEQ ID NO: 122         moltype = AA  length = 572
FEATURE                Location/Qualifiers
source                 1..572
                       mol_type = protein
                       organism = synthetic construct
SEQUENCE: 122
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG NGSGGGGSGG GGSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 123         moltype = AA  length = 572
FEATURE                Location/Qualifiers
source                 1..572
                       mol_type = protein
                       organism = synthetic construct
SEQUENCE: 123
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGNGSGG GGSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 124         moltype = AA  length = 572
FEATURE                Location/Qualifiers
source                 1..572
                       mol_type = protein
                       organism = synthetic construct
SEQUENCE: 124
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG NGSTLKPCDY PDIKHGGLYH ENMRRPYFPV AVGKYYSYYC  480
```

```
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 125          moltype = AA  length = 572
FEATURE                 Location/Qualifiers
source                  1..572
                        mol_type = protein
                        organism = synthetic construct
SEQUENCE: 125
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 126          moltype = AA  length = 431
FEATURE                 Location/Qualifiers
source                  1..431
                        mol_type = protein
                        organism = synthetic construct
SEQUENCE: 126
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRNNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 127          moltype = AA  length = 431
FEATURE                 Location/Qualifiers
source                  1..431
                        mol_type = protein
                        organism = synthetic construct
SEQUENCE: 127
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTTK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSFT L                                                       431

SEQ ID NO: 128          moltype = AA  length = 572
FEATURE                 Location/Qualifiers
source                  1..572
                        mol_type = protein
                        organism = synthetic construct
SEQUENCE: 128
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 129          moltype = AA  length = 572
FEATURE                 Location/Qualifiers
source                  1..572
                        mol_type = protein
                        organism = synthetic construct
SEQUENCE: 129
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRNNTAK CTSTGWIPAP  300
RCTLKPCDYP DIKHGGLYHE NMRRPYFPVA VGKYYSYYCD EHFETPSGSY WDHIHCTQDG  360
```

```
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 130         moltype = AA  length = 572
FEATURE                Location/Qualifiers
source                 1..572
                       mol_type = protein
                       organism = synthetic construct
SEQUENCE: 130
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTTK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 131         moltype = AA  length = 572
FEATURE                Location/Qualifiers
source                 1..572
                       mol_type = protein
                       organism = synthetic construct
SEQUENCE: 131
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRNNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 132         moltype = AA  length = 572
FEATURE                Location/Qualifiers
source                 1..572
                       mol_type = protein
                       organism = synthetic construct
SEQUENCE: 132
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTTK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVSGG GGSGGGGSGG GNSTLKPCDY PDIKHGGLYH ENMRRPYFPV AVGKYYSYYC  480
DEHFETPSGS YWDHIHCTQD GWSPAVPCLR KCYFPYLENG YNQNYGRKFV QGKSIDVACH  540
PGYALPKAQT TVTCMENGWS PTPRCIRVSF TL                                572

SEQ ID NO: 133         moltype = AA  length = 1213
FEATURE                Location/Qualifiers
source                 1..1213
                       mol_type = protein
                       organism = synthetic construct
SEQUENCE: 133
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVKTC SKSSIDIENG FISESQYTYA LKEKAKYQCK LGYVTADGET SGSITCGKDG  480
WSAQPTCIKS CDIPVFMNAR TKNDFTWFKL NDTLDYECHD GYESNTGSTT GSIVCGYNGW  540
SDLPICYERE CELPKIDVHL VPDRKKDQYK VGEVLKFSCK PGFTIVGPNS VQCYHFGLSP  600
DLPICKEQVQ SCGPPPELLN GNVKEKTKEE YGHSEVVEYY CNPRFLMKGP NKIQCVDGEW  660
TTLPVCIVEE STCGDIPELE HGWAQLSSPP YYYGDSVEFN CSESFTMIGH RSITCIHGVW  720
TQLPQCVAID KLKKCKSSNL IILEEHLKNK KEFDHNSNIR YRCRGKEGWI HTVCINGRWD  780
PEVNCSMAQI QLCPPPPQIP NSHNMTTTLN YRDGEKVSVL CQENYLIQEG EEITCKDGRW  840
QSIPLCVEKI PCSQPPQIEH GTINSSRSSQ ESYAHGTKLS YTCEGGFRIS EENETTCYMG  900
KWSSPPQCEG LPCKSPPEIS HGVVAHMSDS YQYGEEVTYK CFEGFGIDGP AIAKCLGEKW  960
SHPPSCIKTD CLSLPSFENA IPMGEKKDVY KAGEQVTYTC ATYYKMDGAS NVTCINSRWT  1020
```

```
GRPTCRDTSC VNPPTVQNAY IVSRQMSKYP SGERVRYQCR SPYEMFGDEE VMCLNGNWTE  1080
PPQCKDSTGK CGPPPPIDNG DITSFPLSVY APASSVEYQC QNLYQLEGNK RITCRNGQWS  1140
EPPKCLHPCV ISREIMENYN IALRWTAKQK LYSRTGESVE FVCKRGYRLS SRSHTLRTTC  1200
WDGKLEYPTC AKR                                                     1213

SEQ ID NO: 134         moltype = AA  length = 428
FEATURE                Location/Qualifiers
source                 1..428
                       mol_type = protein
                       organism = synthetic construct
SEQUENCE: 134
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVS                                                           428

SEQ ID NO: 135         moltype = AA  length = 129
FEATURE                Location/Qualifiers
source                 1..129
                       mol_type = protein
                       organism = synthetic construct
SEQUENCE: 135
TLKPCDYPDI KHGGLYHENM RRPYFPVAVG KYYSYYCDEH FETPSGSYWD HIHCTQDGWS  60
PAVPCLRKCY FPYLENGYNQ NYGRKFVQGK SIDVACHPGY ALPKAQTTVT CMENGWSPTP  120
RCIRVSFTL                                                          129

SEQ ID NO: 136         moltype = AA  length = 428
FEATURE                Location/Qualifiers
source                 1..428
                       mol_type = protein
                       organism = synthetic construct
SEQUENCE: 136
EDCNELPPRR NTEILTGSWS DQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVS                                                           428

SEQ ID NO: 137         moltype = AA  length = 128
FEATURE                Location/Qualifiers
source                 1..128
                       mol_type = protein
                       organism = synthetic construct
SEQUENCE: 137
LKPCDYPDIK HGGLYHENMR RPYFPVAVGK YYSYYCDEHF ETPSGSYWDH IHCTQDGWSP  60
AVPCLRKCYF PYLENGYNQN YGRKFVQGKS IDVACHPGYA LPKAQTTVTC MENGWSPTPR  120
CIRVSFTL                                                           128

SEQ ID NO: 138         moltype = AA  length = 15
FEATURE                Location/Qualifiers
source                 1..15
                       mol_type = protein
                       organism = synthetic construct
SEQUENCE: 138
GGGGSGGGGS GGGNS                                                   15

SEQ ID NO: 139         moltype = AA  length = 428
FEATURE                Location/Qualifiers
source                 1..428
                       mol_type = protein
                       organism = synthetic construct
SEQUENCE: 139
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRNNTAK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVS                                                           428

SEQ ID NO: 140         moltype = AA  length = 428
```

```
FEATURE                Location/Qualifiers
source                 1..428
                       mol_type = protein
                       organism = synthetic construct
SEQUENCE: 140
EDCNELPPRR NTEILTGSWS NQTYPEGTQA IYKCRPGYRS LGNVIMVCRK GEWVALNPLR  60
KCQKRPCGHP GDTPFGTFTL TGGNVFEYGV KAVYTCNEGY QLLGEINYRE CDTDGWTNDI  120
PICEVVKCLP VTAPENGKIV SSAMEPDREY HFGQAVRFVC NSGYKIEGDE EMHCSDDGFW  180
SKEKPKCVEI SCKSPDVING SPISQKIIYK ENERFQYKCN MGYEYSERGD AVCTESGWRP  240
LPSCEEKSCD NPYIPNGDYS PLRIKHRTGD EITYQCRNGF YPATRGNTTK CTSTGWIPAP  300
RCTLKPCDYP DIKHGGLYHE NMRRPYFPVA VGKYYSYYCD EHFETPSGSY WDHIHCTQDG  360
WSPAVPCLRK CYFPYLENGY NQNYGRKFVQ GKSIDVACHP GYALPKAQTT VTCMENGWSP  420
TPRCIRVS                                                          428

SEQ ID NO: 141         moltype = AA  length = 4
FEATURE                Location/Qualifiers
source                 1..4
                       mol_type = protein
                       organism = synthetic construct
SEQUENCE: 141
GGGS                                                              4

SEQ ID NO: 142         moltype = AA  length = 8
FEATURE                Location/Qualifiers
source                 1..8
                       mol_type = protein
                       organism = synthetic construct
SEQUENCE: 142
GGGSGGGS                                                          8

SEQ ID NO: 143         moltype = AA  length = 9
FEATURE                Location/Qualifiers
source                 1..9
                       mol_type = protein
                       organism = synthetic construct
SEQUENCE: 143
GGGGSGGGS                                                         9

SEQ ID NO: 144         moltype = AA  length = 13
FEATURE                Location/Qualifiers
source                 1..13
                       mol_type = protein
                       organism = synthetic construct
SEQUENCE: 144
GGGGSGGGSG GGS                                                    13

SEQ ID NO: 145         moltype = AA  length = 5
FEATURE                Location/Qualifiers
source                 1..5
                       mol_type = protein
                       organism = synthetic construct
SEQUENCE: 145
EAAAK                                                             5

SEQ ID NO: 146         moltype = AA  length = 10
FEATURE                Location/Qualifiers
source                 1..10
                       mol_type = protein
                       organism = synthetic construct
SEQUENCE: 146
EAAAKEAAAK                                                        10

SEQ ID NO: 147         moltype = AA  length = 19
FEATURE                Location/Qualifiers
source                 1..19
                       mol_type = protein
                       organism = synthetic construct
SEQUENCE: 147
MGWSCIILFL VATATGVHS                                              19

SEQ ID NO: 148         moltype = AA  length = 12
FEATURE                Location/Qualifiers
source                 1..12
                       mol_type = protein
                       organism = synthetic construct
SEQUENCE: 148
GGSGGSGGSG GS                                                     12

SEQ ID NO: 149         moltype = AA  length = 10
```

-continued

```
FEATURE                 Location/Qualifiers
source                  1..10
                        mol_type = protein
                        organism = synthetic construct
SEQUENCE: 149
GGGGSGGGGS                                                    10

SEQ ID NO: 150          moltype = AA  length = 18
FEATURE                 Location/Qualifiers
source                  1..18
                        mol_type = protein
                        organism = synthetic construct
SEQUENCE: 150
MRLLAKIICL MLWAICVA                                           18
```